(12) United States Patent
Deisseroth et al.

(10) Patent No.: US 11,103,723 B2
(45) Date of Patent: Aug. 31, 2021

(54) METHODS FOR TREATING NEUROGENIC DISORDERS OF THE PELVIC FLOOR

(71) Applicants: The Board of Trustees of the Leland Stanford Junior University, Stanford, CA (US); Circuit Therapeutics, Inc., Menlo Park, CA (US)

(72) Inventors: Karl A. Deisseroth, Stanford, CA (US); Elizabeth R. Aden, Berkeley, CA (US); Viviana Gradinaru, Menlo Park, CA (US); Scott L. Delp, Stanford, CA (US)

(73) Assignees: The Board of Trustees of the Leland Stanford Junior University, Stanford, CA (US); Circuit Therapeutics, Inc., Menlo Park, CA (US)

( * ) Notice: Subject to any disclaimer, the term of this patent is extended or adjusted under 35 U.S.C. 154(b) by 190 days.

(21) Appl. No.: 14/921,929

(22) Filed: Oct. 23, 2015

(65) Prior Publication Data

US 2016/0038761 A1 Feb. 11, 2016

Related U.S. Application Data

(63) Continuation of application No. 13/772,732, filed on Feb. 21, 2013, now abandoned.

(60) Provisional application No. 61/601,298, filed on Feb. 21, 2012.

(51) Int. Cl.
| | |
|---|---|
| *A61N 5/06* | (2006.01) |
| *A61K 48/00* | (2006.01) |
| *A61K 49/00* | (2006.01) |
| *A61K 38/17* | (2006.01) |

(52) U.S. Cl.
CPC ............ *A61N 5/062* (2013.01); *A61K 38/177* (2013.01); *A61K 48/005* (2013.01); *A61K 49/0008* (2013.01); *A61N 2005/0663* (2013.01); *C12N 2750/14141* (2013.01)

(58) Field of Classification Search
CPC .. A61K 35/30; A61K 2300/00; A61K 48/005; A61K 48/0058; A61N 5/0622; A61N 2005/0651; A61N 5/0601; A61N 5/062; G01N 33/6872; C07K 14/705; C07K 2319/60; C12N 2740/15043; C12N 2740/15071
See application file for complete search history.

(56) References Cited

U.S. PATENT DOCUMENTS

| | | | |
|---|---|---|---|
| 2,968,302 A | 1/1961 | Fry et al. | |
| 3,131,690 A | 5/1964 | Innis et al. | |
| 3,499,437 A | 3/1970 | Balamuth et al. | |
| 3,567,847 A | 3/1971 | Price | |
| 4,343,301 A | 8/1982 | Indech | |
| 4,559,951 A | 12/1985 | Dahl et al. | |
| 4,616,231 A | 10/1986 | Autrey et al. | |
| 4,865,042 A | 9/1989 | Umemura et al. | |
| 4,879,284 A | 11/1989 | Lang et al. | |
| 5,032,123 A | 7/1991 | Katz et al. | |
| 5,041,224 A | 8/1991 | Ohyama et al. | |
| 5,082,670 A | 1/1992 | Gage et al. | |
| 5,249,575 A | 10/1993 | Di Mino et al. | |
| 5,267,152 A | 11/1993 | Yang et al. | |
| 5,290,280 A | 3/1994 | Daikuzono et al. | |
| 5,330,515 A | 7/1994 | Rutecki et al. | |
| 5,382,516 A | 1/1995 | Bush | |
| 5,411,540 A | 5/1995 | Edell et al. | |
| 5,445,608 A | 8/1995 | Chen et al. | |
| 5,460,950 A | 10/1995 | Barr et al. | |
| 5,460,954 A | 10/1995 | Lee et al. | |
| 5,470,307 A | 11/1995 | Lindall | |
| 5,495,541 A | 2/1996 | Murray et al. | |
| 5,520,188 A | 5/1996 | Hennige et al. | |
| 5,527,695 A | 6/1996 | Hodges et al. | |
| 5,550,316 A | 8/1996 | Mintz | |
| 5,641,650 A | 6/1997 | Turner et al. | |
| 5,703,985 A | 12/1997 | Owyang et al. | |
| 5,722,426 A | 3/1998 | Kolff | |
| 5,738,625 A | 4/1998 | Gluck | |
| 5,739,273 A | 4/1998 | Engelman et al. | |
| 5,741,316 A | 4/1998 | Chen et al. | |
| 5,755,750 A | 5/1998 | Petruska et al. | |
| 5,756,351 A | 5/1998 | Isacoff et al. | |
| 5,782,896 A | 7/1998 | Chen et al. | |
| 5,795,581 A | 8/1998 | Segalman et al. | |
| 5,807,285 A | 9/1998 | Vaitekunas et al. | |
| 5,816,256 A | 10/1998 | Kissinger et al. | |
| 5,836,941 A | 11/1998 | Yoshihara et al. | |
| 5,898,058 A | 4/1999 | Nichols | |
| 5,939,320 A | 8/1999 | Littman et al. | |
| 6,056,738 A | 5/2000 | Marchitto et al. | |
| 6,057,114 A | 5/2000 | Akong | |

(Continued)

FOREIGN PATENT DOCUMENTS

| | | | |
|---|---|---|---|
| CN | 1079464 A | | 12/1993 |
| CN | 1558222 A | | 12/2004 |

(Continued)

OTHER PUBLICATIONS

Williams and Denison Sci. Transl. Med., 5, 177ps6, 1-4 (Year: 2013).*

(Continued)

*Primary Examiner* — Anoop K Singh
(74) *Attorney, Agent, or Firm* — Rudy J. Ng; Pania A. Borden; Bozicevic, Field & Francis LLP

(57) ABSTRACT

Provided herein are methods for the treatment of bladder dysfunction, including detrusor hyperreflexia and detrusor external sphincter dyssynergia, fecal incontinence, and/or sexual dysfunction in an individual via the use of stably expressed light-responsive opsin proteins capable of selective hyperpolarization or depolarization of the neural cells that innervate the muscles responsible for physiologic functioning of urinary bladder, external urinary sphincter, external anal sphincter, and the male and female genitalia.

14 Claims, 4 Drawing Sheets

Specification includes a Sequence Listing.

(56) References Cited

U.S. PATENT DOCUMENTS

| | | |
|---|---|---|
| 6,108,081 A | 8/2000 | Holtom et al. |
| 6,134,474 A | 10/2000 | Fischell et al. |
| 6,161,045 A | 12/2000 | Fischell et al. |
| 6,180,613 B1 | 1/2001 | Kaplitt et al. |
| 6,253,109 B1 | 6/2001 | Gielen |
| 6,289,229 B1 | 9/2001 | Crowley |
| 6,303,362 B1 | 10/2001 | Kay et al. |
| 6,334,846 B1 | 1/2002 | Ishibashi et al. |
| 6,336,904 B1 | 1/2002 | Nikolchev |
| 6,346,101 B1 | 2/2002 | Alfano et al. |
| 6,364,831 B1 | 4/2002 | Crowley |
| 6,377,842 B1 | 4/2002 | Pogue et al. |
| 6,436,708 B1 | 8/2002 | Leone et al. |
| 6,473,639 B1 | 10/2002 | Fischell et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,551,346 B2 | 4/2003 | Crossley |
| 6,567,690 B2 | 5/2003 | Giller et al. |
| 6,597,954 B1 | 7/2003 | Pless et al. |
| 6,609,020 B2 | 8/2003 | Gill |
| 6,615,080 B1 | 9/2003 | Unsworth et al. |
| 6,631,283 B2 | 10/2003 | Storrie et al. |
| 6,632,672 B2 | 10/2003 | Calos |
| 6,647,296 B2 | 11/2003 | Fischell et al. |
| 6,685,656 B1 | 2/2004 | Duarte et al. |
| 6,686,193 B2 | 2/2004 | Maher et al. |
| 6,721,603 B2 | 4/2004 | Zabara et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,808,873 B2 | 10/2004 | Murphy et al. |
| 6,810,285 B2 | 10/2004 | Pless et al. |
| 6,889,085 B2 | 5/2005 | Dawson |
| 6,918,872 B2 | 7/2005 | Yokoi |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et al. |
| 7,220,240 B2 | 5/2007 | Struys et al. |
| 7,298,143 B2 | 11/2007 | Jaermann et al. |
| 7,313,442 B2 | 12/2007 | Velasco et al. |
| 7,603,174 B2 | 10/2009 | De Ridder |
| 7,610,100 B2 | 10/2009 | Jaax et al. |
| 7,613,520 B2 | 11/2009 | De Ridder |
| 7,686,839 B2 | 3/2010 | Parker |
| 7,824,869 B2 | 11/2010 | Hegemann et al. |
| 7,883,536 B1 | 2/2011 | Bendett |
| 7,988,688 B2 | 8/2011 | Webb et al. |
| 8,386,312 B2 | 2/2013 | Pradeep et al. |
| 8,398,692 B2 | 3/2013 | Deisseroth et al. |
| 8,401,609 B2 | 3/2013 | Deisseroth et al. |
| 8,603,790 B2 | 12/2013 | Deisseroth et al. |
| 8,696,722 B2 | 4/2014 | Deisseroth et al. |
| 8,716,447 B2 | 5/2014 | Deisseroth et al. |
| 8,729,040 B2 | 5/2014 | Deisseroth et al. |
| 8,815,582 B2 | 8/2014 | Deisseroth et al. |
| 8,834,546 B2 | 9/2014 | Deisseroth et al. |
| 8,864,805 B2 | 10/2014 | Deisseroth et al. |
| 8,906,360 B2 | 12/2014 | Deisseroth et al. |
| 8,926,959 B2 | 1/2015 | Deisseroth et al. |
| 8,932,562 B2 | 1/2015 | Deisseroth et al. |
| 8,956,363 B2 | 2/2015 | Deisseroth et al. |
| 8,962,589 B2 | 2/2015 | Deisseroth et al. |
| 9,057,734 B2 | 6/2015 | Cohen |
| 9,079,940 B2 | 7/2015 | Deisseroth et al. |
| 9,084,885 B2 | 7/2015 | Deisseroth et al. |
| 9,101,690 B2 | 8/2015 | Deisseroth et al. |
| 9,101,759 B2 * | 8/2015 | Delp .................. A61N 5/0601 |
| 9,175,095 B2 | 11/2015 | Deisseroth et al. |
| 9,187,745 B2 | 11/2015 | Deisseroth et al. |
| 9,238,150 B2 | 1/2016 | Deisseroth et al. |
| 9,249,200 B2 | 2/2016 | Deisseroth et al. |
| 9,249,234 B2 | 2/2016 | Deisseroth et al. |
| 9,271,674 B2 | 3/2016 | Deisseroth et al. |
| 9,274,099 B2 | 3/2016 | Deisseroth et al. |
| 9,278,159 B2 | 3/2016 | Deisseroth et al. |
| 9,309,296 B2 | 4/2016 | Deisseroth et al. |
| 9,340,589 B2 | 5/2016 | Deisseroth et al. |
| 9,359,449 B2 | 6/2016 | Deisseroth et al. |
| 9,421,258 B2 | 8/2016 | Deisseroth et al. |
| 9,458,208 B2 | 10/2016 | Deisseroth et al. |
| 9,522,288 B2 | 12/2016 | Deisseroth et al. |
| 9,604,073 B2 | 3/2017 | Deisseroth et al. |
| 9,636,380 B2 | 5/2017 | Deisseroth et al. |
| 9,850,290 B2 | 12/2017 | Deisseroth et al. |
| 9,968,652 B2 | 5/2018 | Deisseroth et al. |
| 10,064,912 B2 | 9/2018 | Deisseroth et al. |
| 10,071,132 B2 | 9/2018 | Deisseroth et al. |
| 2001/0023346 A1 | 9/2001 | Loeb |
| 2002/0094516 A1 | 7/2002 | Calos et al. |
| 2002/0155173 A1 | 10/2002 | Chopp et al. |
| 2002/0164577 A1 | 11/2002 | Tsien et al. |
| 2002/0190922 A1 | 12/2002 | Tsao |
| 2002/0193327 A1 | 12/2002 | Nemerow et al. |
| 2003/0009103 A1 | 1/2003 | Yuste et al. |
| 2003/0026784 A1 | 2/2003 | Koch et al. |
| 2003/0040080 A1 | 2/2003 | Miesenbock et al. |
| 2003/0050258 A1 | 3/2003 | Calos |
| 2003/0082809 A1 | 5/2003 | Quail et al. |
| 2003/0088060 A1 | 5/2003 | Benjamin et al. |
| 2003/0097122 A1 | 5/2003 | Ganz et al. |
| 2003/0103949 A1 | 6/2003 | Carpenter et al. |
| 2003/0104512 A1 | 6/2003 | Freeman et al. |
| 2003/0125719 A1 | 7/2003 | Furnish |
| 2003/0144650 A1 | 7/2003 | Smith |
| 2003/0204135 A1 | 10/2003 | Bystritsky |
| 2003/0232339 A1 | 12/2003 | Shu et al. |
| 2004/0013645 A1 | 1/2004 | Monahan et al. |
| 2004/0015211 A1 | 1/2004 | Nurmikko et al. |
| 2004/0023203 A1 | 2/2004 | Miesenbock et al. |
| 2004/0034882 A1 | 2/2004 | Vale et al. |
| 2004/0039312 A1 | 2/2004 | Hillstead et al. |
| 2004/0049134 A1 | 3/2004 | Tosaya et al. |
| 2004/0068202 A1 | 4/2004 | Hansson et al. |
| 2004/0073278 A1 | 4/2004 | Pachys |
| 2004/0076613 A1 | 4/2004 | Mazarkis et al. |
| 2004/0122475 A1 | 6/2004 | Myrick et al. |
| 2004/0203152 A1 | 10/2004 | Calos |
| 2004/0216177 A1 | 10/2004 | Jordan et al. |
| 2004/0260367 A1 | 12/2004 | Taboada et al. |
| 2004/0267118 A1 | 12/2004 | Dawson |
| 2005/0020945 A1 | 1/2005 | Tosaya et al. |
| 2005/0027284 A1 | 2/2005 | Lozano et al. |
| 2005/0058987 A1 | 3/2005 | Shi et al. |
| 2005/0088177 A1 | 4/2005 | Schreck et al. |
| 2005/0102708 A1 | 5/2005 | Lecanu et al. |
| 2005/0107753 A1 | 5/2005 | Rezai et al. |
| 2005/0112759 A1 | 5/2005 | Radisic et al. |
| 2005/0119315 A1 | 6/2005 | Fedida et al. |
| 2005/0124897 A1 | 6/2005 | Chopra |
| 2005/0143295 A1 | 6/2005 | Walker et al. |
| 2005/0143790 A1 | 6/2005 | Kipke et al. |
| 2005/0153885 A1 | 7/2005 | Yun et al. |
| 2005/0197679 A1 | 9/2005 | Dawson |
| 2005/0202398 A1 | 9/2005 | Hegemann et al. |
| 2005/0215764 A1 | 9/2005 | Tuszynsb et al. |
| 2005/0240127 A1 | 10/2005 | Seip et al. |
| 2005/0267011 A1 | 12/2005 | Deisseroth et al. |
| 2005/0267454 A1 | 12/2005 | Hissong et al. |
| 2005/0279354 A1 | 12/2005 | Deutsch et al. |
| 2006/0025756 A1 | 2/2006 | Francischelli et al. |
| 2006/0034943 A1 | 2/2006 | Tuszynski |
| 2006/0057192 A1 | 3/2006 | Kane |
| 2006/0057614 A1 | 3/2006 | Heintz |

(56) References Cited

U.S. PATENT DOCUMENTS

| | | |
|---|---|---|
| 2006/0058671 A1 | 3/2006 | Vitek et al. |
| 2006/0058678 A1 | 3/2006 | Vitek et al. |
| 2006/0100679 A1 | 5/2006 | DiMauro et al. |
| 2006/0106543 A1 | 5/2006 | Deco et al. |
| 2006/0129126 A1 | 6/2006 | Kaplitt et al. |
| 2006/0155348 A1 | 7/2006 | de Charms |
| 2006/0161227 A1 | 7/2006 | Walsh et al. |
| 2006/0167500 A1 | 7/2006 | Towe et al. |
| 2006/0179501 A1 | 8/2006 | Chan et al. |
| 2006/0184069 A1 | 8/2006 | Vaitekunas |
| 2006/0190044 A1 | 8/2006 | Libbus et al. |
| 2006/0206172 A1 | 9/2006 | DiMauro et al. |
| 2006/0216689 A1 | 9/2006 | Maher et al. |
| 2006/0236525 A1 | 10/2006 | Sliwa et al. |
| 2006/0241697 A1 | 10/2006 | Libbus et al. |
| 2006/0253177 A1 | 11/2006 | Taboada et al. |
| 2006/0271024 A1 | 11/2006 | Gertner et al. |
| 2007/0027443 A1 | 2/2007 | Rose et al. |
| 2007/0031924 A1 | 2/2007 | Li et al. |
| 2007/0053996 A1 | 3/2007 | Boyden et al. |
| 2007/0054319 A1 | 3/2007 | Boyden et al. |
| 2007/0060915 A1 | 3/2007 | Kucklick |
| 2007/0060984 A1 | 3/2007 | Webb et al. |
| 2007/0135875 A1 | 6/2007 | Demarais et al. |
| 2007/0156180 A1 | 7/2007 | Jaax et al. |
| 2007/0191906 A1 | 8/2007 | Iyer et al. |
| 2007/0196838 A1 | 8/2007 | Chesnut et al. |
| 2007/0197918 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0253995 A1* | 11/2007 | Hildebrand .......... A61K 9/0019 424/422 |
| 2007/0260295 A1 | 11/2007 | Chen et al. |
| 2007/0261127 A1* | 11/2007 | Boyden ............... A61K 31/137 800/18 |
| 2007/0282404 A1 | 12/2007 | Cottrell et al. |
| 2007/0295978 A1 | 12/2007 | Coushaine et al. |
| 2008/0020465 A1 | 1/2008 | Padidam |
| 2008/0027505 A1 | 1/2008 | Levin et al. |
| 2008/0046053 A1 | 1/2008 | Wagner et al. |
| 2008/0033569 A1 | 2/2008 | Ferren et al. |
| 2008/0050770 A1 | 2/2008 | Zhang et al. |
| 2008/0051673 A1 | 2/2008 | Kong et al. |
| 2008/0060088 A1 | 3/2008 | Shin et al. |
| 2008/0065158 A1 | 3/2008 | Ben-Ezra et al. |
| 2008/0065183 A1 | 3/2008 | Whitehurst et al. |
| 2008/0077200 A1 | 3/2008 | Bendett et al. |
| 2008/0085265 A1 | 4/2008 | Schneider et al. |
| 2008/0088258 A1 | 4/2008 | Ng |
| 2008/0103551 A1 | 5/2008 | Masoud et al. |
| 2008/0119421 A1 | 5/2008 | Tuszynsh et al. |
| 2008/0125836 A1 | 5/2008 | Streeter et al. |
| 2008/0167261 A1 | 7/2008 | Sclimenti |
| 2008/0175819 A1 | 7/2008 | Kingsman et al. |
| 2008/0176076 A1 | 7/2008 | Van Veggel et al. |
| 2008/0200749 A1 | 8/2008 | Zheng et al. |
| 2008/0221452 A1 | 9/2008 | Njemanze |
| 2008/0227139 A1 | 9/2008 | Deisseroth et al. |
| 2008/0228244 A1 | 9/2008 | Pakhomov et al. |
| 2008/0262411 A1 | 10/2008 | Dobak |
| 2008/0287821 A1 | 11/2008 | Jung et al. |
| 2008/0290318 A1 | 11/2008 | Van Veggel et al. |
| 2009/0030930 A1 | 1/2009 | Pradeep et al. |
| 2009/0054954 A1 | 2/2009 | Foley et al. |
| 2009/0069261 A1 | 3/2009 | Dodge et al. |
| 2009/0088680 A1 | 4/2009 | Deisseroth et al. |
| 2009/0093403 A1* | 4/2009 | Zhang ............... A01K 67/0333 514/8.1 |
| 2009/0099038 A1 | 4/2009 | Deisseroth et al. |
| 2009/0112133 A1 | 4/2009 | Deisseroth et al. |
| 2009/0118800 A1 | 5/2009 | Deisseroth et al. |
| 2009/0131837 A1 | 5/2009 | Granville |
| 2009/0148861 A1 | 6/2009 | Pegan et al. |
| 2009/0157145 A1 | 6/2009 | Cauller |
| 2009/0254134 A1 | 10/2009 | Nikolov et al. |
| 2009/0268511 A1 | 10/2009 | Birge et al. |
| 2009/0306474 A1 | 12/2009 | Wilson |
| 2009/0319008 A1 | 12/2009 | Mayer |
| 2009/0326603 A1* | 12/2009 | Boggs, II .......... A61N 1/36007 607/41 |
| 2010/0009444 A1 | 1/2010 | Herlitze et al. |
| 2010/0016783 A1 | 1/2010 | Bourke et al. |
| 2010/0021982 A1 | 1/2010 | Herlitze |
| 2010/0145418 A1 | 6/2010 | Zhang et al. |
| 2010/0146645 A1 | 6/2010 | Vasar et al. |
| 2010/0190229 A1 | 7/2010 | Deisseroth et al. |
| 2010/0209352 A1 | 8/2010 | Hultman et al. |
| 2010/0234273 A1 | 9/2010 | Deisseroth et al. |
| 2011/0021970 A1 | 1/2011 | Vo-Dihn et al. |
| 2011/0092800 A1 | 4/2011 | Yoo et al. |
| 2011/0105998 A1 | 5/2011 | Deisseroth et al. |
| 2011/0112463 A1* | 5/2011 | Silver ................. A61K 48/005 604/20 |
| 2011/0125077 A1 | 5/2011 | Denison et al. |
| 2011/0125078 A1 | 5/2011 | Denison et al. |
| 2011/0159562 A1 | 6/2011 | Deisseroth et al. |
| 2011/0165681 A1 | 7/2011 | Boyden et al. |
| 2011/0166632 A1 | 7/2011 | Delp et al. |
| 2011/0224095 A1 | 9/2011 | Zoller et al. |
| 2011/0233046 A1 | 9/2011 | Nikolenko et al. |
| 2011/0301529 A1 | 12/2011 | Deisseroth et al. |
| 2011/0311489 A1 | 12/2011 | Deisseroth et al. |
| 2012/0093772 A1 | 4/2012 | Horsager et al. |
| 2012/0121542 A1 | 5/2012 | Chuong et al. |
| 2012/0165904 A1 | 6/2012 | Deisseroth et al. |
| 2012/0190629 A1 | 7/2012 | Tomita et al. |
| 2012/0253261 A1 | 10/2012 | Poletto et al. |
| 2013/0019325 A1 | 1/2013 | Deisseroth et al. |
| 2013/0030275 A1 | 1/2013 | Seymour et al. |
| 2013/0066402 A1 | 3/2013 | Lin et al. |
| 2013/0089503 A1 | 4/2013 | Deisseroth et al. |
| 2013/0144359 A1 | 6/2013 | Kishawi et al. |
| 2013/0184636 A1* | 7/2013 | Creasey ................ A61N 5/062 604/20 |
| 2013/0284920 A1 | 10/2013 | Deisseroth et al. |
| 2013/0286181 A1 | 10/2013 | Betzig et al. |
| 2013/0288365 A1 | 10/2013 | Deisseroth et al. |
| 2013/0289669 A1 | 10/2013 | Deisseroth et al. |
| 2013/0289675 A1 | 10/2013 | Deisseroth et al. |
| 2013/0296406 A1 | 11/2013 | Deisseroth et al. |
| 2013/0317569 A1 | 11/2013 | Deisseroth et al. |
| 2013/0317575 A1 | 11/2013 | Deisseroth et al. |
| 2013/0330816 A1 | 12/2013 | Deisseroth et al. |
| 2013/0343998 A1 | 12/2013 | Deisseroth et al. |
| 2013/0347137 A1 | 12/2013 | Deisseroth et al. |
| 2014/0082758 A1 | 3/2014 | Deisseroth et al. |
| 2014/0148880 A1 | 5/2014 | Deisseroth et al. |
| 2014/0235826 A1 | 8/2014 | Deisseroth et al. |
| 2014/0271479 A1 | 9/2014 | Lammel et al. |
| 2014/0324133 A1 | 10/2014 | Deisseroth et al. |
| 2015/0040249 A1 | 2/2015 | Deisseroth et al. |
| 2015/0072394 A1 | 3/2015 | Deisseroth et al. |
| 2015/0112411 A1 | 4/2015 | Beckman et al. |
| 2015/0165227 A1 | 6/2015 | Deisseroth et al. |
| 2015/0174244 A1 | 6/2015 | Deisseroth et al. |
| 2015/0217128 A1 | 8/2015 | Deisseroth et al. |
| 2015/0218547 A1 | 8/2015 | Deisseroth et al. |
| 2015/0297719 A1 | 10/2015 | Deisseroth et al. |
| 2016/0002302 A1 | 1/2016 | Deisseroth et al. |
| 2016/0015996 A1 | 1/2016 | Deisseroth et al. |
| 2016/0038764 A1 | 2/2016 | Deisseroth et al. |
| 2016/0045599 A1 | 2/2016 | Deisseroth et al. |

FOREIGN PATENT DOCUMENTS

| | | |
|---|---|---|
| CN | 101288768 A | 10/2008 |
| CN | 102076866 A | 5/2011 |
| CN | 103313752 A | 9/2013 |
| CN | 103476456 A | 12/2013 |
| EP | 1197144 | 4/2002 |
| EP | 1334748 | 8/2003 |
| EP | 1444889 | 8/2004 |

(56) References Cited

FOREIGN PATENT DOCUMENTS

| | | |
|---|---|---|
| EP | 1873566 | 1/2008 |
| JP | 6295350 | 10/1994 |
| JP | H 09505771 A | 6/1997 |
| JP | 2004534508 | 11/2004 |
| JP | 2005034073 A | 2/2005 |
| JP | 2006217866 | 8/2006 |
| JP | 2007530027 A | 11/2007 |
| JP | 2008010422 A | 1/2008 |
| JP | 2010227537 A | 10/2010 |
| JP | 2012508581 | 4/2012 |
| WO | WO 1995/005214 | 2/1995 |
| WO | WO 1996/032076 | 10/1996 |
| WO | WO 2000/027293 | 5/2000 |
| WO | WO 2001/025466 | 4/2001 |
| WO | WO 2003/016486 | 2/2003 |
| WO | WO 2003/040323 | 5/2003 |
| WO | WO 2003/046141 | 6/2003 |
| WO | WO 2003/084994 | 10/2003 |
| WO | WO 2003/102156 | 12/2003 |
| WO | WO 2004/033647 | 4/2004 |
| WO | WO 2005/093429 | 10/2005 |
| WO | WO 2006/103678 | 10/2006 |
| WO | WO 2007/024391 | 3/2007 |
| WO | WO 2007/131180 | 11/2007 |
| WO | WO 2008/014382 | 1/2008 |
| WO | WO 2008/086470 | 7/2008 |
| WO | WO 2008/106694 | 9/2008 |
| WO | WO 2009/025819 | 2/2009 |
| WO | WO 2009/072123 | 6/2009 |
| WO | WO 2009/119782 | 10/2009 |
| WO | WO 2009/131837 | 10/2009 |
| WO | WO 2009/148946 | 12/2009 |
| WO | WO 2010/006049 | 1/2010 |
| WO | WO 2010/011404 | 1/2010 |
| WO | WO-2010006049 A1 * | 1/2010 ........... A61N 5/0601 |
| WO | WO2010009106 | 1/2010 |
| WO | WO 2010/056970 | 5/2010 |
| WO | WO 2010/123993 | 10/2010 |
| WO | WO 2011/005978 | 1/2011 |
| WO | WO 2011/066320 | 6/2011 |
| WO | WO 2011/106783 | 9/2011 |
| WO | WO 2011/116238 | 9/2011 |
| WO | WO-2011116238 A2 * | 9/2011 ......... A01K 67/0271 |
| WO | WO 2011/127088 | 10/2011 |
| WO | WO 2012/032103 | 3/2012 |
| WO | WO2012027358 | 3/2012 |
| WO | WO 2012/061676 | 5/2012 |
| WO | WO 2012/061681 | 5/2012 |
| WO | WO 2012/061684 | 5/2012 |
| WO | WO 2012/061688 | 5/2012 |
| WO | WO 2012/061690 | 5/2012 |
| WO | WO 2012/061741 | 5/2012 |
| WO | WO 2012/061744 | 5/2012 |
| WO | WO 2012/106407 | 8/2012 |
| WO | WO 2012/134704 | 10/2012 |
| WO | WO 2013/003557 | 1/2013 |
| WO | WO 2013/016486 | 1/2013 |
| WO | WO 2013/090356 | 6/2013 |
| WO | WO 2013/126521 | 8/2013 |
| WO | WO 2013/126762 | 8/2013 |
| WO | WO 2013/142196 | 9/2013 |
| WO | WO 2014/081449 | 5/2014 |
| WO | WO 2014/117079 | 7/2014 |
| WO | WO 2015/148974 | 10/2015 |
| WO | WO 2016/019075 | 2/2016 |
| WO | WO 2016/090172 | 6/2016 |
| WO | WO 2017/087542 | 5/2017 |

OTHER PUBLICATIONS

Kaiser Science, 317, 580 (Year: 2007).*
Kay et al Nature Reviews Genetics12, 316-328, (Year: 2011).*
Soofiyani et al Advanced Pharmaceutical Bulletin, 3(2), 249-255 (Year: 2013).*
De Palma Hum Gene Ther. 14(12): 1193-206 (Year: 2003).*
Gradinaru et al The Journal of Neuroscience, 27(52):14231-14238 (Year: 2007).*
Skolnick et al Trends in Biotech, 18, 34-39 (Year: 2000).*
Lanyi et al. . Biol. Chem., vol. 265(3), 1253-1260), (Year: 1990).*
Hofherr et al. Journal of Cell Science, vol. 118, 1935-1943 (Year: 2005).*
Vodusek et al Digestion 69:87-92 (Year: 2004).*
Bibel, et al.; "Differentiation of mouse embryonic stem cells into a defined neuronal lineage"; Nature Neuroscience; vol. 7, No. 9, pp. 1033-1009 (Sep. 2004).
Daniel, et al.; "Stress Modulation of Opposing Circuits in the Bed Nucleus of the Stria Terminalis"; Neuropsychopharmacology Reviews; vol. 41, pp. 103-125 (2016).
Hammack, et al.; "The response of neurons in the bed nucleus of the stria terminalis to serotonin Implications for anxiety"; Progress in Neuro-Psychopharmacology & Biological Psychiatry; vol. 33, pp. 1309-1320 (2009).
Knopfel, et al.; "Remote control of cells"; Nature Nanotechnology; vol. 5, pp. 560-561 (Aug. 2010).
Steimer; "The biology of fear- and anxiety-related behaviors"; Dialogues in Clinical Neuroscience; vol. 4, No. 3, pp. 231-249 (Sep. 2002).
Stuber; "Dissecting the neural circuitry of addiction and psychiatric disease with optogenetics"; Neuropsychopharmacology; vol. 35, No. 1, pp. 341-342 (2010).
Abbott, et al.; "Photostimulation of Retrotrapezoid Nucleus Phox2b-Expressing Neurons in Vivo Produces Long-Lasting Activation of Breathing in Rats"; The Journal of Neuroscience; vol. 29, No. 18, pp. 5806-5819 (May 6, 2009).
Alilain, et al.; "Light-Induced Rescue of Breathing after Spinal Cord Injury"; The Journal of Neuroscience; vol. 28, No. 46, pp. 11862-11870 (Nov. 12, 2008).
Cardin, et al.; "Targeted optogenetic stimulation and recording of neurons in vivo using cell-type-specific expression of Channelrhodopsin-2"; Nature Protocols; vol. 5, No. 2, pp. 247-254 (2010).
Caro, et al.; "Engineering of an Artificial Light-Modulated Potassium Channel"; PLoS One; vol. 7, Issue 8, e43766 (Aug. 2012).
Coleman, et al.; "Assessing Anxiety in Nonhuman Primates"; Ilar Journal; vol. 55, No. 2, pp. 333-346 (2014).
Hagglund, et al.; "Activation of groups of excitatory neurons in the mammalian spinal cord or hindbrain evokes locomotion"; Nature Neuroscience; vol. 13, No. 2, 8 pages (Feb. 2010).
Kleinlogel, et al.; "A gene-fusion strategy for stoichiometric and co-localized expression of light-gated membrane proteins"; Nature Methods; vol. 8, No. 12, pp. 1083-1091 (Dec. 2011).
Kravitz, et al.; "Regulation of parkinsonian motor behaviours by optogenetic control of basal ganglia circuitry"; Nature; vol. 466, No. 622, 8 pages (Jul. 29, 2010).
Luo, et al.; "Synthetic DNA delivery systems"; Nature Biotechnology; vol. 18, pp. 33-37 (Jan. 2000).
Maestripieri, et al.; "A modest proposal: displacement activities as an indicator of emotions in primates"; Anim. Behav.; vol. 44, pp. 967-979 (1992).
Nelson, et al.; "Non-Human Primates: Model Animals for Developmental Psychopathology"; Neuropsychopharmacology; vol. 34, No. 1, pp. 90-105 (Jan. 2009).
Tomita, et al.; "Visual Properties of Transgenic Rats Harboring the Channelrhodopsin-2 Gene Regulated by the Thy-1.2 Promoter"; PLoS One; vol. 4, No. 11, 13 pages (Nov. 2009).
Uniprot Accession No. P02945, integrated into the database on Jul. 21, 1986.
Co-pending U.S. Appl. No. 14/822,552, filed Aug. 10, 2015.
Co-pending U.S. Appl. No. 14/886,763, filed Oct. 19, 2015.
Co-pending U.S. Appl. No. 14/911,405, filed Feb. 26, 2016.
Co-pending U.S. Appl. No. 15/008,214, filed Jan. 27, 2016.
Co-pending U.S. Appl. No. 15/059,159, filed Mar. 2, 2016.
Chow, et al.; "High-performance genetically targetable optical neural silencing by light-driven proton pumps"; Nature; vol. 463, pp. 98-102 (Jan. 7, 2010).
Gong, et al.; "Enhanced Archaerhodopsin Fluorescent Protein Voltage Indicators"; PLOS One; vol. 8, Issue 6, 10 pages (Jun. 2013).

(56) References Cited

OTHER PUBLICATIONS

Han, et al.; "A high-light sensitivity optical neural silencer: development and application to optogenetic control of non-human primate cortex"; Frontiers in Systems Neuroscience; vol. 5, Article 18, pp. 1-8 (Apr. 2011).
Davidson, et al.; "Viral Vectors for Gene Delivery to the Nervous System"; Nature Reviews Neuroscience; vol. 4, pp. 353-364 (May 2003).
Fanselow, et al.; "Why We Think Plasticity Underlying Pavlovian Fear Conditioning Occurs in the Basolateral Amygdala"; Neuron; vol. 23, pp. 229-232 (Jun. 1999).
Rogers, et al.; "Effects of ventral and dorsal CA1 subregional lesions on trace fear conditioning"; Neurobiology of Learning and Memory; vol. 86, pp. 72-81 (2006).
Johnson, et al.; "Differential Biodistribution of Adenoviral Vector in Vivo as Monitored by Bioluminescence Imaging and Quantitative Polymerase Chain Reaction"; Human Gene Therapy; vol. 17, pp. 1262-1269 (Dec. 2006).
Schester, et al.; "Biodistribution of adeno-associated virus serotype 9 (AAV9) vector after intrathecal and intravenous delivery in mouse"; Frontiers in Neuroanatomy; vol. 8, Article 42, pp. 1-41 (Jun. 10, 2014).
Airan, et al.; "Integration of light-controlled neuronal firing and fast circuit imaging"; Current Opinion in Neurobiology; vol. 17, pp. 587-592 (2007).
Cannon, et al.; "Endophenotypes in the Genetic Analyses of Mental Disorders"; Annu. Rev. Clin. Psychol.; vol. 2, pp. 267-290 (2006).
Chamanzar, et al.; "Deep Tissue Targeted Near-infrared Optogenetic Stimulation using Fully Implantable Upconverting Light Bulbs"; 2015 37th Annual International Conference of the IEEE Engineering in Medicine and Biology Society (EMBC), IEEE; doi: 10.1109/EMBC.2015.7318488, pp. 821-824 (Aug. 25, 2015).
Chinta, et al.; "Dopaminergic neurons"; The International Journal of Biochemistry & Cell Biology; vol. 37, pp. 942-946 (2005).
Deonarain; "Ligand-targeted receptor-mediated vectors for gene delivery"; Exp. Opin. Ther. Patents; vol. 8, No. 1, pp. 53-69 (1998).
Edelstein, et al.; "Gene therapy clinical trials worldwide 1989-2004—an overview"; The Journal of Gene Medicine; vol. 6, pp. 597-602 (2004).
Grady, et al.; "Age-Related Reductions in Human Recognition Memory Due to Impaired Encoding"; Science; vol. 269, No. 5221, pp. 218-221 (Jul. 14, 1995).
Hososhima, et al.; "Near-infrared (NIR) up-conversion optogenetics"; Optical Techniques in Neurosurgery, Neurophotonics, and Optogenetics II; vol. 9305, doi: 10.1117/12.2078875, 4 pages (2015).
Johnson-Saliba, et al.; "Gene Therapy: Optimising DNA Delivery to the Nucleus"; Current Drug Targets; vol. 2, pp. 371-399 (2001).
Palu, et al.; "In pursuit of new developments for gene therapy of human diseases"; Journal of Biotechnology; vol. 68, pp. 1-13 (1999).
Petersen, et al.; "Functionally Independent Columns of Rat Somatosensory Barrel Cortex Revealed with Voltage-Sensitive Dye Imaging"; J. of Neuroscience; vol. 21, No. 21, pp. 8435-8446 (Nov. 1, 2011).
Pfeifer, et al.; "Gene Therapy: Promises and Problems"; Annu. Rev. Genomics Hum. Genet.; vol. 2, pp. 177-211 (2001).
Powell, et al.; "Schizophrenia-Relevant Behavioral Testing in Rodent Models: A Uniquely Human Disorder?"; Biol. Psychiatry; vol. 59, pp. 1198-1207 (2006).
Shoji, et al.; "Current Status of Delivery Systems to Improve Target Efficacy of Oligonucleotides"; Current Pharmaceutical Design; vol. 10, pp. 785-796 (2004).
Verma, et al.; "Gene therapy—promises, problems and prospects"; Nature; vol. 389, pp. 239-242 (Sep. 1997).
Wang, et al.; "Simultaneous phase and size control of upconversion nanocrystals through lanthanide doping"; Nature; vol. 463, No. 7284, pp. 1061-1065 (Feb. 25, 2010).
Yajima, et al.; "Effects of bromazepam on responses of mucosal blood flow of the gastrointestinal tract and the gastric motility to stimulation of the amygdala and hypothalamus in conscious cats"; Folia Pharmacol. Japon; vol. 83, No. 3, pp. 237-248 (Mar. 1984). [English abstract translation].
Yamada, Shigeto; "Neurobiological Aspects of Anxiety Disorders"; The Japanese Journal of Psychiatry; vol. 8, No. 6, pp. 525-535 (Nov. 25, 2003). [English translation of introduction and summary].
Azizgolshani, et al.; "Reconstituted plant viral capsids can release genes to mammalian cells"; Virology; vol. 441, No. 1, pp. 12-17 (2013).
Racaniello; "How many viruses on Earth?"; Virology Blog; 6 pages; http://www.virology.ws/2013/09/06/how-many-viruses-on-earth/ (Sep. 6, 2013).
Gritton, et al.; "Optogenetically-evoked cortical cholinergic transients in mice expressing channelrhodopsin-2 (ChR2) in cholinergic neurons"; Society for Neuroscience Abstract Viewer and Itinery Planner & 40th Annual Meeting of the Society-for-Neuroscience; vol. 40, 2 pages (2010).
Sofuoglu, et al.; "Cholinergic Functioning in Stimulant Addiction: Implications for Medications Development"; CNS Drugs; vol. 23, No. 11, pp. 939-952 (Nov. 1, 2009).
Witten, et al.; "Cholinergic interneurons of the nucleus accumbens control local circuit activity and reward behavior"; Society for Neuroscience Abstract Viewer and Itinerary Planner & 40th Annual Meeting of the Society-for-Neuroscience; vol. 40, 2 pages (2010).
Lin, et al.; "Study of the Circuitry of Nucleus Accumbens and its Effect on Addiction by Optogenetic Methods: 964"; Neurosurgery; vol. 67, No. 2, pp. 557 (Aug. 2010).
Tsuchida; "Nervous Control of Micturition"; The Japanese Journal of Urology; vol. 80, No. 9, pp. 1257-1277 (1989).
Definition of integral. Merriam-Webster Dictionary, retrieved on Mar. 20, 2017; Retrieved from the internet: <http://www.merriam-webster.com/dictionary/integral>.
Gerits, et al.; "Optogenetically Induced Behavioral and Functional Network Changes in Primates"; Current Biology; vol. 22, pp. 1722-1726 (Sep. 25, 2012).
Han, et al.; "Optogenetics in the nonhuman primate"; Prog. Brain Res.; vol. 196, pp. 215-233 (2012).
Definition of Implant; Merriam-Webster Dictionary; retrieved Nov. 7, 2016 (http://www.merriam-webster.com/dictionary/implant).
Ferenczi, et al.; "Optogenetic approaches addressing extracellular modulation of neural excitability"; Scientific Reports; vol. 6, 20 pages (Apr. 5, 2016).
Li, et al.; "A Method for Activation of Endogenous Acid-sensing Ion Channel 1a (ASIC1a) in the Nervous System with High Spatial and Temporal Precision"; The Journal of Biological Chemistry; vol. 289, No. 22, pp. 15441-15448 (May 30, 2014).
Shimizu, et al.; "NMDA Receptor-Dependent Synaptic Reinforcement as a Crucial Process for Memory Consolidation"; Science; vol. 290, pp. 1170-1174 (Nov. 10, 2000).
Zeng, et al.; "Activation of acid-sensing ion channels by localized proton transient reveals their role in proton signaling"; Scientific Reports; vol. 5, 14 pages (Sep. 15, 2015).
Zeng, et al.; "Proton production, regulation and pathophysiological roles in the mammalian brain"; Neuroscience Bulletin; vol. 28, No. 1, pp. 1-13 (Feb. 1, 2012).
Jones, et al.; "Animal Models of Schizophrenia"; British Journal of Pharmacology; vol. 164, pp. 1162-1194 (2011).
Adamantidis, et al., "Optogenetic Interrogation of Dopaminergic Modulation of the Multiple Phases of Reward-Seeking Behavior", J. Neurosci, 2011, vol. 31, No. 30, pp. 10829-10835.
Aebischer, et al. "Long-Term Cross-Species Brain Transplantation of a Polymer-Encapsulated Dopamine-Secreting Cell Line", Experimental Neurology, 1991, vol. 111, pp. 269-275.
Ageta-Ishihara et al., "Chronic overload of SEPT4, a parkin substrate that aggregates in Parkinson's disease, cause behavioral alterations but not neurodegeneration in mice", Molecular Brain, 2013, vol. 6, 14 pages.
Ahmad, et al. "The *Drosophila* rhodopsin cytoplasmic tail domain is required for maintenance of rhabdomere structure." The FASEB Journal, 2007, vol. 21, p. 449-455.
Airan, et al., "Temporally Precise in vivo Control of Intracellular Signaling", 2009, Nature, vol. 458, No. 7241, pp. 1025-1029.

(56) References Cited

OTHER PUBLICATIONS

Akirav, et al. "The role of the medial prefrontal cortex-amygdala circuit in stress effects on the extinction of fear", Neural Plasticity, 2007: vol. 2007 Article ID:30873, pp. 1-11.
Ali; "Gene and stem cell therapy for retinal disorders"; vision-research.en—The Gateway to European Vision Research; accessed from http://www.vision-research.eu/index.php?id=696, 10 pages (accessed Jul. 24, 2015).
Ang, et at. "Hippocampal CA1 Circuitry Dynamically Gates Direct Cortical Inputs Preferentially at Theta Frequencies." The Journal of Neurosurgery, 2005, vol. 25, No. 42, pp. 9567-9580.
Araki, et al. "Site-Directed Integration of the cre Gene Mediated by Cre Recombinase Using a Combination of Mutant lox Sites", Nucleic Acids Research, 2002, vol. 30, No. 19, pp. 1-8.
Aravanis, et al. "An optical neural interface: in vivo control of rodent motor cortex with integrated fiberoptic and optogenetic technology," J. Neural. Eng., 2007, vol. 4(3):S143-S156.
Arenkiel, et al. "In vivo light-induced activation of neural circuitry in transgenic mice expressing Channelrhodopsin-2", Neuron, 2007, 54:205-218.
Argos, et al. "The integrase family of site-specific recombinases: regional similarities and global diversity", The EMBO Journal, 1986, vol. 5, No. 2, pp. 433-440.
Asano, et al.; "Optically Controlled Contraction of Photosensitive Skeletal Muscle Cells"; Biotechnology & Bioengineering; vol. 109, No. 1, pp. 199-204 (Jan. 2012).
Axoclamp-28 Microelectrode claim theory and operation. Accessed from https://physics.ucsd.edu/neurophysics/Manuals/Axon%20Instruments/Axoclamp-2B_Manual.pdf on Dec. 12, 2014.
Babin et al., "Zebrafish Models of Human Motor Neuron Diseases: Advantages and Limitations", Progress in Neurobiology (2014), 118:36-58.
Balint et al., "The Nitrate Transporting Photochemical Reaction Cycle of the Pharanois Halorhodopsin", Biophysical Journal, 2004, 86:1655-1663.
Bamberg et al. "Light-driven proton or chloride pumping by halorhodopsin." Proc. Natl. Academy Science USA, 1993, vol. 90, No. 2, p. 639-643.
Banghart, et al. "Light-activated ion channels for remote control of neuronal firing". Nature Neuroscience, 2004, vol. 7, No. 12 pp. 1381-1386.
Barchet, et al.; "Challenges and opportunities in CNS delivery of therapeutics for neurodegenerative diseases"; Expert Opinion on Drug Delivery; vol. 6, No. 3, pp. 211-225 (Mar. 16, 2009).
Basil et al.; "Is There Evidence for Effectiveness of Transcranial Magnetic Stimulation in the Treatment of Psychiatric Disorders?"; Psychiatry; vol. 1, No. 11, pp. 64-69 (Nov. 2005).
Bebbington et al., "The use of vectors based on gene amplification for the expression of cloned genes in mammalian cells in DNA cloning" vol. 3, Academic Press, New York, 1987.
Benabid "Future strategies to restore brain functions," Conference proceedings from Medicine Meets Millennium: World Congress of Medicine and Health, 2000, 6 pages.
Benoist et al. "In vivo sequence requirements of the SV40 early promotor region" Nature (London), 1981, vol. 290(5804): pp. 304-310.
Berges et al., "Transduction of Brain by Herpes Simplex Virus Vectors", Molecular Therapy, 2007, vol. 15, No. 1: pp. 20-29.
Berke, et al. "Addiction, Dopamine, and the Molecular Mechanisms of Memory", Molecular Plasticity, 2000, vol. 25: pp. 515-532.
Berlanga, et a.; "Cholinergic Interneurons of the Nucleus Accumbens and Dorsal Striatum are Activated by the Self-Administration of Cocaine"; Neuroscience; vol. 120, pp. 1149-1156 (2003).
Berndt et al. "Bi-stable neural state switches", Nature Neuroscience, 2008, vol. 12, No. 2: pp. 229-234.
Berndt et al., "Structure-guided transformation of channelrhodopsin into a light-activated chloride channel", Science, 2014, 344:420-424.
Berridge et al., "The Versatility and Universality of Calcium Signaling", Nature Reviews: Molecular Cell Biology, 2000, vol. 1: pp. 11-21.
Bi, et al. "Ectopic Expression of a Microbial-Type Rhodopsin Restores Visual Responses in Mice with Photoreceptor Degeneration", Neuron, 2006, vol. 50, No. 1: pp. 23-33.
Bi, et al. "Synaptic Modifications in Cultured Hippocampal Neurons: Dependence on Spike Timing, Synaptic Strength, and Post-synaptic Cell Type", Journal of Neuroscience, 1998, vol. 18, No. 24: pp. 10464-10472.
Blomer et al., "Highly Efficient and Sustained Gene Transfer in Adult Neurons with Lentivirus Vector", Journal of Virology, 1997, vol. 71, No. 9: pp. 6641-6649.
Bocquet et al. "A prokaryotic proton-gated ion channel from the nicotinic acetylcholine receptor family." Nature Letters, 2007, vol. 445, p. 116-119.
Bowers, et al.; "Genetic therapy for the nervous system"; Human Molecular Genetics; vol. 20, No. 1, pp. R28-R41 (2011).
Boyden, et al. "Millisecond-timescale, genetically targeted optical control of neural activity" Nature Neuroscience, 2005, vol. 8, No. 9: pp. 1263-1268.
Braun, "Two Light-activated Conductances in the Eye of the Green Alga Volvox carteri", 1999, Biophys J., vol. 76, No. 3, pp. 1668-1678.
Brewin; "The Nature and Significance of Memory Disturbance in Posttraumatic Stress Disorder"; Ann. Rev. Clin. Psychol.; vol. 7, pp. 203-227 (2011).
Brinton, et al. "Preclinical analyses of the therapeutic potential of allopregnanolone to promote neurogenesis in vitro and in vivo in transgenic mouse model of Alzheimer's disease." Current Alzheimer Research, 2006, vol. 3, No. 1: pp. 11-17.
Brosenitsch et al, "Physiological Patterns of Electrical Stimulation Can Induce Neuronal Gene Expression by Activating N-Type Calcium Channels," Journal of Neuroscience, 2001, vol. 21, No. 8, pp. 2571-2579.
Brown, et al. "Long-term potentiation induced by 9 frequency stimulation is regulated by a protein phosphate-operated gate." The Journal of Neuroscience, 2000, vol. 20, No. 21, pp. 7880-7887.
Bruegmann, et al.; "Optogenetic control of heart muscle in vitro and in vivo"; Nature Methods; vol. 7, No. 11, pp. 897-900(Nov. 2010).
Bruegmann, et al.; "Optogenetics in cardiovascular research: a new tool for light-induced depolarization of cardiomyocytes and vascular smooth muscle cells in vitro and in vivo"; European Heart Journal; vol. 32, No. Suppl . 1, p. 997 (Aug. 2011).
Callaway, et al. "Photostimulation using caged glutamate reveals functional circuitry in living brain slices", Proc. Natl. Acad. Sci. USA., 1993, vol. 90: pp. 7661-7665.
Campagnola et al. "Fiber-coupled light-emitting diode for localized photostimulation of neurons expressing channelrhodopsin-2." Journal of Neuroscience Methods , 2008, vol. 169, Issue 1. Abstract only.
Cardin, et al. "Driving Fast spiking Cells Induces Gamma Rhythm and Controls Sensory Responses", 2009, Nature, vol. 459, vol. 7247, pp. 663-667.
Castagne, et al.; "Rodent Models of Depression: Forced Swim and Tail Suspension Behavioral Despair Tests in Rats and Mice"; Current Protocols in Pharmacology; Supp. 49, Unit 5.8.1-5.8.14 (Jun. 2010).
Cazillis, et al., "VIP and PACAP induce selective neuronal differentiation of mouse embryonic stem cells", Eur J Neurosci, 2004, 19(4):798-808.
Cenatiempo "Prokaryotic gene expression in vitro: transcription-translation coupled systems", Biochimie, 1986, vol. 68(4): pp. 505-515.
Chow et al., "Optogenetics and translation medicine", Sci Transl Med., 2013, 5(177):177.
Clark, et al.; "A future for transgenic livestock"; Nature Reviews Genetics; vol. 4, No. 10, pp. 825-833 (Oct. 2003).
Claudio et al. "Nucleotide and deduced amino acid sequences of Torpedo californica acetylcholine receptor gamma subunit." PNAS USA,1983, vol. 80, p. 1111-1115.
Collingridge et al. "Inhibitory post-synaptic currents in rat hippocampal CA1 neurones." J. Physiol., 1984, vol. 356, pp. 551-564.

(56) References Cited

OTHER PUBLICATIONS

Covington, et al. "Antidepressant Effect of Optogenetic Stimulation of the Medial Prefrontal Cortex." Journal of Neuroscience, 2010, vol. 30(48), pp. 16082-16090.

Cowan et al., "Targeting gene expression to endothelium in transgenic animals: a comparison of the human ICAM-2, PECAM-1, and endoglin promoters", Xenotransplantation, 2003, vol. 10, pp. 223-231.

Crouse, et al. "Expression and amplification of engineered mouse dihydrofolate reductase minigenes" Mol. Cell. Biol., 1983, vol. 3(2): pp. 257-266.

Cucchiaro et al., "Electron-Microscopic Analysis of Synaptic Input from the Perigeniculate Nucleus to A-Laminae of the Lateral Geniculate Nucleus in Cats", The Journal of Comparitive Neurology, 1991, vol. 310, pp. 316-336.

Cucchiaro et al., "Phaseolus vulgaris leucoagglutinin (PHA-L): a neuroanatomical tracer for electron microscopic analysis of synaptic circuitry in the cat's dorsal lateral geniculate nucleus" J. Electron. Microsc. Tech., 1990, 15 (4):352-368.

Cui, et al., "Electrochemical deposition and characterization of conducting polymer polypyrrole/PSS on multichannel neural probes," Sensors and Actuators, 2001, vol. 93(1): pp. 8-18.

Dalva, et al. "Rearrangements of Synaptic Connections in Visual Cortex Revealed by Laser Photostimulation", Science, 1994,vol. 265, pp. 255-258.

Date, et al. "Grafting of Encapsulated Dopamine-Secreting Cells in Parkinson's Disease: Long-Term Primate Study", Cell Transplant, 2000, vol. 9, pp. 705-709.

Davis; "The many faces of epidermal growth factor repeats," The New Biologist; vol. 2, No. 5, pp. 410-419 (1990).

Day, et al.; "The Nucleus Accumbens and Pavlovian Reward Learning"; Neuroscientist; vol. 13, No. 2, pp. 148-159 (Apr. 2007).

De Foubert et al. "Fluoxetine-Induced Change in Rat Brain Expression of Brain-Derived Neurotrophic Factor Varies Depending on Length of Treatment," Neuroscience, 2004, vol. 128, pp. 597-604.

De Palma, et al.; "In Vivo Targeting of Tumor Endothelial Cells by Systemic Delivery of Lentiviral Vectors"; Human Gene Therapy; vol. 14, pp. 1193-1206 (Aug. 10, 2003).

Dederen, et al. "Retrograde neuronal tracing with cholera toxin B subunit: comparison of three different visualization methods", Histochemical Journal, 1994, vol. 26, pp. 856-862.

Definition of Psychosis (2015).

Deisseroth "Next-generation optical technologies for illuminating genetically targeted brain circuits," The Journal of Neuroscience, 2006, vol. 26, No. 41, pp. 10380-10386.

Deisseroth et al., "Excitation-neurogenesis Coupling in Adult Neural Stem/Progenitor Cells", 2004, Neuron, vol. 42, pp. 535-552.

Deisseroth et al., "Signaling from Synapse to Nucleus: Postsynaptic CREB Phosphorylation During Multiple Forms of Hippocampal Synaptic Plasticity", Neuron, 1996, vol. 16, pp. 89-101.

Deisseroth et al., "Signaling from Synapse to Nucleus: the logic Behind the Mechanisms", Currrent Opinion in Neurobiology, 2003, vol. 13, pp. 354-365.

Deisseroth et al., "Translocation of Calmodulin to the Nucleus Supports CREB Phosphorylation in Hippocampal Neurons", Nature, 1998, vol. 392, pp. 198-202.

Deisseroth, et al., "Controlling the Brain with Light", Scientific American, 2010, vol. 303, pp. 48-55.

Delaney et al., "Evidence for a long-lived 13-cis-containing intermediate in the photocyle of the leu 93 → ala bacteriorhodopsin mutant", J. Physical Chemistry B, 1997, vol. 101, No. 29, pp. 5619-5621.

Denk, W., et al. "Anatomical and functional imaging of neurons using 2-photon laser scanning microscopy", Journal of Neuroscience Methods, 1994, vol. 54, pp. 151-162.

Ditterich, et al. "Microstimulation of visual cortex affects the speed of perceptual decisions", 2003, Nature Neuroscience, vol. 6, No. 8, pp. 891-898.

Dittgen, et al. "Lentivirus-based genetic manipulations of cortical neurons and their optical and electrophysiological monitoring in vivo", PNAS, 2004, vol. 101, No. 52, pp. 18206-18211.

Do Carmo, et al.; "Modeling Alzheimer's disease in transgenic rats"; Molecular Neurodegeneration; vol. 8, No. 37, 11 pages (2013).

Douglass, et al., "Escape Behavior Elicited by Single, Channelrhodopsin-2-evoked Spikes in Zebrafish Somatosensory Neurons", Curr Biol., 2008, vol. 18, No. 15, pp. 1133-1137.

Ebert et al., "A Moloney MLV-rat somatotropin fusion gene produces biologically active somatotropin in a transgenic pig", Mol. Endocrinology, 1988, vol. 2, pp. 277-283.

EBI accession No. EMBL: J05199; "N. pharaonis halorhodopsin (hop) gene, complete cds"; (Nov. 22, 1990).

EBI accession No. UNIPROT: A7U0Y6; "SubName: Full= Bacteriorhodopsin"; (Aug. 10, 2010).

EBI accession No. UNIPROT: B0R5N9; "Subname: Full= Bacteriorhodopsin"; (Apr. 8, 2008).

EBI accession No. UNIPROT: B4Y103; "SubName: Full= Channelrhodopsin-1"; (Sep. 23, 2008).

EBI accession No. UNIPROT: P15647; "RecName: Full= Halorhodopsin; Short=HR; Alt Name: Full=NpHR"; (Apr. 1, 1990).

Ehrlich I. et al. "Amygdala inhibitory circuits and the control of fear memory", Neuron, 2009, vol. 62: pp. 757-771.

Eijkelkamp, et al. "Neurological perspectives on voltage-gated sodium channels", Brain, 2012, 135:2585-2612.

Eisen, "Treatment of amyotrophic lateral sclerosis", Drugs Aging, 1999; vol. 14, No. 3, pp. 173-196.

Emerich, et al. "A Novel Approach to Neural Transplantation in Parkinson's Disease: Use of Polymer-Encapsulated Cell Therapy", Neuroscience and Biobehavioral Reviews, 1992, vol. 16, pp. 437-447.

Ensell, et al. "Silicon-based microelectrodes for neurophysiology, micromachined from silicon-on-insulator wafers," Med. Biol. Eng. Comput., 2000, vol. 38, pp. 175-179.

Ernst, et al. "Photoactivation of Channelrhodopsin", J. Biol. Chem., 2008, vol. 283, No. 3, pp. 1637-1643.

Esposito et al. "The integrase family of tyrosine recombinases: evolution of a conserved active site domain", Nucleic Acids Research, 1997, vol. 25, No. 18, pp. 3605-3614.

Evanko "Optical excitation yin and yang" Nature Methods, 2007, 4:384.

Fabian et al. "Transneuronal transport of lectins" Brain Research, 1985, vol. 344, pp. 41-48.

Falconer et al. "High-throughput screening for ion channel modulators," Journal of Biomolecular Screening, 2002, vol. 7, No. 5, pp. 460-465.

Farber, et al. "Identification of Presynaptic Neurons by Laser Photostimulation", Science, 1983, vol. 222, pp. 1025-1027.

Feng, et al. "Imaging Neuronal Subsets in Transgenic Mice Expressing Multiple Spectral Variants of GFP", Neuron, 2000, vol. 28, pp. 41-51.

Fenno et al., "The development and application of optogenetics", Annual Review of Neuroscience, 2011, vol. 34, No. 1, pp. 389-412.

Fiala et al., "Optogenetic approaches in neuroscience", Current Biology, Oct. 2010, 20(20):R897-R903.

Fisher, J. et al. "Spatiotemporal Activity Patterns During Respiratory Rhythmogenesis in the Rat Ventrolateral Medulla," The Journal of Neurophysiol, 2006, vol. 95, pp. 1982-1991.

Fitzsimons et al., "Promotors and Regulatory Elements that Improve Adeno-Associated Virus Transgene Expression in the Brain", 2002, Methods, vol. 28, pp. 227-236.

Foster, "Bright blue times", Nature, 2005, vol. 433, pp. 698-699.

Fox et al., "A gene neuron expression fingerprint of C. elegans embryonic motor neurons", BMC Genomics, 2005, 6(42):1-23.

Friedman, et al.; "Programmed Acute Electrical Stimulation of Ventral Tegmental Area Alleviates Depressive-Like Behavior"; Neuropsychopharmacology; vol. 34, pp. 1057-1066 (2009).

Garrido et al., "A targeting motif involved in sodium channel clustering at the axonal initial segment", Science, 2003, vol. 300, No. 5628, pp. 2091-2094.

(56) References Cited

OTHER PUBLICATIONS

Gelvich et al. "Contact flexible microstrip applicators (CFMA) in a range from microwaves up to short waves," IEEE Transactions on Biomedical Engineering, 2002, vol. 49, Issue 9: 1015-1023.
Genbank Accession No. AAG01180.1; Idnurrn, et al.; pp. 1 (Mar. 21, 2001).
Genbank Accession No. ABT17417.1; Sharma, et al.; pp. 1 (Aug. 15, 2007).
GenBank Accession No. AC096118.6; Rattus norvegicus clone CH230-11 B15, 1-4, 24-25, Working Draft Sequence, 3 unordered pieces. May 10, 2003.
Genbank Accession No. BAA09452.1; Mukohata et al.; pp. 1 (Feb. 10, 1999).
Genbank Accession No. DQ094781 (Jan. 15, 2008).
GenBank Accession No. U79717.1; Rattus norvegicus dopamine 02 receptor 1-4, 24-25 gene, promoter region and exon 1. Jan. 31, 1997.
Gigg, et al. "Glutamatergic hippocampal formation projections to prefrontal cortex in the rat are regulated by GABAergic inhibition and show convergence with glutamatergic projections from the limbic thalamus," Hippocampus, 1994, vol. 4, No. 2, pp. 189-198.
Gilman, et al. "Isolation of sigma-28-specific promoters from *Bacillus subtilis* DNA" Gene, 1984, vol. 32(1-2): pp. 11-20.
Glick et al."Factors affecting the expression of foreign proteins in *Escherichia coli*", Journal of Industrial Microbiology, 1987, vol. 1(5): pp. 277-282.
Goekoop, R. et al. "Cholinergic challenge in Alzheimer patients and mild cognitive impairment differentially affects hippocampal activation—a pharmacological fMRI study." Brain, 2006, vol. 129, pp. 141-157.
Gold, et al. "Representation of a perceptual decision in developing oculomotor commands", Nature, 2000, vol. 404, pp. 390-394.
Gonzalez, et al., "Cell-Based Assays and Instrumentation for Screening Ion-Channel Targets", DDT, 1999, vol. 4, No. 9, pp. 431439.
Gordon, et al. "Regulation of Thy-1 Gene Expression in Transgenic Mice", Cell, 1987, vol. 50, pp. 445-452.
Gorelova et al. , "The course of neural projection from the prefrontal cortex to the nucleus accumbens in the rat", Neuroscience, 1997, vol. 76, No. 3, pp. 689-706.
Goshen et al. "Dynamics of Retrieval Strategies for Remote Memories", Cell, 2011, col. 147: pp. 678-589.
Gottesman et al."Bacterial regulation: global regulatory networks," Ann. Rev. Genet. , 1984, vol. 18, pp. 415-441.
Gradinaru et al., "Optical Deconstruction of Parkinsonian neural circuitry," Science, Apr. 2009, 324(5925):354-359.
Gradinaru et al., "Targeting and readout strategies for fast optical neural control in vitro and in vivo", J Neuroscience, 2007, 27(52):14231-14238.
Gradinaru, et al. "ENpHR: a Natronomonas Halorhodopsin Enhanced for Optogenetic Applications", 2008, Brain Cell Biol., vol. 36 (1-4), pp. 129-139.
Gradinaru, et al., "Molecular and Cellular Approaches for Diversifying and Extending Optogenetics", Cell, 2010, vol. 141, No. 1, pp. 154-165.
Greenberg, et al. "Three-year outcomes in deep brain stimulation for highly resistant obsessive-compulsive disorder," Neuropsychopharmacology, 2006, vol. 31, pp. 2384-2393.
Gregory, et al. "Integration site for *Streptomyces* phage φBT1 and development of site-specific integrating vectors", Journal of Bacteriology, 2003, vol. 185, No. 17, pp. 5320-5323.
Groth et al. "Phage integrases: biology and applications," Journal of Molecular Biology, 2004, vol. 335, pp. 667-678.
Groth, et al. "A phage integrase directs efficient site-specific integration in human cells", PNAS, 2000, vol. 97, No. 11, pp. 5995-6000.
Guatteo, et al. "Temperature sensitivity of dopaminergic neurons of the substantia nigra pars compacta: Involvement of transient receptor potential channels," Journal of Neurophysiol. , 2005, vol. 94, pp. 3069-3080.
Gulick, et al. "Transfection using DEAE-Dextran" Supplement 40, Current Protocols in Molecular Biology, 1997, Supplement 40, 9.2.1-9.2.10.
Gunaydin et al., "Ultrafast optogenetic control", Nature Neuroscience, 2010, vol. 13, No. 3, pp. 387-392.
Gur et al., "A Dissociation Between Brain Activity and Perception: Chromatically Opponent Cortical Neurons Signal Chromatic Flicker that is not Perceived", Vision Research, 1997, vol. 37, No. 4, pp. 377-382.
Haim, et al.; "Gene Therapy to the Nervous System"; Stem Cell and Gene-Based Therapy; Section 2, pp. 133-154 (2006).
Hallet et al. "Transposition and site-specific recombination: adapting DNA cut-and-paste mechanisms to a variety of genetic rearrangements," FEMS Microbiology Reviews, 1997, vol. 21, No. 2, pp. 157-178.
Hamer, et al. "Regulation in Vivo of a cloned mammalian gene: cadmium induces the transcription of a mouse metallothionein gene in SV40 vectors," Journal of Molecular Applied Genetics, 1982, vol. 1, No. 4, pp. 273-288.
Hammer et al., "Spontaneous inflammatory disease in transgenic rats expressing HLA-B27 and Human $\beta_2$m: an animal model of HLA-B27-associated human disorders", Cell, 1990, vol. 63, pp. 1099-1112.
Han, et a.; "Virogenetic and optogenetic mechanisms to define potential therapeutic targets in psychiatric disorders"; Neuropharmacology; vol. 62, pp. 89-100 (2012).
Han, et al., "Millisecond-Timescale Optical Control of Neural Dynamics in the Nonhuman Primate Brain"; Neuron; vol. 62, pp. 191-198 (Apr. 30, 2009).
Han, et al., "Multiple-Color Optical Activation, Silencing, and Desynchronization of Neural Activity with Single-Spike Temporal Resolution", PLoS One, 2007, vol. 2, No. 3, pp. 1-12.
Han; et al., "Two-color, bi-directional optical voltage control of genetically-targeted neurons", CoSyne Abstract Presentation, Presented Feb. 24, 2007.
Hausser, et al. "Tonic Synaptic Inhibition Modulates Neuronal Output Pattern and Spatiotemporal Synaptic Integration", Neuron, 1997, vol. 19, pp. 665-678.
Hegemann et al., "All-trans Retinal Constitutes the Functional Chromophore in *Chlamydomonas* rhodopsin", Biophys. J. , 1991, vol. 60, pp. 1477-1489.
Herlitze, et al., "New Optical Tools for Controlling Neuronal Activity", 2007, Curr Opin Neurobiol, vol. 17, No. 1, pp. 87-94.
Herry, et al. "Switching on and off fear by distinct neuronal circuits," Nature, 2008, vol. 454, pp. 600-606.
Heymann, et al.; "Expression of Bacteriorhodopsin in Sf9 and COS-1 Cells"; Journal of Bioenergetics and Biomembranes; vol. 29, No. 1, pp. 55-59 (1997).
Hikida et al., "Acetylcholine enhancement in the nucleus accumbens prevents addictive behaviors of cocaine and morphine", PNAS, May 2003, 100(10):6169-6173.
Hikida et al., "Increased sensitivity to cocaine by cholingergic cell ablation in nucleus accumbens," PNAS, Nov. 2001, 98(23):13351-13354.
Hildebrandt et al, "Bacteriorhodopsin expressed in *Schizosaccharomyces pombe* pumps protons through the plasma membrane," PNAS, 1993, vol. 90, pp. 3578-3582.
Hira et al., "Transcranial optogenetic stimulation for functional mapping of the motor cortex", J Neurosci Methods, 2009, vol. 179, pp. 258-263.
Hirase, et al. "Multiphoton stimulation of neurons", J Neurobiol, 2002, vol. 51, No. 3: pp. 237-247.
Hodaie, et al., "Chronic Anterior Thalamus Stimulation for Intractable Epilepsy," Epilepsia, 2002, vol. 43, pp. 603-608.
Hoffman et al., "K+ Channel Regulation of Signal Propagation in Dendrites of Hippocampal Pyramidal Neurons", 1997, Nature, vol. 387: pp. 869-874.
Hofherr et al. "Selective Golgi export of Kir2.1 controls the stoichiometry of functional Kir2.x channel heteromers" Journal of Cell Science, 2005, vol. 118, p. 1935-1943.
Hosokawa, T. et al. "Imaging spatia-temporal patterns of long-term potentiation in mouse hippocampus." Philos. Trans. R. Soc. Lond. B., 2003, vol. 358, pp. 689-693.

(56) References Cited

OTHER PUBLICATIONS

Hustler; et al., "Acetylcholinesterase staining in human auditory and language cortices: regional variation of structural features", Cereb Cortex (Mar.-Apr. 1996), 6(2):260-70.
Hynynen, et al. "Clinical applications of focused ultrasound—The brain." Int. J. Hyperthermia, 2007, vol. 23, No. 2: pp. 193-202.
Ibbini, et al.; "A Field Conjugation Method for Direct Synthesis of Hyperthermia Phased-Array Heating Patterns"; IEEE Transactions on Ultrasonics, Ferroelectrics, and Frequency Control; vol. 36, No. 1, pp. 3-9 (Jan. 1989).
Ihara, et al.; "Evolution of the Archaeal Rhodopsins: Evolution Rate Changes by Gene Duplication and Functional Differentiation"; J. Mol. Biol.; vol. 285, pp. 163-174 (1999).
International Search Report for International Application No. PCT/US2009/053474, dated Oct. 8, 2009.
Isenberg et al.; "Cloning of a Putative Neuronal Nicotinic Aceylcholine Receptor Subunit"; Journal of Neurochemistry; vol. 52, No. 3, pp. 988-991 (1989).
Iyer et al., "Virally mediated optogenetic excitation and inhibition of pain in freely moving nontransgenic mice", Nat Biotechnol., 2014, 32(3):274-8.
Jekely, "Evolution of Phototaxis", 2009, Phil. Trans. R. Soc. B, vol. 364, pp. 2795-2808.
Jennings et al., "Distinct extended amygdala circuits for divergent motivational states," Nature, 2013, 496:224-228.
Ji et al., "Light-evoked Somatosensory Perception of Transgenic Rats that Express Channelrhodopsin-2 in Dorsal Root Ganglion Cells", PLoS One, 2012 7(3):e32699.
Jimenez S.A & Maren S. et al/ "Nuclear disconnection within the amygdala reveals a direct pathway to fear", Learning Memory, 2009, vol. 16: pp. 766-768.
Johansen, et al., "Optical Activation of Lateral Amygdala Pyramidal Cells Instructs Associative Fear Learning", 2010, PNAS, vol. 107, No. 28, pp. 12692-12697.
Johnston et al. "Isolation of the yeast regulatory gene *GAL4* and analysis of its dosage effects on the galactose/melibiose regulon," PNAS, 1982, vol. 79, pp. 6971-6975.
Kaiser; "Clinical research. Death prompts a review of gene therapy vector"; Science; 317(5838):580, 1 page (Aug. 3, 2007).
Kandel, E.R.,et al. "Electrophysiology of Hippocampal Neurons: I. Sequential Invasion and Synaptic Organization," J Neurophysiol, 1961, vol. 24, pp. 225-242.
Kandel, E.R.,et al. "Electrophysiology of Hippocampal Neurons: II. After-Potentials and Repetitive Firing", J Neurophysiol., 1961, vol. 24, pp. 243-259.
Karra, et al. "Transfection Techniques for Neuronal Cells", The Journal of Neuroscience, 2010, vol. 30, No. 18, pp. 6171-6177.
Karreman et al. "On the use of double FLP recognition targets (FRTs) in the LTR of retroviruses for the construction of high producer cell lines", Nucleic Acids Research, 1996, vol. 24, No. 9: pp. 1616-1624.
Kato et al. "Present and future status of noninvasive selective deep heating using RF in hyperthermia." Med & Biol. Eng. & Comput 31 Supp: S2-11, 1993. Abstract p. S2 only.
Katz, et al. "Scanning laser photostimulation: a new approach for analyzing brain circuits," Journal of Neuroscience Methods, 1994, vol. 54, pp. 205-218.
Kay; "State-of-the-art gene-based therapies: the road ahead"; Nature Reviews Genetics; vol. 12, pp. 316-328 (May 2011).
Kelder et al., "Glycoconjugates in human and transgenic animal milk", Advances in Exp. Med. and Biol., 2001, vol. 501, pp. 269-278.
Kessler, et al.; "Gene delivery to skeletal muscle results in sustained expression and systemic delivery of a therapeutic protein"; Proc. Natl. Acad. Sci. USA; vol. 93, pp. 14082-14087 (Nov. 1996).
Khodakaramian, et al. "Expression of Cre Recombinase during Transient Phage Infection Permits Efficient Marker Removal in *Streptomyces*," Nucleic Acids Research, 2006, vol. 34, No. 3:e20, pp. 1-5.

Khosravani et al., "Voltage-Gated Calcium Channels and Idiopathic Generalized Epilepsies", Physiol. Rev., 2006, vol. 86: pp. 941-966.
Kianianmomeni, et al. "Channelrhodopsins of Volvox carted are Photochromic Proteins that are Specifically Expressed in Somatic Cells under Control of Light, Temperature, and the Sex Inducer", 2009, Plant Physiology, vol. 151, No. 1, pp. 347-366.
Kim et al., "Diverging neural pathways assemble a behavioural state from separable features in anxiety" Nature, 2013, 496(7444):219-23.
Kim et al., "Light-Driven Activation of β2-Adrenergic Receptor Signaling by a Chimeric Rhodopsin Containing the β2-Adrenergic Receptor Cytoplasmic Loops," Biochemistry, 2005, vol. 44, No. 7, pp. 2284-2292.
Kim et al., "PDZ domain proteins of synapses", Nature Reviews Neuroscience, 2004, vol. 5, No. 10, pp. 771-781.
Kingston et al. "Transfection and Expression of Cloned DNA," Supplement 31, Current Protocols in Immunology, 1999, 10.13.1-10.13.9.
Kingston et al. "Transfection of DNA into Eukaryotic Cells," Supplement 63, Current Protocols in Molecular Biology, 1996, 9.1.1-9.1.11, 11 pages.
Kinoshita, et al., "Optogenetically Induced Supression of Neural Activity in the Macaque Motor Cortex", Poster Sessions Somatomotor System, Others, Society for Neuroscience Meeting, 2010, pp. 141-154.
Kita, H. et al. "Effects of dopamine agonists and antagonists on optical responses evoked in rat frontal cortex slices after stimulation of the subcortical white matter," Exp. Brain Research, 1999, vol. 125, pp. 383-388.
Kitabatake et al., "Impairment of reward-related learning by cholinergic cell ablationn in the striatum", PNAS, Jun. 2003, 100(13):7965-7970.
Kitayama, et al. "Regulation of neuronal differentiation by N-methyl-D-aspartate receptors expressed in neural progenitor cells isolated from adult mouse hippocampus," Journal of Neurosci Research, 2004, vol. 76, No. 5: pp. 599-612.
Klausberger, et al. "Brain-state- and cell-type-specific firing of hippocampal interneurons in vivo", Nature, 2003, vol. 421: pp. 844-848.
Knopfel, et al. "Optical Probing of Neuronal Circuit Dynamics: Gentically Encoded Versus Classical Fluorescent Sensors", 2006, Trends Neurosci, vol. 29, No. 3, pp. 160-166.
Knopfel, et al.; "A comprehensive concept of optogenetics"; Progress in Brain Research; vol. 196, pp. 1-28 (2012).
Kocsis et al., "Regenerating Mammalian Nerve Fibres: Changes in Action Potential Wavefrom and Firing Characteristics Following Blockage of Potassium Conductance", 1982, Proc. R. Soc. Lond., vol. B 217: pp. 77-87.
Kokel et al., "Photochemical activation of TRPA1 channels in neurons and animals", Nat Chem Biol, 2013, 9(4):257-263.
Kuhlman et al. (2008) "High-Resolution Labeling and Functional Manipulation of Specific Neuron Types in Mouse Brain by Cre-Activated Viral Gene Expression" PLoS One, e2005, vol. 3, No. 4, pp. 1-11.
Kunkler, P. et at. "Optical Current Source Density Analysis in Hippocampal Organotypic Culture Shows that Spreading Depression Occurs with Uniquely Reversing Current," The Journal of Neuroscience, 2005, vol. 25, No. 15, pp. 3952-3961.
Lalumiere, R., "A new technique for controlling the brain: optogenetics and its potential for use in research and the clinic", Brain Stimulation, 2011, vol. 4, pp. 1-6.
Lammel et al., "Input-specific control of reward and aversion in the ventral tegmental area", Nature, 2012, 491(7423):212-217.
Landy, A. "Mechanistic and structural complexity in the site-specific recombination pathways of Int And Flp", Current Opinion in Genetics and Development, 1993, vol. 3, pp. 699-707.
Lanyi et al. "The primary structure of a Halorhodopsin from Natronobacterium Pharaonis" Journal of Biological Chemistry, 1990, vol. 265, No. 3, p. 1253-1260.
Lee et al. "Sterotactic Injection of Adenoviral Vectors that Target Gene Expression to Specific Pituitary Cell Types: Implications for Gene Therapy", Neurosurgery, 2000, vol. 46, No. 6: pp. 1461-1469.

(56) References Cited

OTHER PUBLICATIONS

Lee et al., "Potassium Channel Gene Therapy Can Prevent Neuron Death Resulting from Necrotic and Apoptotic Insults", Journal of Neurochemistry, 2003, vol. 85: pp. 1079-1088.
Levitan et al. "Surface Expression of Kv1 Voltage-Gated K+ Channels is Governed by a C-terminal Motif," Trends Cardiovasc. Med., 2000, vol. 10, No. 7, pp. 317-320.
Li et al. "Fast noninvasive activation and inhibition of neural and network activity by vertebrate rhodopsin and green algae channelrhodopsin." PNAS, 2005, vol. 102, No. 49, p. 17816-17821.
Li et al., "Surface Expression of Kv1 Channels is Governed by a C-Terminal Motif", J. Biol. Chem. (2000), 275(16):11597-11602.
Lim et al., "A Novel Targeting Signal for Proximal Clustering of the Kv2.1K+ Channel in Hippocampal Neurons", Neuron, 2000, vol. 25: pp. 385-397.
Lima, et al. "Remote Control of Behavior through Genetically Targeted Photostimulation of Neurons", Cell, 2005, vol. 121: pp. 141-152.
Liman, et al. "Subunit Stoichiometry of a Mammalian K+ Channel Determined by Construction of Multimeric cDNAs," Neuron, 1992,vol. 9, pp. 861-871.
Lin, "A user's guide to char nelrhodopsin variants: features, limitations and future developments", Exp Physiol, 2010, vol. 96, No. 1, pp. 19-25.
Liske et al., "Optical inhibition of motor nerve and muscle activity in vivo", Muscle Nerve, 2013, 47(6):916-21.
Liu et al., "Optogenetics 3.0", Cell, Apr. 2010, 141(1):22-24.
Llewellyn et al., "Orderly recruitment of motor units under optical control in vivo", Nat Med., 2010, 16(10):1161-5.
Loetterle, et al., "Cerebellar Stimulation: Pacing the Brain", American Journal of Nursing, 1975, vol. 75, No. 6, pp. 958-960.
Lonnerberg et al. "Regulatory Region in Choline Acetyltransferase Gene Directs Developmental and Tissue-Specific Expression in Transgenic mice", Proc. Natl. Acad. Sci. USA (1995), 92(9):4046-4050.
Louis et al. "Cloning and sequencing of the cellular-viral junctions from the human adenovirus type 5 transformed 293 cell line," Virology, 1997, vol. 233, pp. 423-429.
Luecke, et al. "Structural Changes in Bacteriorhodopsin During Ion Transport at 2 Angstrom Resolution," Science, 1999, vol. 286, pp. 255-260.
Lyznik, et al. "FLP-mediated recombination of *FRT* sites in the maize genome," Nucleic Acids Research , 1996, vol. 24, No. 19: pp. 3784-3789.
Ma et al. "Role of ER Export Signals in Controlling Surface Potassium Channel Numbers," Science, 2001, vol. 291, pp. 316-319.
Malin et al., "Involvement of the rostral anterior cingulate cortex in consolidation of inhibitory avoidance memory: Interaction with the basolateral amygdala", Neurobiol Learn Mem., Feb. 2007, 87(2):295-302.
Mancuso et al., "Optogenetic probing of functional brain circuitry", Experimental Physiology, 2010, vol. 96.1, pp. 26-33.
Mann et at. "Perisomatic Feedback Inhibition Underlies Cholinergically Induced Fast Network Oscillations in the Rat Hippocampus in Vitro," Neuron, 2005, vol. 45, 2005, pp. 105-117.
Mann; "Synapses"; The Nervous System in Action; Chapter 13, http://michaeldmann.net/mann13.html (downloaded Apr. 2014).
Marin, et al., The Amino Terminus of the Fourth Cytoplasmic Loop of Rhodopsin Modulates Rhodopsin-Transduction Interaction, The Journal of Biological Chemistry, 2000, vol. 275, pp. 1930-1936.
Mattis et al., "Principles for applying optogenetic tools derived from direct comparative analysis of microbial opsins", Nat Methods, 2011, 9(2):159-72.
Mattson, "Apoptosis in Neurodegenerative Disorders", Nature Reviews, 2000, vol. 1: pp. 120-129.
Mayberg et al. "Deep Brain Stimulation for Treatment-Resistant Depression," Focus, 2008, vol. VI, No. 1, pp. 143-154.
Mayford et al., "Control of memory formation through regulated expression of CaMKII transgene", Science, Dec. 1996, 274(5293):1678-1683.
McAllister, "Cellular and Molecular Mechanisms of Dendrite Growth", 2000, Cereb Cortex, vol. 10, No. 10, pp. 963-973.
McKnight "Functional relationships between transcriptional control signals of the thymidine kinase gene of herpes simplex virus", Cell, 1982, vol. 31 pp. 355-365.
Melyan, Z., et al. "Addition of human melanopsin renders mammalian cells Photoresponsive", Nature, 2005, vol. 433: pp. 741-745.
Mermelstein, et al. "Critical Dependence of cAMP Response Element-Binding Protein Phosphorylation on L-Type Calcium Channels Supports a Selective Response to EPSPs in Preference to Action Potentials", The Journal of Neuroscience, 2000, vol. 20, No. 1, pp. 266-273.
Meyer, et al. "High density interconnects and flexible hybrid assemblies for active biomedical implants," IEEE Transactions on Advanced Packaging , 2001, vol. 24, No. 3, pp. 366-372.
Milella et al. "Opposite roles of dopamine and orexin in quinpirole-induced excessive drinking: a rat model of psychotic polydipsia" Psychopharmacology, 2010, 211:355-366.
Monje et al., "Irradiation Induces Neural Precursor-Cell Dysfunction", Natural Medicine, 2002, vol. 8, No. 9, pp. 955-962.
Morelli et al., "Neuronal and glial cell type-specific promoters within adenovirus recombinants restrict the expression of the apoptosis-inducing molecule Fas ligand to predetermined brain cell types, and abolish peripheral liver toxicity", Journal of General Virology, 1999, 80:571-583.
Mortensen et al. "Selection of Transfected Mammalian Cells," Supplement 86, Current Protocols in Molecular Biology, 1997, 9.5.1-09.5.19.
Mourot et al., "Rapid Optical Control of Nociception with an Ion Channel Photoswitch", Nat Methods, 2012, 9(4):396-402.
Mueller, et al.; "Clinical Gene Therapy Using Recombinant Adeno-Associated Virus Vectors"; Gene Therapy; vol. 15, pp. 858-863 (2008).
Mullins et al., "Expression of the DBA/2J Ren-2 gene in the adrenal gland of transgenic mice", EMBO, 1989, vol. 8, pp. 4065-4072.
Mullins et al., "Fulminant hypertension in transgenic rats harbouring the mouse Ren-2 gene", Nature, 1990, vol. 344, pp. 541-544.
Nacher, et al. "NMDA receptor antagonist treatment increases the production of new neurons in the aged rat hippocampus", Neurobiology of Aging, 2003,vol. 24, No. 2: pp. 273-284.
Nagel et al."Functional Expression of Bacteriorhodopsin in Oocytes Allows Direct Measurement of Voltage Dependence of Light Induced H+ Pumping," FEBS Letters, 1995, vol. 377, pp. 263-266.
Nagel, et al. "Channelrhodopsin-l: a light-gated proton channel in green algae", Science, 2002, vol. 296: pp. 2395-2398.
Nagel, et al. "Channelrhodopsin-2, a directly light-gated cation-selective membrane channel", PNAS, 2003, vol. 100, No. 24: pp. 13940-13945.
Nakagami, et al. "Optical Recording of Trisynaptic Pathway in Rat Hippocampal Slices with a Voltage-Sensitive Dye" Neuroscience, 1997, vol. 81, No. 1, pp. 1-8.
Naqvi, et al. "Damage to the insula disrupts addiction to cigarette smoking," Science; 2007, vol. 315 pp. 531-534.
Natochin, et al. "Probing rhodopsin-transducin interaction using *Drosophila* Rh1-bovine rhodopsin chimeras," Vision Res., 2006, vol. 46, No. 27: pp. 4575-4581.
Nieh et al., "Optogenetic dissection of neural circuits underlying emotional valence and motivated behaviors", Brain Research, E-pub 2012, 1511:73-92.
Nirenberg, et al. "The Light Response of Retinal Ganglion Cells is Truncated by a Displaced Amacrine Circuit", Neuron, 1997, vol. 18: pp. 637-650.
No Authors Listed; "Two bright new faces in gene therapy," Nature Biotechnology, 1996, vol. 14: p. 556.
Nonet, "Visualization of synaptic specializations in live C. elegans with synaptic vesicle protein-GFP fusions", J. Neurosci. Methods, 1999, 89:33-40.
Nunes-Duby, et al. "Similarities and differences among 105 members of the Int family of site-specific recombinases" , Nucleic Acids Research, 1998, vol. 26, No. 2: pp. 391-406.

(56) References Cited

OTHER PUBLICATIONS

O'Gorman et al. "Recombinase-mediated gene activation and site-specific integration in mammalian cells", Science, 1991, 251(4999): pp. 1351-1355.
Olivares (2001) "Phage R4 integrase mediates site-specific integration in human cells", Gene, 2001, vol. 278, pp. 167-176.
Ory, et al. "A stable human-derived packaging cell line for production of high titer retrovirus/vesicular stomatitis virus G pseudotypes," PNAS, 1996, vol. 93: pp. 11400-11406.
Packer, et al.; "Targeting Neurons and Photons for Optogenetics"; Nature Neuroscience; vol. 16, No. 7, pp. 805-815 (Jul. 2013).
Palmer et al., "Fibroblast Growth Factor-2 Activates a Latent Neurogenic Program in Neural Stem Cells from Diverse Regions of the Adult CNS", The Journal of Neuroscience, 1999, vol. 19, pp. 8487-8497.
Palmer et al., "The Adult Rat Hippocampus Contains Primordial Neural Stem Cells", Molecular and Cellular Neuroscience, 1997, vol. 8, pp. 389-404.
Pan et al. "Functional Expression of a Directly Light-Gated Membrane Channel in Mammalian Retinal Neurons: A Potential Strategy for Restoring Light Sensitivity to the Retina After Photoreceptor Degeneration"; Investigative Opthalmology & Visual Science, 2005, 46 E-Abstract 4631. Abstract only.
Panda, et al. "Illumination of the Melanopsin Signaling Pathway", Science, 2005, vol. 307: pp. 600-604.
Pandya, et al.; "Where in the Brain is Depression?"; Curr. Psychiatry Rep.; vol. 14, pp. 634-642 (2012).
Pape, et al., "Plastic Synaptic Networks of the Amygdala for the Acquisition, Expression, and Extinction of Conditioned Fear", 2010, Physiol Rev, vol. 90, pp. 419-463.
Paulhe et al. "Specific Endoplasmic Reticulum Export Signal Drives Transport of Stem Cell Factor (Kill) to the Cell Surface," The Journal of Biological Chemistry, 2004, vol. 279, No. 53, p. 55545-55555.
Pear "Transient Transfection Methods for Preparation of High-Titer Retroviral Supernatants" Supplement 68, Current Protocols in Molecular Biology, 1996, 9.1 1 .1-9.1 1 .1 8.
Peralvarez-Marin et al., "Inter-helical hydrogen bonds are essential elements for intra-protein signal transduction: The role of Asp115 in bacteriorhodopsin transport function", J. Mol. Biol., 2007, vol. 368, pp. 666-676.
Peterlin, et al. "Optical probing of neuronal circuits with calcium indicators," PNAS, 2000, vol. 97, No. 7: pp. 3619-3624.
Petersen et al. "Spatiotemporal Dynamics of Sensory Responses in Layer 2/3 of Rat Barrel Cortex Measured in Vivo by Voltage-Sensitive Dye Imaging Combined with Whole-Cell Voltage Recordings and Neuron Reconstructions," The Journal of Neuroscience, 2003, vol. 23, No. 3, pp. 1298-1309.
Petrecca, et al. "Localization and Enhanced Current Density of the Kv4.2 Potassium Channel by Interaction with the Actin-Binding Protein Filamin," The Journal of Neuroscience, 2000, vol. 20, No. 23, pp. 8736-8744.
Pettit, et al. "Local Excitatory Circuits in the Intermediate Gray Layer of the Superior Colliculus", J Neurophysiol., 1999, vol. 81, No. 3: pp. 1424-1427.
Pinkham et al., "Neural bases for impaired social cognition in schizophrenia and autism spectrum disorders", Schizophrenia Research, 2008, vol. 99, pp. 164-175.
Potter, "Transfection by Electroporation." Supplement 62, Current Protocols in Molecular Biology, 1996, 9.3.1-9.3.6.
Pouille, et al. "Routing of spike series by dynamic circuits in the hippocampus", Nature, 2004, vol. 429: pp. 717-723.
Qiu et al. "Induction of photosensitivity by heterologous expression of melanopsin", Nature, 2005, vol. 433: pp. 745-749.
Ramalho, et al.; "Mouse genetic corneal disease resulting from transgenic insertional mutagenesis"; Br. J. Ophthalmol.; vol. 88, No. 3, pp. 428-432 (Mar. 2004).
Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, vol. 12, No. 7, pp. 2534-2546.
Randic, et al. "Long-term Potentiation and Long-term Depression of Primary Afferent Neurotransmission in the Rat Spinal Cord", 1993, Journal of Neuroscience, vol. 13, No. 12, pp. 5228-5241.
Raper, et al.; "Fatal systemic inflammatory response syndrome in a ornithine transcarbamylase deficient patient following adenoviral gene transfer." Mol. Genet. Metab.; vol. 80, No. 1-2, pp. 148-158 (Sep.-Oct. 2003).
Rathnasingham et al., "Characterization of implantable microfabricated fluid delivery devices," IEEE Transactions on Biomedical Engineering, 2004, vol. 51, No. 1: pp. 138-145.
Rein, et al., "The Optogenetic (r)evolution", Mol. Genet. Genomics, 2012, vol. 287, No. 2, pp. 95-109.
Remy, et al., "Depression in Parkinson's Disease: Loss of Dopamine and Noradrenaline Innervation in the Limbic System", Brain, 2005, vol. 128 (Pt 6), pp. 1314-1322.
Ristevski; "Making Better Transgenic Models: Conditional, Temporal, and Spatial Approaches"; Molecular Biotechnology; vol. 29, No. 2, pp. 153-163 (Feb. 2005).
Ritter, et al., "Monitoring Light-induced Structural Changes of Channelrhodopsin-2 by UV-Visible and Fourier Transform Infared Spectroscopy", 2008, The Journal of Biological Chemistry, vol. 283, No. 50, pp. 35033-35041.
Rivera et al., "BDNF-Induced TrkB Activation Down-Regulates the K+-CI-cotransporter KCC2 and Impairs Neuronal CI-Extrusion", The Journal of Cell Biology, 2002, vol. 159: pp. 747-752.
Rosenkranz, et al. "The prefrontal cortex regulates lateral amygdala neuronal plasticity and responses to previously conditioned stimuli", J. Neurosci., 2003, vol. 23, No. 35: pp. 11054-11064.
Rousche, et al., "Flexible polyimide-based intracortical electrode arrays with bioactive capability," IEEE Transactions on Biomedical Engineering, 2001, vol. 48, No. 3, pp. 361-371.
Rubinson et at. "A lentivirus-based system to functionally silence genes in primary mammalian cells, stem cells and transgenic mice by RNA interference," Nature Genetics, 2003, vol. 33, p. 401-406.
Rudiger et at. "Specific arginine and threonine residues control anion binding and transport in the light-driven chloride pump halorhodopsin," The EMBO Journal, 1997, vol. 16, No. 13, pp. 3813-3821.
Sajdyk, et al., "Excitatory Amino Acid Receptors in the Basolateral Amygdala Regulate Anxiety Responses in the Social Interaction Test", Brain Research, 1997, vol. 764, pp. 262-264.
Salzman, et al. "Cortical microstimulation influences perceptual judgements of motion direction", Nature, 1990, vol. 346, pp. 174-177.
Samuelson; "Post-traumatic stress disorder and declarative memory functioning: a review"; Dialogues in Clinical Neuroscience; vol. 13, No. 3, pp. 346-351 (2011).
Santana et al., "Can Zebrafish be Used as Animal Model to Study Alzheimer's Disease?" Am. J. Neurodegener. Dis. (2012), 1(1):32-48.
Sato et al. "Role of Anion-binding Sites in cytoplasmic and extracellular channels of *Natronomonas pharaonis* halorhodopsin," Biochemistry, 2005. vol. 44, pp. 4775-4784.
Sauer "Site-specific recombination: developments and applications," Current Opinion in Biotechnology, 1994, vol. 5, No. 5: pp. 521-527.
Schiff, et al. "Behavioral improvements with thalamic stimulation after severe traumatic brain injury," Nature, 2007, vol. 448, pp. 600-604.
Schlaepfer et al. "Deep Brain stimulation to Reward Circuitry Alleviates Anhedonia in Refractory Major Depresion," Neuropsychopharmacology, 2008,vol. 33, pp. 368-377.
Schroll et al., "Light-induced activation of distinct modulatory neurons triggers appetitive or aversive learning in *Drosophila* larvae", Current Biology, Sep. 2006, 16(17):1741-1747.
Sclimenti, et al. "Directed evolution of a recombinase for improved genomic integration at a native human sequence," Nucleic Acids Research, 2001, vol. 29, No. 24: pp. 5044-5051.

(56) References Cited

OTHER PUBLICATIONS

Sheikh et al., "Neurodegenerative Diseases: Multifactorial Conformational Diseases and Their Therapeutic Interventions", Journal of Neurodegenerative Diseases (2013), Article ID 563481:1-8.
Shepherd, et al. "Circuit Analysis of Experience-Dependent Plasticity in the Developing Rat Barrel Cortex", Neuron, 2003, vol. 38: pp. 277-289.
Shibasaki et al., "Effects of body temperature on neural activity in the hippocampus: Regulation of resting membrane potentials by transient receptor potential vanilloid 4," The Journal of Neuroscience, 2007, 27(7):1566-1575.
Sigmund; "Viewpoint: Are Studies in Genetically Altered Mice Out of Control?"; Arterioscler Thromb Vasc Biol.; vol. 20, No. 6, pp. 1425-1429 (Jun. 2000).
Silver, et al. "Amino terminus of the yeast *GAL4* gene product is sufficient for nuclear localization" PNAS, 1984, vol. 81, No. 19: pp. 5951-5955.
Simmons et al. "Localization and function of NK3 subtype Tachykinin receptors of layer pyramidal neurons of the guinea-pig medial prefrontal cortex", Neuroscience, 2008, vol. 156, No. 4: pp. 987-994.
Sineshchekov et al.; "Intramolecular Proton Transfer in Channelrhodopsins"; Biophysical Journal; vol. 104, No. 4, pp. 807-807 (Feb. 2013).
Sineshchekov et al., "Two Rhodopsins Mediate Phototaxis to Low and High Intensity Light in Chlamydomas Reinhardtil", PNAS, 2002, vol. 99, No. 13, pp. 8689-8694.
Singer et al. "Elevated Intrasynaptic Dopamine Release in Tourette's Syndrome Measured by PET," American Journal of Psychiatry, 2002, vol. 159: pp. 1329-1336.
Singer; "Light Switch for Bladder Control"; Technology Review; pp. 1-2 (Sep. 14, 2009).
Skolnick, et al.; "From genes to protein structure and function: novel applications of computational approaches in the genomic era"; Trends Biotechnol; vol. 18, No. 1, pp. 34-39 (Jan. 2000).
Slamovits et al., "A bacterial proteorhodopsin proton pump in marie eukaryotes", Nature Comm, 2011, 2:183.
Slimko et al., "Selective Electrical Silencing of Mammalian Neurons in Vitro by the use of Invertebrate Ligand-Gated Chloride Channels", The Journal of Neuroscience, 2002, vol. 22, No. 17: pp. 7373-7379.
Smith et al. "Diversity in the serine recombinases", Molecular Microbiology, 2002, vol. 44, No. 2: pp. 299-307.
Sohal et al., "Parvalbumin neurons and gamma rhythms enhance cortical circuit performance", Nature, 2009, vol. 459, No. 7247, pp. 698-702.
Song et al. "Differential Effect of Tea on Long-Term Synaptic Modification in Hippocampal CA1 and Dentate Gyrus in vitro." Neurobiology of Learning and Memory, 2001, vol. 76, No. 3, pp. 375-387.
Song, "Genes responsible for native depolarization-activated K+ currents in neurons," Neuroscience Research, 2002, vol. 42, pp. 7-14.
Soofiyani, et al.; "Gene Therapy, Early Promises, Subsequent Problems, and Recent Breakthroughs"; Advanced Pharmaceutical Bulletin; vol. 3, No. 2, pp. 249-255 (2013).
Stark, et al. "Catalysis by site-specific recombinases," Trends Genet, 1992, vol. 8, No. 12: pp. 432-439.
Stockklausner et al. "A sequence motif responsible for ER export and surface expression of Kir2.0 inward rectifier K+ channels," FEBS Letters, 2001, vol. 493, pp. 129-133.
Stoll, et al. "Phage TP901-I site-specific integrase functions in human cells," Journal of Bacteriology, 2002, vol. 184, No. 13: pp. 3657-3663.
Stonehouse, et al.; "Caffeine Regulates Neuronal Expression of the Dopamine 2 Receptor Gene"; Molecular Pharmacology; vol. 64, No. 6, pp. 1463-1473 (2003).
Suzuki et al., "Stable Transgene Expression from HSV Amplicon Vectors in the Brain: Potential Involvement of Immunoregulatory Signals", Molecular Therapy (2008), 16(10):1727-1736.
Swanson, "Lights, Opsins, Action! Optogenetics Brings Complex Neuronal Circuits into Sharper Focus", 2009, The Dana Foundation, [URL: http://www.dana.org/news/features/detail.aspx?id=24236], PDF File, pp. 1-3.
Swiss-Prot_Q2QCJ4, Opsin 1, Oct. 31, 2006, URL: http://www.ncbi.nlm.nig.gov/protein/Q2QCJ4.
Takahashi, et al."Diversion of the Sign of Phototaxis in a *Chlamydomonas reinhardtii* Mutant Incorporated with Retinal and Its Analogs," FEBS Letters, 1992, vol. 314, No. 3, pp. 275-279.
Takahashi, et al., "Induction of Pluripotent Stem Cells from Mouse Embryonic and Adult Fibroblast Cultures by Defined Factors", 2006, Cell, vol. 126, pp. 663-676.
Tam, B. et al., "Identification of an Outer Segment Targeting Signal in the COOH Terminus of Rhodopsin Using Transgenic *Xenopus laevis*", The Journal of Cell Biology, 2000, vol. 151, No. 7, pp. 1369-1380.
Tamai, "Progress in Pathogenesis and Therapeutic Research in Retinitis Pigmentosa and Age Related Macular Degeneration", Nippon Ganka Gakkai Zasshi, Dec. 2004, 108(12):750-769.
Tatarkiewicz, et al. "Reversal of Hyperglycemia in Mice After Subcutaneous Transplantation of Macroencapsulated Islets", Transplantation, 1999, vol. 67, No. 5: pp. 665-671.
Taurog et al., "HLA-B27 in inbred and non-inbred transgenic mice", J. Immunol., 1988, vol. 141, pp. 4020-4023.
Thomas et al., "Progress and Problems with the Use of Viral Vectors for Gene", Nat. Rev. Genet. (2003), 4(5):346-358.
Tønnesen, et al., "Optogenetic Control of Epileptiform Activity", PNAS, 2009, vol. 106, No. 29, pp. 12162-12167.
Tottene et al., "Familial Hemiplegic Migraine Mutations Increase $Ca^{2+}$ Influx Through Single Human $Ca_v2.1$ Current Density in Neurons", PNAS USA, 2002, vol. 99, No. 20: pp. 13284-13289.
Towne et al., "Efficient transduction of non-human primate motor neurons after intramuscular delivery of recombinant AAV serotype 6", Gene Ther., 2010, 17(1):141-6.
Towne et al., "Optogenetic control of targeted peripheral axons in freely moving animals", PLoS One, 2013, 8(8):e72691.
Towne et al., "Recombinant adeno-associated virus serotype 6 (rAAV2/6)-mediated gene transfer to nociceptive neurons through different routes of delivery", Mol Pain, 2009, 5:52.
Tsai, et al., "Phasic Firing in Dopaminergic Neurons in Sufficient for Behavioral Conditioning", Science, 2009, vol. 324, pp. 1080-1084.
Tsau et al. "Distributed Aspects of the Response to Siphon Touch in *Aplysia*: Spread of Stimulus Information and Cross-Correlation Analysis," The Journal of Neuroscience, 1994, vol. 14, No. 7, pp. 4167-4184.
Tye et. al., "Amygdala circuitry mediating reversible and bidirectional control of anxiety", Nature, 2011, vol. 471(7338): pp. 358-362.
Tye et. al., Supplementary Materials: "Amygdala circuitry mediating reversible and bidirectional control of anxiety,", Nature, 2011, vol. 471(7338): pp. 358-362.
Tye, et al. "Optogenetic investigation of neural circuits underlyding brain disease in animal models," Nature Reviews Neuroscience (Mar. 2012), 13(4):251-266.
Ulmanen, et al. "Transcription and translation of foreign genes in *Bacillus subtilis* by the aid of a secretion vector," Journal of Bacteriology, 1985, vol. 162, No. 1: pp. 176-182.
Van Der Linden, "Functional brain imaging and pharmacotherapy in social phobia: single photon emission computed tomography before and after Treatment with the selective serotonin reuptake inhibitor citalopram," Prog Neuro-psychopharmacol Biol Psychiatry, 2000, vol. 24, No. 3: pp. 419-438.
Vanin, et al. "Development of high-titer retroviral producer cell lines by using Cre-mediated recombination," Journal of Virology, 1997, vol. 71, No. 10: pp. 7820-7826.
Varo et al.,"Light-Driven Chloride Ion Transport by Halorhodopsin from Natronobacterium pharaonic. 2. Chloride Release and Uptake, Protein Conformation Change, and Thermodynamics", Biochemistry (1995), 34(44):14500-14507.

(56) References Cited

OTHER PUBLICATIONS

Vetter, et al. "Development of a Microscale Implantable Neural Interface (MINI) Probe System," Proceedings of the 2005 IEEE, Engineering in Medicine and Biology 27th Annual Conference, Shanghai, China, Sep. 1-4, 2005.

Wagner, "Noninvasive Human Brain Stimulation", Annual Rev. Biomed. Eng. 2007. 9:I9.I-19.39.

Wall, "Transgenic livestock: Progress and prospects for the future", Theriogenology, 1996, vol. 45, pp. 57-68.

Wang, et al. "Direct-current Nanogenerator Driven by Ultrasonic Waves," Science, 2007, vol. 316, pp. 102-105.

Wang, et al., "High-speed mapping of synaptic connectivity using photostimulation in Channelrhodopsin-2 transgenic mice", PNAS, 2007, vol. 104, No. 19, pp. 8143-8148.

Wang, et al., "Molecular Determinants Differentiating Photocurrent Properties of Two Channelrhodopsins from Chlamydomonas", 2009, The Journal of Biological Chemistry, vol. 284, No. 9, pp. 5685-5696.

Wang, et al., "Mrgprd-Expressing Polymodal Nociceptive Neurons Innervate Most Known Classes of Substantia Gelatinosa Neurons", J Neurosci, 2009, 29(42):13202-13209.

Wang, et al.; "Laser-evoked synaptic transmission in cultured hippocampal neurons expressing channelrhodopsin-2 delivered by adeno-associated virus"; Journal of Neuroscience Methods; vol. 183, pp. 165-175 (2009).

Ward, et al. "Construction and characterisation of a series of multi-copy promoter-probe plasmid vectors for *Streptomyces* using the aminoglycoside phosphotransferase gene from Tn5 as indicator", 1986, Mol. Gen. Genet., vol. 203: pp. 468-478.

Watson, et al. "Targeted transduction patterns in the mouse brain by lentivirus vectors pseudotyped with VSV, Ebola, Mokola, LCMV, or MuLV envelope proteins," Molecular Therapy, 2002, vol. 5, No. 5, pp. 528-537.

Weick et al. "Interactions with PDZ Proteins are Required for L-Type Calcium Channels to Activate cAMP Response Element-Binding Protein-Dependent Gene Expression," The Journal of Neuroscience, 2003, vol. 23, No. 8, pp. 3446-3456.

Wells et al. "Application of Infrared light for in vivo neural stimulation," Journal of Biomedical Optics, 2005, vol. 10(6), pp. 064003-1-064003-12.

Williams et al., "From optogenetic technologies to neuromodulation therapies", Sci Transl Med., 2013, 5(177):177.

Witten et. al., "Cholinergic Interneurons Control Local Circuit Activity and Cocaine Conditioning", Science, 2010, vol. 330, No. 6011: pp. 1677-1681.

Witten et. al., Supporting Online Material for: "Cholinergic Interneurons Control Local Circuit Activity and Cocaine Conditioning", Science, 2010, vol. 330: 17 pages.

Written opinion of PCT Application No. PCT/US2011/059383 (dated May 9, 2012).

Xiong et al., "Interregional connectivity to primary motor cortex revealed using MRI resting state images", Hum Brain Mapp, 1999, 8(2-3):151-156.

Yamazoe, et al. "Efficient generation of dopaminergic neurons from mouse embryonic stem cells enclosed in hollow fibers", Biomaterials, 2006, vol. 27, pp. 4871-4880.

Yan et al., "Cloning and Characterization of a Human β,β-Carotene-15, 15'-Dioxygenase that is Highly Expressed in the Retinal Pigment Epithelium", Genomics, 2001, vol. 72: pp. 193-202.

Yizhar et al., "Optogenetics in neural systems", Neuron Primer, vol. 71, No. 1, pp. 9-34 (Jul. 14, 2011).

Yizhar et. al., "Neocortical excitation/inhibition balance in information processing and social dysfunction", Nature, 2011, vol. 477, pp. 171-178; and Supplemental Materials; 41 pages.

Yoon, et al., "A micromachined silicon depth probe for multichannel neural recording," IEEE Transactions Biomedical Engineering, 2000, vol. 47, No. 8, pp. 1082-1087.

Yoshimura, et al. "Excitatory cortical neurons form fine-scale functional networks", Nature, 2005, vol. 433: pp. 868-873.

Zacharias et al. "Recent advances in technology for measuring and manipulating cell signals," Current Opinion in Neurobiology, 2000, vol. 10: pp. 416-421.

Zemelman, et al. "Selective Photostimulation of Genetically ChARGed Neurons", Neuron, 2002, vol. 33: pp. 15-22.

Zemelman, et al. "Photochemical gating of heterologous ion channels: Remote control over genetically designated populations of neurons", PNAS, 2003, vol. 100, No. 3: pp. 1352-1357.

Zhang "Multimodal fast optical interrogation of neural circuitry," Nature, 2007, vol. 446, pp. 633-641.

Zhang, et al. "Channelrhodopsin-2 and optical control of excitable cells," Nature Methods,2006, vol. 3, No. 10, pp. 785-792.

Zhang, et al. "Red-Shifted Optogenetic Excitation: a Tool for Fast Neural Control Derived from *Volvox carteri*", Nature Neurosciences, 2008,vol. 11, No. 6, pp. 631-633.

Zhang, et al., "The Microbial Opsin Family of Optogenetic Tools", Cell, 2011, vol. 147, No. 7, pp. 1146-1457.

Zhang, et al.; "Optogenetic interrogation of neural circuits: Technology for probing mammalian brain structures"; Nature Protocols; vol. 5, No. 3, pp. 439-456 (Feb. 18, 2010).

Zhao, et al. "Improved Expression of Halorhodopsin for Light-Induced Silencing of Neuronal Activity", Brain Cell Biology, 2008, vol. 36 (1-4), pp. 141-154.

Zrenner, E., "Will Retinal Implants Restore Vision?" Science, 2002, vol. 295, No. 5557, pp. 1022-1025.

Zufferey, et al. "Self-Inactivating Lentivirus Vector for Safe and Efficient in Vivo Gene Delivery", Journal of Virology, 1998, vol. 72, No. 12, pp. 9873-9880.

Kugler, et al.; "Neuron-Specific Expression of Therapeutic Proteins: Evaluation of Different Cellular Promoters in Recombinant Adenoviral Vectors"; Molecular and Cellular Neuroscience; vol. 17, pp. 78-96 (2001).

Masaki, et al.; "β2-Adrenergic Receptor Regulation of the Cardiac L-Type Ca2+ Channel Coexpressed in a Fibroblast Cell Line"; Receptor; vol. 5, pp. 219-231 (1996).

Smith, et al.; "Proton binding sites involved in the activation of acid-sensing ion channel ASIC2a"; Neuroscience Letters; vol. 426, pp. 12-17 (2007).

Boyden, et al.; "A history of optogenetics: the development of tools for controlling brain circuits with light"; F1000 Biology Reports; vol. 3, No. 11, 12 pages (May 3, 2011).

Knox, et al.; "Heterologous Expression of Limulus Rhodopsin"; The Journal of Biological Chemistry; vol. 278, No. 42, pp. 40493-40502 (Oct. 17, 2003).

Lin, et al.; "Characterization of Engineered Channelrhodopsin Variants with Improved Properties and Kinetics"; Biophysical Journal; vol. 96, No. 5, pp. 1803-1814 (Mar. 2009).

Friedman, et al.; "VTA Dopamine Neuron Bursting is Altered in an Animal Model of Depression and Corrected by Desipramine"; J. Mol. Neurosci.; vol. 34, pp. 201-209 (2008).

Hackmann, et al.; "Static and time-resolved step-scan Fourier transform infrared investigations of the photoreaction of halorhodopsin from Natronobacterium pharaonis: consequences for models of the anion translocation mechanism"; Biophysical Journal; vol. 81, pp. 394-406 (Jul. 2001).

Weiss, et al.; "Galanin: A Significant Role in Depression?"; Annals New York Academy of Sciences; vol. 863, No. 1, pp. 364-382 (1998).

Winter, et al.; "Lesions of dopaminergic neurons in the substantia nigra pars compacta and in the ventral tegmental area enhance depressive-like behavior in rats"; Behavioural Brain Research; vol. 184, pp. 133-141 (2007).

Nargeot et al.; Molecular basis of the diversity of calcium channels in cardiovascular tissues European Heart Journal, 1997, Supplemental A, A15-A26.

Erbguth et al. "Bimodal Activation of Different Neuron Classes with Spectrally Red-Shifted Channelrhodopsin Chimera C1V1 in Caenorhabditis elegans," PLOS One, 2012, vol. 7 No. 10, pp. e46827/1-e46827/9.

Li et al.; "Role of a Helix B Lysine Residue in the Photoactive Site in Channelrhodopsins," Biophysical Journal, 2014, vol. 106, pp. 1607-1617.

(56) References Cited

OTHER PUBLICATIONS

Prigge et al.: "Functional Studies of Volvox Channelrhodopsin Chimeras," Biophysical Journal, 2010, vol. 98, No. 3, Suppl. 1, 3694 Poster, 1 page.

Prigge et al.; Color-tuned Channelrhodopsins for Multiwavelength Optogenetics, J. Biol. Chem. 2012, vol. 287, No. 38, pp. 31804-31812.

Tsunoda & Hegemann "Glu 87 of Channelrhodopsin-1 Causes pH-dependent Color Tuning and Fast Photocurrent Inactivation," Photochemistry and Photobiology, 2009, vol. 85, No. 2, pp. 564-569.

Sharma, et al. "Evolution of rhodosin ion pump in haloarchaea," BMC Evolutionary Biology, 2007, vol. 7, No. 79: pp. 1-13.

Ahmad, et al. "Heterplogous expression of bovine rhodopsin in *Drosophila* photoreceptor cells" Invest Ophthalmol Vis Sci. 2006, 3722-3728.

Clare "Targeting Ion Channels for Drug Discovery" Discov Med. 2010 vol. 9 No. 46 pp. 1-6.

Clare "Functional Expression of Ion Channels in Mammalian Systems" Protein Science Encyclopedia A.R. Fersht (Ed.) 2008 pp. 79-109.

Reeves et al., "Structure and function in rhodosin: A tetracycline-inducible system in stable mammalian cell lines for high-level expression of opsin mutants" PNAS, 2002 vol. 99 No. 21 pp. 13413-13418.

Belzung et al., "Optogenetics to study the circuits of fear- and depresssion-like behaviors: A critical analysis," Pharmacology, Biochemistry and Behavior, 2014, 122: 144-157.

Bernstein & Boyden "Optogenetic tools for analyzing the neural circuits of behavior," Trends Cogn Sci., 2011 15(12): 592-600.

Duvarci, et al., "The bed Nucleaus of the Stria Terminalis Mediates inter-individual variations in anxiety and fear", J. Neurosci., 29(33) 10357-10361 (2009).

Matsuda "Bed nucleus of stria terminalis (BNST)" Benshi Seishin Igaku (Molecular Psychiatric Medicine), 2009, vol. 9 No. 3, p. 46-49.

Neuropsychopharmacology, 2011, vol. 36 No. Suppl.1, p. S110 (Abstract No. 67).

Neuropsychopharmacology, 2012, vol. 38 No. Suppl.1, p. S48 (Abstract No. 37.2).

Walker et al. "Selective Participation of the Bed Nucleus of the Stria Terminalis and CRF in Sustained Anxiety-like versus Phasic Fear-Like Responses," Prog Neuropsychopharmacol Bio Psychiatry, 13: 33(8) 1291-1308 (2009).

\* cited by examiner

Numbers of EUS Pudendal Motor Neurons: Measured vs. Reported

SEQUENCE LISTING

<160> NUMBER OF SEQ ID NOS: 24

<210> SEQ ID NO 1
<211> LENGTH: 273
<212> TYPE: PRT
<213> ORGANISM: Artificial sequence
<220> FEATURE:
<223> OTHER INFORMATION: Synthetic amino acid sequence

<400> SEQUENCE: 1

Val Thr Gln Arg Glu Leu Phe Glu Phe Val Leu Asn Asp Pro Leu Leu
1               5                   10                  15

Ala Ser Ser Leu Tyr Ile Asn Ile Ala Leu Ala Gly Leu Ser Ile Leu
            20                  25                  30

Leu Phe Val Phe Met Thr Arg Gly Leu Asp Asp Pro Arg Ala Lys Leu
        35                  40                  45

Ile Ala Val Ser Thr Ile Leu Val Pro Val Val Ser Ile Ala Ser Tyr
    50                  55                  60

Thr Gly Leu Ala Ser Gly Leu Thr Ile Ser Val Leu Glu Met Pro Ala
65                  70                  75                  80

Gly His Phe Ala Glu Gly Ser Ser Val Met Leu Gly Gly Glu Glu Val
                85                  90                  95

Asp Gly Val Val Thr Met Trp Gly Arg Tyr Leu Thr Trp Ala Leu Ser
            100                 105                 110

Thr Pro Met Ile Leu Leu Ala Leu Gly Leu Leu Ala Gly Ser Asn Ala
        115                 120                 125

Thr Lys Leu Phe Thr Ala Ile Thr Phe Asp Ile Ala Met Cys Val Thr
    130                 135                 140

Gly Leu Ala Ala Ala Leu Thr Thr Ser Ser His Leu Met Arg Trp Phe
145                 150                 155                 160

Trp Tyr Ala Ile Ser Cys Ala Cys Phe Leu Val Val Leu Tyr Ile Leu
                165                 170                 175

Leu Val Glu Trp Ala Gln Asp Ala Lys Ala Ala Gly Thr Ala Asp Met
            180                 185                 190

Phe Asn Thr Leu Lys Leu Leu Thr Val Val Met Trp Leu Gly Tyr Pro
        195                 200                 205

Ile Val Trp Ala Leu Gly Val Glu Gly Ile Ala Val Leu Pro Val Gly
    210                 215                 220

Val Thr Ser Trp Gly Tyr Ser Phe Leu Asp Ile Val Ala Lys Tyr Ile
225                 230                 235                 240

Phe Ala Phe Leu Leu Leu Asn Tyr Leu Thr Ser Asn Glu Ser Val Val
                245                 250                 255

Ser Gly Ser Ile Leu Asp Val Pro Ser Ala Ser Gly Thr Pro Ala Asp
            260                 265                 270

Asp

<210> SEQ ID NO 2
<211> LENGTH: 559
<212> TYPE: PRT
<213> ORGANISM: Artificial sequence
<220> FEATURE:
<223> OTHER INFORMATION: Synthetic amino acid sequence

<400> SEQUENCE: 2

Met Thr Glu Thr Leu Pro Pro Val Thr Glu Ser Ala Val Ala Leu Gln
1               5                   10                  15

Ala Glu Val Thr Gln Arg Glu Leu Phe Glu Phe Val Leu Asn Asp Pro
                20                  25                  30

Leu Leu Ala Ser Ser Leu Tyr Ile Asn Ile Ala Leu Ala Gly Leu Ser
            35                  40                  45

Ile Leu Leu Phe Val Phe Met Thr Arg Gly Leu Asp Asp Pro Arg Ala
        50                  55                  60

Lys Leu Ile Ala Val Ser Thr Ile Leu Val Pro Val Val Ser Ile Ala
65                  70                  75                  80

Ser Tyr Thr Gly Leu Ala Ser Gly Leu Thr Ile Ser Val Leu Glu Met
                85                  90                  95

Pro Ala Gly His Phe Ala Glu Gly Ser Ser Val Met Leu Gly Gly Glu
            100                 105                 110

Glu Val Asp Gly Val Val Thr Met Trp Gly Arg Tyr Leu Thr Trp Ala
        115                 120                 125

Leu Ser Thr Pro Met Ile Leu Ala Leu Gly Leu Ala Gly Ser
130                 135                 140

Asn Ala Thr Lys Leu Phe Thr Ala Ile Thr Phe Asp Ile Ala Met Cys
145                 150                 155                 160

Val Thr Gly Leu Ala Ala Ala Leu Thr Thr Ser Ser His Leu Met Arg
                165                 170                 175

Trp Phe Trp Tyr Ala Ile Ser Cys Ala Cys Phe Leu Val Val Leu Tyr
            180                 185                 190

Ile Leu Leu Val Glu Trp Ala Gln Asp Ala Lys Ala Ala Gly Thr Ala
        195                 200                 205

Asp Met Phe Asn Thr Leu Lys Leu Leu Thr Val Val Met Trp Leu Gly
    210                 215                 220

Tyr Pro Ile Val Trp Ala Leu Gly Val Glu Gly Ile Ala Val Leu Pro
225                 230                 235                 240

Val Gly Val Thr Ser Trp Gly Tyr Ser Phe Leu Asp Ile Val Ala Lys
                245                 250                 255

Tyr Ile Phe Ala Phe Leu Leu Leu Asn Tyr Leu Thr Ser Asn Glu Ser
            260                 265                 270

Val Val Ser Gly Ser Ile Leu Asp Val Pro Ser Ala Ser Gly Thr Pro
        275                 280                 285

Ala Asp Asp Ala Ala Ala Lys Ser Arg Ile Thr Ser Glu Gly Glu Tyr
    290                 295                 300

Ile Pro Leu Asp Gln Ile Asp Ile Asn Val Val Ser Lys Gly Glu Glu
305                 310                 315                 320

Leu Phe Thr Gly Val Val Pro Ile Leu Val Glu Leu Asp Gly Asp Val
                325                 330                 335

Asn Gly His Lys Phe Ser Val Ser Gly Glu Gly Glu Gly Asp Ala Thr
            340                 345                 350

```
Tyr Gly Lys Leu Thr Leu Lys Phe Ile Cys Thr Thr Gly Lys Leu Pro
            355                 360                 365

Val Pro Trp Pro Thr Leu Val Thr Thr Phe Gly Tyr Gly Leu Gln Cys
370                 375                 380

Phe Ala Arg Tyr Pro Asp His Met Lys Gln His Asp Phe Phe Lys Ser
385                 390                 395                 400

Ala Met Pro Glu Gly Tyr Val Gln Glu Arg Thr Ile Phe Phe Lys Asp
            405                 410                 415

Asp Gly Asn Tyr Lys Thr Arg Ala Glu Val Lys Phe Glu Gly Asp Thr
            420                 425                 430

Leu Val Asn Arg Ile Glu Leu Lys Gly Ile Asp Phe Lys Glu Asp Gly
            435                 440                 445

Asn Ile Leu Gly His Lys Leu Glu Tyr Asn Tyr Asn Ser His Asn Val
            450                 455                 460

Tyr Ile Met Ala Asp Lys Gln Lys Asn Gly Ile Lys Val Asn Phe Lys
465                 470                 475                 480

Ile Arg His Asn Ile Glu Asp Gly Ser Val Gln Leu Ala Asp His Tyr
                    485                 490                 495

Gln Gln Asn Thr Pro Ile Gly Asp Gly Pro Val Leu Leu Pro Asp Asn
            500                 505                 510

His Tyr Leu Ser Tyr Gln Ser Ala Leu Ser Lys Asp Pro Asn Glu Lys
            515                 520                 525

Arg Asp His Met Val Leu Leu Glu Phe Val Thr Ala Ala Gly Ile Thr
            530                 535                 540

Leu Gly Met Asp Glu Leu Tyr Lys Phe Cys Tyr Glu Asn Glu Val
545                 550                 555

<210> SEQ ID NO 3
<211> LENGTH: 542
<212> TYPE: PRT
<213> ORGANISM: Artificial sequence
<220> FEATURE:
<223> OTHER INFORMATION: Synthetic amino acid sequence

<400> SEQUENCE: 3

Met Val Thr Gln Arg Glu Leu Phe Glu Phe Val Leu Asn Asp Pro Leu
1               5                   10                  15

Leu Ala Ser Ser Leu Tyr Ile Asn Ile Ala Leu Ala Gly Leu Ser Ile
            20                  25                  30

Leu Leu Phe Val Phe Met Thr Arg Gly Leu Asp Asp Pro Arg Ala Lys
            35                  40                  45

Leu Ile Ala Val Ser Thr Ile Leu Val Pro Val Val Ser Ile Ala Ser
50                  55                  60

Tyr Thr Gly Leu Ala Ser Gly Leu Thr Ile Ser Val Leu Glu Met Pro
65                  70                  75                  80

Ala Gly His Phe Ala Glu Gly Ser Ser Val Met Leu Gly Gly Glu Glu
            85                  90                  95

Val Asp Gly Val Val Thr Met Trp Gly Arg Tyr Leu Thr Trp Ala Leu
            100                 105                 110

Ser Thr Pro Met Ile Leu Leu Ala Leu Gly Leu Leu Ala Gly Ser Asn
            115                 120                 125

Ala Thr Lys Leu Phe Thr Ala Ile Thr Phe Asp Ile Ala Met Cys Val
            130                 135                 140

Thr Gly Leu Ala Ala Ala Leu Thr Thr Ser Ser His Leu Met Arg Trp
145                 150                 155                 160
```

```
Phe Trp Tyr Ala Ile Ser Cys Ala Cys Phe Leu Val Leu Tyr Ile
            165                 170                 175

Leu Leu Val Glu Trp Ala Gln Asp Ala Lys Ala Ala Gly Thr Ala Asp
        180                 185                 190

Met Phe Asn Thr Leu Lys Leu Leu Thr Val Val Met Trp Leu Gly Tyr
        195                 200                 205

Pro Ile Val Trp Ala Leu Gly Val Glu Gly Ile Ala Val Leu Pro Val
    210                 215                 220

Gly Val Thr Ser Trp Gly Tyr Ser Phe Leu Asp Ile Val Ala Lys Tyr
225                 230                 235                 240

Ile Phe Ala Phe Leu Leu Leu Asn Tyr Leu Thr Ser Asn Glu Ser Val
            245                 250                 255

Val Ser Gly Ser Ile Leu Asp Val Pro Ser Ala Ser Gly Thr Pro Ala
        260                 265                 270

Asp Asp Ala Ala Lys Ser Arg Ile Thr Ser Glu Gly Glu Tyr Ile
        275                 280                 285

Pro Leu Asp Gln Ile Asp Ile Asn Val Val Ser Lys Gly Glu Glu Leu
    290                 295                 300

Phe Thr Gly Val Val Pro Ile Leu Val Glu Leu Asp Gly Asp Val Asn
305                 310                 315                 320

Gly His Lys Phe Ser Val Ser Gly Glu Gly Glu Gly Asp Ala Thr Tyr
            325                 330                 335

Gly Lys Leu Thr Leu Lys Phe Ile Cys Thr Thr Gly Lys Leu Pro Val
        340                 345                 350

Pro Trp Pro Thr Leu Val Thr Thr Phe Gly Tyr Gly Leu Gln Cys Phe
    355                 360                 365

Ala Arg Tyr Pro Asp His Met Lys Gln His Asp Phe Phe Lys Ser Ala
370                 375                 380

Met Pro Glu Gly Tyr Val Gln Glu Arg Thr Ile Phe Phe Lys Asp Asp
385                 390                 395                 400

Gly Asn Tyr Lys Thr Arg Ala Glu Val Lys Phe Glu Gly Asp Thr Leu
            405                 410                 415

Val Asn Arg Ile Glu Leu Lys Gly Ile Asp Phe Lys Glu Asp Gly Asn
        420                 425                 430

Ile Leu Gly His Lys Leu Glu Tyr Asn Tyr Asn Ser His Asn Val Tyr
    435                 440                 445

Ile Met Ala Asp Lys Gln Lys Asn Gly Ile Lys Val Asn Phe Lys Ile
450                 455                 460

Arg His Asn Ile Glu Asp Gly Ser Val Gln Leu Ala Asp His Tyr Gln
465                 470                 475                 480

Gln Asn Thr Pro Ile Gly Asp Gly Pro Val Leu Leu Pro Asp Asn His
            485                 490                 495

Tyr Leu Ser Tyr Gln Ser Ala Leu Ser Lys Asp Pro Asn Glu Lys Arg
        500                 505                 510

Asp His Met Val Leu Leu Glu Phe Val Thr Ala Ala Gly Ile Thr Leu
    515                 520                 525

Gly Met Asp Glu Leu Tyr Lys Phe Cys Tyr Glu Asn Glu Val
530                 535                 540

<210> SEQ ID NO 4
<211> LENGTH: 223
<212> TYPE: PRT
<213> ORGANISM: Artificial sequence
<220> FEATURE:
<223> OTHER INFORMATION: Synthetic amino acid sequence
```

```
<400> SEQUENCE: 4

Ala Ser Ser Phe Gly Lys Ala Leu Leu Glu Phe Val Phe Ile Val Phe
1               5                   10                  15

Ala Cys Ile Thr Leu Leu Gly Ile Asn Ala Ala Lys Ser Lys Ala
            20                  25                  30

Ala Ser Arg Val Leu Phe Pro Ala Thr Phe Val Thr Gly Ile Ala Ser
            35                  40                  45

Ile Ala Tyr Phe Ser Met Ala Ser Gly Gly Trp Val Ile Ala Pro
    50                  55                  60

Asp Cys Arg Gln Leu Phe Val Ala Arg Tyr Leu Asp Trp Leu Ile Thr
65                  70                  75                  80

Thr Pro Leu Leu Leu Ile Asp Leu Gly Leu Val Ala Gly Val Ser Arg
                85                  90                  95

Trp Asp Ile Met Ala Leu Cys Leu Ser Asp Val Leu Met Ile Ala Thr
                100                 105                 110

Gly Ala Phe Gly Ser Leu Thr Val Gly Asn Val Lys Trp Val Trp Trp
            115                 120                 125

Phe Phe Gly Met Cys Trp Phe Leu His Ile Ile Phe Ala Leu Gly Lys
    130                 135                 140

Ser Trp Ala Glu Ala Ala Lys Ala Lys Gly Gly Asp Ser Ala Ser Val
145                 150                 155                 160

Tyr Ser Lys Ile Ala Gly Ile Thr Val Ile Thr Trp Phe Cys Tyr Pro
                165                 170                 175

Val Val Trp Val Phe Ala Glu Gly Phe Gly Asn Phe Ser Val Thr Phe
            180                 185                 190

Glu Val Leu Ile Tyr Gly Val Leu Asp Val Ile Ser Lys Ala Val Phe
            195                 200                 205

Gly Leu Ile Leu Met Ser Gly Ala Ala Thr Gly Tyr Glu Ser Ile
    210                 215                 220

<210> SEQ ID NO 5
<211> LENGTH: 310
<212> TYPE: PRT
<213> ORGANISM: Artificial sequence
<220> FEATURE:
<223> OTHER INFORMATION: Synthetic amino acid sequence

<400> SEQUENCE: 5

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
            115                 120                 125
```

Pro Val Ile Leu Ile His Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
                180                 185                 190

Ala Lys Ala Tyr Ile Glu Gly Tyr His Thr Val Pro Lys Gly Arg Cys
                195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
                275                 280                 285

Ile Gly Gly Thr Glu Ile Glu Val Glu Thr Leu Val Glu Asp Glu Ala
290                 295                 300

Glu Ala Gly Ala Val Pro
305                 310

<210> SEQ ID NO 6
<211> LENGTH: 310
<212> TYPE: PRT
<213> ORGANISM: Artificial sequence
<220> FEATURE:
<223> OTHER INFORMATION: Synthetic amino acid sequence

<400> SEQUENCE: 6

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
                20                  25                  30

Gln Cys Tyr Cys Ala Gly Trp Ile Glu Ser Arg Gly Thr Asn Gly Ala
                35                  40                  45

Gln Thr Ala Ser Asn Val Leu Gln Trp Leu Ala Ala Gly Phe Ser Ile
50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
                100                 105                 110

Gly His Arg Val Gln Trp Leu Arg Tyr Ala Glu Trp Leu Leu Thr Ser
                115                 120                 125

Pro Val Ile Leu Ile His Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

```
Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 7
<211> LENGTH: 310
<212> TYPE: PRT
<213> ORGANISM: Artificial sequence
<220> FEATURE:
<223> OTHER INFORMATION: Synthetic amino acid sequence

<400> SEQUENCE: 7

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Ser
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Ala Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220
```

```
Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
            245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
        290                 295                 300

Glu Ala Gly Ala Val Pro
305                 310

<210> SEQ ID NO 8
<211> LENGTH: 344
<212> TYPE: PRT
<213> ORGANISM: Artificial sequence
<220> FEATURE:
<223> OTHER INFORMATION: Synthetic amino acid sequence

<400> SEQUENCE: 8

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
            85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Leu Ile His Leu Ser Asn
            165                 170                 175

Leu Thr Gly Leu Lys Asp Asp Tyr Ser Lys Arg Thr Met Gly Leu Leu
        180                 185                 190

Val Ser Asp Val Gly Cys Ile Val Trp Gly Ala Thr Ser Ala Met Cys
    195                 200                 205

Thr Gly Trp Thr Lys Ile Leu Phe Phe Leu Ile Ser Leu Ser Tyr Gly
210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
            245                 250                 255

Thr Phe Phe Val Ala Trp Gly Met Phe Pro Val Leu Phe Leu Leu Gly
            260                 265                 270
```

```
Thr Glu Gly Phe Gly His Ile Ser Pro Tyr Gly Ser Ala Ile Gly His
            275                 280                 285

Ser Ile Leu Asp Leu Ile Ala Lys Asn Met Trp Gly Val Leu Gly Asn
        290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Asp
            340

<210> SEQ ID NO 9
<211> LENGTH: 344
<212> TYPE: PRT
<213> ORGANISM: Artificial sequence
<220> FEATURE:
<223> OTHER INFORMATION: Synthetic amino acid sequence

<400> SEQUENCE: 9

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Thr Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
        275                 280                 285
```

```
Ser Ile Leu Asp Leu Ile Ala Lys Asn Met Trp Gly Val Leu Gly Asn
    290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Asp
            340

<210> SEQ ID NO 10
<211> LENGTH: 344
<212> TYPE: PRT
<213> ORGANISM: Artificial sequence
<220> FEATURE:
<223> OTHER INFORMATION: Synthetic amino acid sequence

<400> SEQUENCE: 10

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
        50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
130                 135                 140

Ala Val Ile Tyr Ser Ser Asn Gly Asn Lys Thr Val Trp Leu Arg Tyr
145                 150                 155                 160

Ala Thr Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
        275                 280                 285

Ser Ile Leu Asp Leu Ile Ala Lys Asn Met Trp Gly Val Leu Gly Asn
290                 295                 300
```

```
Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340
```

<210> SEQ ID NO 11
<211> LENGTH: 344
<212> TYPE: PRT
<213> ORGANISM: Artificial sequence
<220> FEATURE:
<223> OTHER INFORMATION: Synthetic amino acid sequence

<400> SEQUENCE: 11

```
Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Thr Ile Tyr Val Ala Thr Ile
        115                 120                 125

Glu Met Ile Lys Phe Ile Ile Glu Tyr Phe His Glu Phe Asp Glu Pro
130                 135                 140

Ala Val Ile Tyr Ser Ser Asn Gly Asn Lys Thr Val Trp Leu Arg Tyr
145                 150                 155                 160

Ala Thr Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
        275                 280                 285

Ser Ile Leu Asp Leu Ile Ala Lys Asn Met Trp Gly Val Leu Gly Asn
290                 295                 300

Tyr Leu Arg Val Lys Ile His Glu His Ile Leu Leu Tyr Gly Asp Ile
305                 310                 315                 320
```

Arg Lys Lys Gln Lys Ile Thr Ile Ala Gly Gln Glu Met Glu Val Glu
            325                 330                 335

Thr Leu Val Ala Glu Glu Glu Asp
        340

<210> SEQ ID NO 12
<211> LENGTH: 20
<212> TYPE: PRT
<213> ORGANISM: Artificial sequence
<220> FEATURE:
<223> OTHER INFORMATION: Synthetic amino acid sequence

<400> SEQUENCE: 12

Lys Ser Arg Ile Thr Ser Glu Gly Glu Tyr Ile Pro Leu Asp Gln Ile
1               5                   10                  15

Asp Ile Asn Val
        20

<210> SEQ ID NO 13
<211> LENGTH: 26
<212> TYPE: PRT
<213> ORGANISM: Artificial sequence
<220> FEATURE:
<223> OTHER INFORMATION: Synthetic amino acid sequence

<400> SEQUENCE: 13

Met Asp Tyr Gly Gly Ala Leu Ser Ala Val Gly Arg Glu Leu Leu Phe
1               5                   10                  15

Val Thr Asn Pro Val Val Val Asn Gly Ser
            20                  25

<210> SEQ ID NO 14
<211> LENGTH: 27
<212> TYPE: PRT
<213> ORGANISM: Artificial sequence
<220> FEATURE:
<223> OTHER INFORMATION: Synthetic amino acid sequence

<400> SEQUENCE: 14

Met Ala Gly His Ser Asn Ser Met Ala Leu Phe Ser Phe Ser Leu Leu
1               5                   10                  15

Trp Leu Cys Ser Gly Val Leu Gly Thr Glu Phe
            20                  25

<210> SEQ ID NO 15
<211> LENGTH: 23
<212> TYPE: PRT
<213> ORGANISM: Artificial sequence
<220> FEATURE:
<223> OTHER INFORMATION: Synthetic amino acid sequence

<400> SEQUENCE: 15

Met Gly Leu Arg Ala Leu Met Leu Trp Leu Leu Ala Ala Ala Gly Leu
1               5                   10                  15

Val Arg Glu Ser Leu Gln Gly
            20

<210> SEQ ID NO 16
<211> LENGTH: 18
<212> TYPE: PRT
<213> ORGANISM: Artificial sequence
<220> FEATURE:
<223> OTHER INFORMATION: Synthetic amino acid sequence

<400> SEQUENCE: 16

```
Met Arg Gly Thr Pro Leu Leu Leu Val Val Ser Leu Phe Ser Leu Leu
1               5                   10                  15

Gln Asp
```

<210> SEQ ID NO 17
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 17

```
Val Lys Glu Ser Leu
1               5
```

<210> SEQ ID NO 18
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 18

```
Val Leu Gly Ser Leu
1               5
```

<210> SEQ ID NO 19
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 19

```
Asn Ala Asn Ser Phe Cys Tyr Glu Asn Glu Val Ala Leu Thr Ser Lys
1               5                   10                  15
```

<210> SEQ ID NO 20
<211> LENGTH: 6
<212> TYPE: PRT
<213> ORGANISM: Artificial sequence
<220> FEATURE:
<223> OTHER INFORMATION: Synthetic amino acid sequence
<220> FEATURE:
<221> NAME/KEY: misc_feature
<222> LOCATION: (2)..(2)
<223> OTHER INFORMATION: Xaa can be any amino acid

<400> SEQUENCE: 20

```
Phe Xaa Tyr Glu Asn Glu
1               5
```

<210> SEQ ID NO 21
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 21

```
Phe Cys Tyr Glu Asn Glu Val
1               5
```

<210> SEQ ID NO 22
<211> LENGTH: 18
<212> TYPE: PRT

<213> ORGANISM: Artificial sequence
<220> FEATURE:
<223> OTHER INFORMATION: Synthetic amino acid sequence

<400> SEQUENCE: 22

```
Met Thr Glu Thr Leu Pro Pro Val Thr Glu Ser Ala Val Ala Leu Gln
1               5                   10                  15
Ala Glu
```

<210> SEQ ID NO 23
<211> LENGTH: 258
<212> TYPE: PRT
<213> ORGANISM: Artificial Sequence
<220> FEATURE:
<223> OTHER INFORMATION: Synthetic amino acid sequence

<400> SEQUENCE: 23

```
Met Asp Pro Ile Ala Leu Gln Ala Gly Tyr Asp Leu Leu Gly Asp Gly
1               5                   10                  15
Arg Pro Glu Thr Leu Trp Leu Gly Ile Gly Thr Leu Leu Met Leu Ile
                20                  25                  30
Gly Thr Phe Tyr Phe Leu Val Arg Gly Trp Gly Val Thr Asp Lys Asp
                35                  40                  45
Ala Arg Glu Tyr Tyr Ala Val Thr Ile Leu Val Pro Gly Ile Ala Ser
    50                  55                  60
Ala Ala Tyr Leu Ser Met Phe Phe Gly Ile Gly Leu Thr Glu Val Thr
65                  70                  75                  80
Val Gly Gly Glu Met Leu Asp Ile Tyr Tyr Ala Arg Tyr Ala Asp Trp
                85                  90                  95
Leu Phe Thr Thr Pro Leu Leu Leu Leu Asp Leu Ala Leu Leu Ala Lys
                100                 105                 110
Val Asp Arg Val Thr Ile Gly Thr Leu Val Gly Val Asp Ala Leu Met
                115                 120                 125
Ile Val Thr Gly Leu Ile Gly Ala Leu Ser His Thr Ala Ile Ala Arg
    130                 135                 140
Tyr Ser Trp Trp Leu Phe Ser Thr Ile Cys Met Ile Val Val Leu Tyr
145                 150                 155                 160
Phe Leu Ala Thr Ser Leu Arg Ser Ala Ala Lys Glu Arg Gly Pro Glu
                165                 170                 175
Val Ala Ser Thr Phe Asn Thr Leu Thr Ala Leu Val Leu Val Leu Trp
                180                 185                 190
Thr Ala Tyr Pro Ile Leu Trp Ile Ile Gly Thr Glu Gly Ala Gly Val
                195                 200                 205
Val Gly Leu Gly Ile Glu Thr Leu Leu Phe Met Val Leu Asp Val Thr
    210                 215                 220
Ala Lys Val Gly Phe Gly Phe Ile Leu Leu Arg Ser Arg Ala Ile Leu
225                 230                 235                 240
Gly Asp Thr Glu Ala Pro Glu Pro Ser Ala Gly Ala Asp Val Ser Ala
                245                 250                 255
Ala Asp
```

<210> SEQ ID NO 24
<211> LENGTH: 534
<212> TYPE: PRT
<213> ORGANISM: Artificial Sequence
<220> FEATURE:
<223> OTHER INFORMATION: Synthetic Amino Acid Sequence

<400> SEQUENCE: 24

```
Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Met Leu Ile
            20                  25                  30

Gly Thr Phe Tyr Phe Leu Val Arg Gly Trp Gly Val Thr Asp Lys Asp
            35                  40                  45

Ala Arg Glu Tyr Tyr Ala Val Thr Ile Leu Val Pro Gly Ile Ala Ser
        50                  55                  60

Ala Ala Tyr Leu Ser Met Phe Phe Gly Ile Gly Leu Thr Glu Val Thr
65                  70                  75                  80

Val Gly Gly Glu Met Leu Asp Ile Tyr Tyr Ala Arg Tyr Ala Asp Trp
                85                  90                  95

Leu Phe Thr Thr Pro Leu Leu Leu Leu Asp Leu Ala Leu Leu Ala Lys
            100                 105                 110

Val Asp Arg Val Thr Ile Gly Thr Leu Val Gly Val Asp Ala Leu Met
        115                 120                 125

Ile Val Thr Gly Leu Ile Gly Ala Leu Ser His Thr Ala Ile Ala Arg
130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp Arg Pro Val Val Ala Val Ser Lys Ala Ala Lys Ser Arg
            260                 265                 270

Ile Thr Ser Glu Gly Glu Tyr Ile Pro Leu Asp Gln Ile Asp Ile Asn
        275                 280                 285

Val Val Ser Lys Gly Glu Glu Leu Phe Thr Gly Val Val Pro Ile Leu
290                 295                 300

Val Glu Leu Asp Gly Asp Val Asn Gly His Lys Phe Ser Val Ser Gly
305                 310                 315                 320

Glu Gly Glu Gly Asp Ala Thr Tyr Gly Lys Leu Thr Leu Lys Phe Ile
                325                 330                 335

Cys Thr Thr Gly Lys Leu Pro Val Pro Trp Pro Thr Leu Val Thr Thr
            340                 345                 350

Phe Gly Tyr Gly Leu Gln Cys Phe Ala Arg Tyr Pro Asp His Met Lys
        355                 360                 365

Gln His Asp Phe Phe Lys Ser Ala Met Pro Glu Gly Tyr Val Gln Glu
370                 375                 380

Arg Thr Ile Phe Phe Lys Asp Asp Gly Asn Tyr Lys Thr Arg Ala Glu
385                 390                 395                 400

Val Lys Phe Glu Gly Asp Thr Leu Val Asn Arg Ile Glu Leu Lys Gly
                405                 410                 415
```

```
Ile Asp Phe Lys Glu Asp Gly Asn Ile Leu Gly His Lys Leu Glu Tyr
            420             425             430
Asn Tyr Asn Ser His Asn Val Tyr Ile Met Ala Asp Lys Gln Lys Asn
            435             440             445
Gly Ile Lys Val Asn Phe Lys Ile Arg His Asn Ile Glu Asp Gly Ser
450             455             460
Val Gln Leu Ala Asp His Tyr Gln Gln Asn Thr Pro Ile Gly Asp Gly
465             470             475             480
Pro Val Leu Leu Pro Asp Asn His Tyr Leu Ser Tyr Gln Ser Ala Leu
                485             490             495
Ser Lys Asp Pro Asn Glu Lys Arg Asp His Met Val Leu Leu Glu Phe
            500             505             510
Val Thr Ala Ala Gly Ile Thr Leu Gly Met Asp Glu Leu Tyr Lys Phe
            515             520             525
Cys Tyr Glu Asn Glu Val
            530
```

US 11,103,723 B2

METHODS FOR TREATING NEUROGENIC DISORDERS OF THE PELVIC FLOOR

CROSS-REFERENCE

This application is a continuation of U.S. patent application Ser. No. 13/772,732, filed Feb. 21, 2013, which claims the benefit of U.S. Provisional Patent Application No. 61/601,298, filed Feb. 21, 2012, which applications are incorporated herein by reference in their entirety.

TECHNICAL FIELD

This application pertains to methods for treating neurogenic disorders of the pelvic floor including bladder dysfunction, fecal incontinence, and sexual dysfunction in an individual, via the use of stably expressed light-responsive opsin proteins capable of selectively altering the membrane potential of the neural cells that innervate the muscles and organs responsible for urinary, rectal, and sexual function.

INTRODUCTION

"Optogenetics" refers to the combination of genetic and optical methods used to control specific events in targeted cells of living tissue, even within freely moving mammals and other animals, with the temporal precision (millisecond-timescale) needed to keep pace with functioning intact biological systems. The hallmark of optogenetics is the introduction of fast light-responsive ion channel and/or pump proteins to the plasma membranes of target neuronal cells that allow temporally precise manipulation of neuronal membrane potential while maintaining cell-type resolution through the use of specific targeting mechanisms (See, e.g. U.S. Patent Application Publication Nos. 2007/0054319, 2009/0093403, and 2010/0145418 as well as International Patent Application Publication Nos. WO 2009/131837 and WO 2007/024391). In just a few short years, the field of optogenetics has furthered the fundamental scientific understanding of how specific cell types contribute to the function of biological tissues in vivo, including the interactions between skeletal and smooth muscles with the neurons responsible for their innervation.

Urinary incontinence, the inability to maintain voluntary control of micturition, is a condition that affects millions of men and women worldwide. The control of urination is a complex physiological process including neural reflex pathways, some with and some without central nervous system control, smooth and voluntary muscles, as well as hormonal effects. (See review by DeGroat, 1997, *Urology* 50[Supp6A]:36-52). A large subset of urinary incontinence is at least partly neurogenic. The clinical term "overactive bladder" is used generally to denote any form of incontinence characterized by increased frequency of micturition or desire to void, whether complete or episodic, and where loss of voluntary control ranges from partial to total. "Urge incontinence" is the involuntary loss of urine associated with an abrupt and powerful desire to void. Urge incontinence is often associated with the urodynamic finding of involuntary (uninhibited) contractions of the detrusor muscle, which provides the primary force in expelling urine from the bladder. A large subset of patients with uninhibited detrusor have some sort of neurologic impairment, in which case the clinical term is "detrusor hyperreflexia" (DH). Common neurologic disorders associated with detrusor hyperreflexia (DH) are Parkinson's disease, stroke, diabetes, multiple sclerosis (MS), and peripheral neuropathy. Additionally, individuals who suffer a traumatic injury to the spinal cord commonly experience symptoms associated with DH.

The muscles of the external urinary sphincter may also be affected by spinal cord injuries, resulting in a condition known as "dyssynergia." Dyssynergia involves an inability of urinary sphincter muscles to relax when the bladder contracts, including active contraction in response to bladder voiding, preventing urine from flowing through the urethra and resulting in the incomplete emptying of the bladder and "reflux" of urine into the kidneys.

Some treatments for detrusor hyperreflexia and external urinary sphincter dyssynergia rely on electrical neurostimulation. This treatment modality depends on the use of electrodes positioned adjacent to the nerve/muscle to be stimulated. Activation of the electrode with an electrical pulse excites the adjacent nerve leading to the contraction of muscles innervated by that nerve. However, the electrode is non-selective and will stimulate every tissue and cell type that falls within its electrical field. Thus, current neurostimulatory methods and devices cannot act locally with cell-type specificity to regulate the muscles and the nerves responsible for symptoms associated with detrusor hyperreflexia and external urinary sphincter dyssynergia.

Sacral anterior root stimulation (SARS, Finetech Medical Limited) is a neurostimulatory device used to restore bladder function in patients who have sustained spinal cord injuries. SARS requires a sacral root rhizotomy to prevent DH/DSD, resulting in loss of sexual function. Additionally, sacral root rhizotomy further damages the afferent pathways of the lower urinary tract, leading to bladder areflexia or the loss of bladder contraction. As a result, post-surgical electrical stimulation is needed to activate the detrusor muscle. However, at the same time, the electrode also activates the external urinary sphincter muscle because the nerves innervating the sphincter are larger than those of the detrusor and, therefore, are recruited first. Because the striated muscle of the sphincter relaxes more rapidly than the smooth muscle of the detrusor, an individual who has undergone SARS experiences post-stimulus voiding for a brief period of time. However, in addition to the aforementioned loss of sexual function, SARS often results in very high bladder pressure that can cause near-term vesicoureteral reflux and has been associated, long-term, with renal failure.

Other current treatments for detrusor hyperreflexia and external urinary sphincter dyssynergia include permanent or intermittent self-catheterization combined with anti-muscarinic agents (such as oxybutynin or tolterodine), use of alpha-blockers, injection of the external urinary sphincter with Botulinum Toxin (such as, Botox® (Allergan) or Dysport® (Ipsen)), balloon dilation of the external urinary sphincter, and use of uretheral stents. However, all of these treatments suffer from considerable drawbacks, including the need for frequent repeat treatments (in the case of intermittent catherization and Botulinum Toxin administration), increased urinary tract infections (catheterization, stents, balloon dilation), increased incidence of septicemia (balloon dilation), and increased susceptibility to squamous-cell carcinoma (catheterization).

Another pelvic floor disorder, fecal incontinence, is a condition whereby fecal material is involuntarily excreted or leaked due to decreased bowel control. Fecal incontinence of varying degrees is thought to be a result of any number of factors, including dysfunction of or damage to the anal sphincters, dysfunction of the pelvic floor, or decreased compliance in the rectum. The neural supply to the anorectal region is both somatic and autonomic. The superficial perineal nerve (branch of pudendal nerve) provides sensory fibers to the perineum as well as the anal canal mucosa. The external anal sphincter receives its motor supply from the inferior rectal nerve (a.k.a. inferior hemorrhoidal nerve, a branch of the pudendal nerve). Like treatments for urinary dysfunction, some treatments for fecal incontinence rely on electrical stimulation of the nerves that control the muscles of the anal sphincter and attempt to restore an individual's continence. Other surgical treatments, such as colostomy, are also common. However, all of these methods suffer from considerable practical drawbacks and complications.

Sexual dysfunction comprises a broad range of maladies, including erectile dysfunction, orgasmic dysfunction, premature ejaculation and lack of lubrication. Sexual dysfunctions plague both women and men, and may be life-long or acquired. Sexual dysfunction has a number of causes, both physiological and psychological, and in many patients the disorder may be multifactorial. The causes include several that are essentially neurologic in origin. For example, damage to the pathways used by the autonomic nervous system to innervate the penis and clitoris may interrupt sexual arousal initiated by the central nervous system. Lesions (e.g., injury, infection, or disease) of the somatic nervous pathways (i.e., any of the nerves associated with sensation or motion) may impair reflexogenic sexual function (i.e., involuntary, instinctive physiological response to a stimulus) and may interrupt tactile sensation needed to maintain sexual arousal. Additionally, spinal cord lesions may produce varying degrees of sexual dysfunction depending on the location and severity of the lesions.

Currently, there is no good long acting, cost effective, or clinically meaningful therapy that precisely targets the neural cells and associated muscles/organs responsible for these defects with the potential to bring about more physiologically normal micturition, bowel control, and sexual function in individuals with symptoms associated with neurogenic disorders of the pelvic floor.

Throughout this specification, references are made to publications (e.g., scientific articles), patent applications, patents, etc., all of which are herein incorporated by reference in their entirety.

SUMMARY

Provided herein are methods for the treatment of bladder dysfunction, fecal incontinence, and sexual dysfunction in an individual via the use of stably expressed light-responsive opsin proteins capable of hyperpolarizing or depolarizing the neurons that innervate the muscles of the bladder, the neurons that innervate the external urinary sphincter, the neurons that innervate the external anal sphincter, the neurons that innervate the muscles responsible for the contraction of the rectum, and/or the neurons that innervate the genitalia, wherein the hyperpolarization or depolarization-induced synaptic depletion of the neurons induces the relaxation of the muscle innervated by the neurons, and depolarization of the neurons induces the contraction of the muscle innervated by the neurons. In some embodiments, contraction of the detrusor muscle and relaxation of the external urinary sphincter to permit urination may be induced by the activation of one or more of the light-responsive opsin proteins expressed in the neurons. In some embodiments, relaxation of the detrusor muscle and contraction of the external urinary sphincter to allow urine storage may be induced by the activation of one or more of the light-responsive opsin proteins expressed in the neurons. In some embodiments contraction of the external anal sphincter to permit storage of stool may be induced by the activation of one or more light-responsive opsin proteins expressed in the neurons. In some embodiments, relaxation of the external anal sphincter to permit defecation may be induced by the activation of one or more of the light-responsive opsin proteins expressed in the neurons. Furthermore, defecation may be additionally facilitated by simultaneous contraction of the muscles responsible for the contraction of the rectum induced by the activation of one or more of the light-responsive opsin proteins expressed in the neurons. In some embodiments, sexual dysfunction may be treated by increasing the depolarization of the neurons responsible for the innervation of the muscles and organs of the genitalia.

Accordingly, in some aspects, provided herein is a method for treating a bladder dysfunction in an individual in need thereof, the method comprising: administering an effective amount of a polynucleotide comprising a nucleotide sequence encoding a light-responsive opsin protein to the individual, wherein the opsin protein is expressed on the plasma membrane of a population of neurons responsible for the innervation of the detrusor muscle and/or a population of neurons responsible for the innervation of the external urinary sphincter muscle in the individual, wherein the opsin protein induces hyperpolarization of the neurons expressing the opsin protein in response to light, whereby the hyperpolarization of the neurons responsible for the innervation of the detrusor muscle permits storage of urine in the bladder and the hyperpolarization of the neurons responsible for the innervation of the external urinary sphincter muscle permits voiding urine from the bladder, wherein the polynucleotide comprises a nucleotide sequence encoding a light-responsive opsin protein comprising a sequence at least 95% identical to the sequence shown in SEQ ID NO:1, an ER export signal, and a membrane trafficking signal.

In some aspects, provided herein is a method for treating a bladder dysfunction in an individual in need thereof, the method comprising: administering an effective amount of a polynucleotide comprising a nucleotide sequence encoding a light-responsive opsin protein to the individual, wherein the opsin protein is expressed on the plasma membrane of a population of neurons responsible for the innervation of the detrusor muscle and/or a population of neurons responsible for the innervation of the external urinary sphincter muscle in the individual, wherein the opsin protein induces hyperpolarization of the neurons expressing the opsin protein in response to light, whereby the hyperpolarization of the neurons responsible for the innervation of the detrusor muscle permits storage of urine in the bladder and the hyperpolarization of the neurons responsible for the innervation of the external urinary sphincter muscle permits voiding urine from the bladder, wherein the polynucleotide comprises a nucleotide sequence encoding a light-responsive opsin protein comprising a sequence at least 95% identical to the sequence shown in SEQ ID NO:23, an ER export signal, and a membrane trafficking signal.

In some aspects, provided herein is a method for treating a bladder dysfunction in an individual in need thereof, the method comprising: administering an effective amount of a polynucleotide comprising a nucleotide sequence encoding a light-responsive opsin protein to the individual, wherein the opsin protein is expressed on the plasma membrane of a population of neurons responsible for the innervation of the detrusor muscle and/or a population of neurons responsible for the innervation of the external urinary sphincter muscle in the individual, wherein the opsin protein induces hyperpolarization of the neurons expressing the opsin protein in response to light, whereby the hyperpolarization of the neurons responsible for the innervation of the detrusor muscle permits storage of urine in the bladder and the hyperpolarization of the neurons responsible for the innervation of the external urinary sphincter muscle permits voiding urine from the bladder, wherein the polynucleotide comprises a nucleotide sequence encoding a light-responsive opsin protein comprising a sequence at least 95% identical to the sequence shown in SEQ ID NO:4, an ER export signal, and a membrane trafficking signal.

In other aspects, provided herein is a method for treating a bladder dysfunction in an individual in need thereof, the method comprising: administering an effective amount of a polynucleotide comprising a nucleotide sequence encoding a light-responsive opsin protein to the individual, wherein the opsin protein is expressed on the plasma membrane of a population of neurons responsible for the innervation of the detrusor muscle and/or a population of neurons responsible for the innervation of the external urinary sphincter muscle in the individual, wherein the opsin protein is capable of inducing depolarization-induced synaptic depletion of the neurons expressing the opsin protein in response to light, whereby the depolarization-induced synaptic depletion of the neurons responsible for the innervation of the detrusor muscle permits storage of urine in the bladder and the depolarization-induced synaptic depletion of the neurons responsible for the innervation of the external urinary sphincter muscle permits voiding urine from the bladder, wherein the polynucleotide comprises a nucleotide sequence encoding a light-responsive opsin protein comprising a sequence at least 95% identical to the sequence selected from the group consisting of SEQ ID NO:5, SEQ ID NO:6, SEQ ID NO:7, SEQ ID NO:8, SEQ ID NO:9, SEQ ID NO:10, and SEQ ID NO:11.

In some aspects, also provided herein is a method for treating a bladder dysfunction in an individual in need thereof, the method comprising: administering an effective amount of a polynucleotide comprising a nucleotide sequence encoding a light-responsive opsin protein to the individual, wherein the opsin protein is expressed on the plasma membrane of a population of neurons responsible for the innervation of the detrusor muscle and/or a population of neurons responsible for the innervation of the external urinary sphincter muscle in the individual, wherein the opsin protein is capable of inducing depolarization of the neurons, whereby the depolarization of the neurons responsible for the innervation of the detrusor muscle permits voiding urine from the bladder and the depolarization of the neurons responsible for the innervation of the external urinary sphincter muscle permits storage of urine in the bladder, wherein the polynucleotide comprises a nucleotide sequence encoding a light-responsive opsin protein comprising a sequence at least 95% identical to the sequence selected from the group consisting of SEQ ID NO:5, SEQ ID NO:6, SEQ ID NO:7, SEQ ID NO:8, SEQ ID NO:9, SEQ ID NO:10, and SEQ ID NO:11.

In other aspects, provided herein is a method for treating fecal incontinence in an individual in need thereof, the method comprising: administering an effective amount of a polynucleotide comprising a nucleotide sequence encoding a light-responsive opsin protein to the individual, wherein the opsin protein is expressed on the plasma membrane of a population of neurons responsible for the innervation of the external anal sphincter muscle in the individual, wherein the opsin protein induces hyperpolarization of the neurons expressing the opsin protein in response to light, whereby the hyperpolarization of the neurons responsible for the innervation of the external anal sphincter muscle permits defecation, wherein the polynucleotide comprises a nucleotide sequence encoding a light-responsive opsin protein comprising a sequence at least 95% identical to the sequence shown in SEQ ID NO:1, an ER export signal, and a membrane trafficking signal.

In other aspects, provided herein is a method for treating fecal incontinence in an individual in need thereof, the method comprising: administering an effective amount of a polynucleotide comprising a nucleotide sequence encoding a light-responsive opsin protein to the individual, wherein the opsin protein is expressed on the plasma membrane of a population of neurons responsible for the innervation of the external anal sphincter muscle in the individual, wherein the opsin protein induces hyperpolarization of the neurons expressing the opsin protein in response to light, whereby the hyperpolarization of the neurons responsible for the innervation of the external anal sphincter muscle permits defecation, wherein the polynucleotide comprises a nucleotide sequence encoding a light-responsive opsin protein comprising a sequence at least 95% identical to the sequence shown in SEQ ID NO:4, an ER export signal, and a membrane trafficking signal.

In other aspects, provided herein is a method for treating fecal incontinence in an individual in need thereof, the method comprising: administering an effective amount of a polynucleotide comprising a nucleotide sequence encoding a light-responsive opsin protein to the individual, wherein the opsin protein is expressed on the plasma membrane of a population of neurons responsible for the innervation of the external anal sphincter muscle in the individual, wherein the opsin protein induces hyperpolarization of the neurons expressing the opsin protein in response to light, whereby the hyperpolarization of the neurons responsible for the innervation of the external anal sphincter muscle permits defecation, wherein the polynucleotide comprises a nucleotide sequence encoding a light-responsive opsin protein comprising a sequence at least 95% identical to the sequence shown in SEQ ID NO:23, an ER export signal, and a membrane trafficking signal.

In yet other aspects, provided herein is a method for treating fecal incontinence in an individual in need thereof, the method comprising: administering an effective amount of a polynucleotide comprising a nucleotide sequence encoding a light-responsive opsin protein to the individual, wherein the opsin protein is expressed on the plasma membrane of a population of neurons responsible for the innervation of the external anal sphincter muscle in the individual, wherein the opsin protein is capable of inducing depolarization-induced synaptic depletion of the neurons expressing the opsin protein in response to light, whereby the depolarization-induced synaptic depletion of the neurons responsible for the innervation of the external anal sphincter muscle permits defecation, wherein the polynucleotide comprises a nucleotide sequence encoding a light-responsive opsin protein comprising a sequence at least 95% identical to the sequence selected from the group consisting of SEQ ID NO:5, SEQ ID NO:6, SEQ ID NO:7, SEQ ID NO:8, SEQ ID NO:9, SEQ ID NO:10, and SEQ ID NO:11.

In another aspect, provided herein is a method for treating fecal incontinence in an individual in need thereof, the method comprising: administering an effective amount of a polynucleotide comprising a nucleotide sequence encoding a light-responsive opsin protein to the individual, wherein the opsin protein is expressed on the plasma membrane of a population of neurons responsible for the innervation of the external anal sphincter muscle in the individual, wherein the opsin protein is capable of inducing depolarization of the neurons, whereby the depolarization of the neurons responsible for the innervation of the external anal sphincter muscle permits storage of stool in the rectum, wherein the polynucleotide comprises a nucleotide sequence encoding a light-responsive opsin protein comprising a sequence at least 95% identical to the sequence selected from the group consisting of SEQ ID NO:5, SEQ ID NO:6, SEQ ID NO:7, SEQ ID NO:8, SEQ ID NO:9, SEQ ID NO:10, and SEQ ID NO:11.

In other aspects, provided herein is a method for treating sexual dysfunction in an individual in need thereof, the method comprising: administering an effective amount of a polynucleotide comprising a nucleotide sequence encoding a light-responsive opsin protein to the individual, wherein the opsin protein is expressed on the plasma membrane of a population of neurons responsible for the innervation of the genitalia of the individual, wherein the opsin protein induces depolarization of the neurons expressing the opsin protein in response to light, whereby the depolarization of the neurons responsible for the innervation of the genitalia restores sexual function.

In another aspect, provided herein is a kit for treating a bladder dysfunction in an individual in need thereof, comprising: a) a polynucleotide encoding a light-responsive opsin protein, wherein the polynucleotide comprises a nucleotide sequence encoding the opsin protein comprising a sequence at least 95% identical to the sequence shown in SEQ ID NO:1, an ER export signal, and a membrane trafficking signal; and b) a light source capable of generating light in response to an external signal, wherein the light is capable of activating the opsin protein.

In another aspect, provided herein is a kit for treating a bladder dysfunction in an individual in need thereof, comprising: a) a polynucleotide encoding a light-responsive opsin protein, wherein the polynucleotide comprises a nucleotide sequence encoding the opsin protein comprising a sequence at least 95% identical to the sequence shown in SEQ ID NO:4, an ER export signal, and a membrane trafficking signal; and b) a light source capable of generating light in response to an external signal, wherein the light is capable of activating the opsin protein.

In another aspect, provided herein is a kit for treating a bladder dysfunction in an individual in need thereof, comprising: a) a polynucleotide encoding a light-responsive opsin protein, wherein the polynucleotide comprises a nucleotide sequence encoding the opsin protein comprising a sequence at least 95% identical to the sequence shown in SEQ ID NO:23, an ER export signal, and a membrane trafficking signal; and b) a light source capable of generating light in response to an external signal, wherein the light is capable of activating the opsin protein.

In still other aspects, provided herein is a kit for treating a bladder dysfunction in an individual in need thereof, comprising: a) a polynucleotide encoding a light-responsive opsin protein, wherein the polynucleotide comprises a nucleotide sequence encoding an amino acid sequence comprising a sequence at least 95% identical to one or more sequences selected from the group consisting of SEQ ID NO:4, SEQ ID NO:5, SEQ ID NO:6, SEQ ID NO:7, SEQ ID NO:8, SEQ ID NO:9, SEQ ID NO:10, and SEQ ID NO:11; and b) a light source capable of generating light in response to an external signal, wherein the light is capable of activating the opsin protein.

In another aspect, provided herein is a kit for treating fecal incontinence in an individual in need thereof, comprising: a) a polynucleotide encoding a light-responsive opsin protein, wherein the polynucleotide comprises a nucleotide sequence encoding the opsin protein comprising a sequence at least 95% identical to the sequence shown in SEQ ID NO:1, an ER export signal, and a membrane trafficking signal; and b) a light source capable of generating light in response to an external signal, wherein the light is capable of activating the opsin protein.

In yet another aspect, provided herein is a kit for treating fecal incontinence in an individual in need thereof, comprising: a) a polynucleotide encoding a light-responsive opsin protein, wherein the polynucleotide comprises a nucleotide sequence encoding an amino acid sequence comprising a sequence at least 95% identical to one or more sequences selected from the group consisting of SEQ ID NO:4, SEQ ID NO:5, SEQ ID NO:6, SEQ ID NO:7, SEQ ID NO:8, SEQ ID NO:9, SEQ ID NO:10, and SEQ ID NO:11; and b) a light source capable of generating light in response to an external signal, wherein the light is capable of activating the opsin protein.

In other aspects, provided herein is a kit for treating sexual dysfunction in an individual in need thereof, comprising: a) a polynucleotide encoding a light-responsive opsin protein, wherein the polynucleotide comprises a nucleotide sequence encoding an amino acid sequence comprising a sequence at least 95% identical to one or more sequences selected from the group consisting of SEQ ID NO:5, SEQ ID NO:6, SEQ ID NO:7, SEQ ID NO:8, SEQ ID NO:9, SEQ ID NO:10, and SEQ ID NO:11; and b) a light source capable of generating light in response to an external signal, wherein the light is capable of activating the opsin protein.

DETAILED DESCRIPTION

Figure 1:
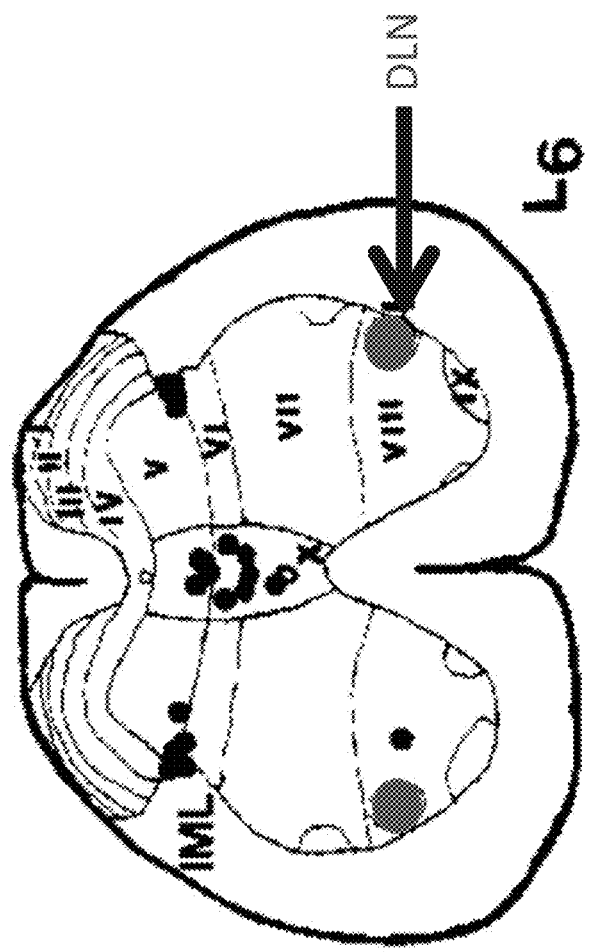
FIG. 1 depicts schematically the various sections of the spinal cord, including the dorsolateral nucleus (DLN).

This invention provides, inter alia, methods for treating bladder dysfunction, fecal incontinence, and/or sexual dysfunction in an individual by selectively altering the electrical membrane potential of the peripheral neuronal cells that govern the filling and voiding of the urinary bladder, the contraction of the external anal sphincter, and/or the innervation of the muscles and organs of the genitalia. The inventors have developed methods to treat diseases and conditions that disrupt normal urinary, rectal, and sexual function using one or more light-responsive opsin proteins which are stably expressed in the peripheral neural cells that innervate the muscles and organs responsible for these physiological processes.

Selective control of the membrane polarization state of nerves which innervate the detrusor and external urinary sphincter (also referred to as "external urethral sphincter") permits the bladder to fill while simultaneously allowing the external urinary sphincter to remain in a "closed" state. This can be accomplished by the selective hyperpolarization or depolarization-induced synaptic depletion of detrusor innervations via the use of light-responsive ion pumps or cation channels, respectively, and permitting the external urinary sphincter innervations to depolarize naturally into a closed state. Alternatively, if neural control of the external urinary sphincter is disrupted, damaged, or otherwise unable to generate sufficient muscular strength to close the sphincter, optogenetic or traditional electrostimulatory methods can be used in combination with optogenetic control of the detrusor to close the external urinary sphincter.

When the individual feels the urge to void or wishes to void according to a predetermined schedule, the nerves which innervate the external urinary sphincter can be selectively hyperpolarized or subjected to depolarization-induced synaptic depletion, causing the sphincter to relax, while simultaneously ceasing the selective hyperpolarization or depolarization-induced synaptic depletion of the detrusor, permitting it to naturally depolarize and contract, thereby forcing urine out of the bladder. If the innervations of the detrusor muscle are disrupted, damaged, or otherwise unable to generate sufficient muscular strength to void the urinary bladder, however, optogenetic or electrostimulatory methods may then be used to drive depolarization of these neurons, thereby forcing the detrusor to contract and void the content of the bladder.

Thus, the methods disclosed herein can relieve or prevent many of the symptoms associated with bladder dysfunctions (for example, detrusor hyperreflexia and detrusor external sphincter dyssynergia) including, but not limited to, daytime and night time wetting, urinary retention, urinary tract and bladder infections, vesicoureteral reflux, hydroureteronephrosis, kidney stones, renal insufficiency, and/or renal failure.

Selective control of the membrane polarization state of nerves which innervate the external anal sphincter permits control of defecation and storage of stool in the rectum. This can be accomplished by the selective hyperpolarization or depolarization-induced synaptic depletion of external anal sphincter innervations via the use of light-responsive ion pumps or cation channels, respectively. When the individual feels the urge to defecate or wishes to defecate according to a predetermined schedule, the nerves which innervate the external anal sphincter can be selectively hyperpolarized or subjected to depolarization-induced synaptic depletion, causing the naturally contracted sphincter muscle to relax. When defecation is completed, optogenetic hyperpolarization or depolarization-induced synaptic depletion of external anal sphincter innervations can cease, resulting in the external anal sphincter returning to its natural, closed state. Alternatively, if neural control of the external anal sphincter is disrupted, damaged, or otherwise unable to generate sufficient muscular strength to naturally close the sphincter, optogenetic or traditional electrostimulatory methods can be used to close the external anal sphincter. Additionally, control of fecal continence can be further enhanced by simultaneous selective depolarization of the innervations of the rectum, compelling the rectum to contract and force its contents into and through the optogenetically-relaxed external anal sphincter. Thus, the methods disclosed herein can relieve or prevent fecal incontinence.

Selective control of the membrane polarization state of nerves which innervate the external genitalia of both men and women permits restoration of sexual function. This can be accomplished by the selective depolarization of one or more sacral spinal nerves and/or components of the pudendal nerve trunk to control sexual function such as—in males—erection, ejaculation, or orgasm, and—in females—vaginal lubrication or orgasm, as well as to restore tactile sensations needed to maintain sexual arousal via the use of light-responsive cation channels. Thus, the methods disclosed herein can restore sexual function.

General Techniques

The practice of the present invention will employ, unless otherwise indicated, conventional techniques of molecular biology, microbiology, cell biology, biochemistry, nucleic acid chemistry, immunology, physiology, urology, and the pathophysiology of urination which are well known to those skilled in the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994); Harlow and Lane (1988) *Antibodies, A Laboratory Manual*, Cold Spring Harbor Publications, New York; Harlow and Lane (1999) *Using Antibodies: A Laboratory Manual*, Cold Spring Harbor Laboratory Press, Cold Spring Harbor, N.Y. (jointly referred to herein as "Harlow and Lane"), Beaucage et al. eds., *Current Protocols in Nucleic Acid Chemistry*, John Wiley & Sons, Inc., New York, 2000), *Handbook of Experimental Immunology*, 4th edition (D. M. Weir & C. C. Blackwell, eds., Blackwell Science Inc., 1987); and *Gene Transfer Vectors for Mammalian Cells* (J. M. Miller & M. P. Calos, eds., 1987). Other useful references include Harrison's *Principles of Internal Medicine* (McGraw Hill; J. Isseleacher et al., eds.), Corcos & Schickik, *Textbook of the Neurogenic Bladder: Adults and Children*. (Informa Health Care, 2004), Walsh et al., *Campbell's Urology*, $8^{th}$ ed., (Saunders, 2002), *Fecal Incontinence: Diagnosis and Treatment*, (Ratto & Doglietto, eds., Springer, 2007), and Lechtenberg et al., *Sexual Dysfunction: Neurologic, Urologic, and Gynecologic Aspects* (Lippincott Williams & Wilkins, 1994).

Definitions

As used herein, "depolarization-induced synaptic depletion" occurs when continuous depolarization of a neural cell plasma membrane prevents the neural cell from sustaining high frequency action on efferent targets due to depletion of terminal vesicular stores of neurotransmitters.

An "individual" can be a mammal, including a human. Mammals include, but are not limited to, farm animals, sport animals, pets, primates, mice and rats. Individuals also include companion animals including, but not limited to, dogs and cats. In one aspect, an individual is a human. In another aspect, an individual is a non-human animal.

Amino acid substitutions in a native protein sequence may be "conservative" or "non-conservative" and such substituted amino acid residues may or may not be one encoded by the genetic code. A "conservative amino acid substitution" is one in which the amino acid residue is replaced with an amino acid residue having a chemically similar side chain (i.e., replacing an amino acid possessing a basic side chain with another amino acid with a basic side chain). A "non-conservative amino acid substitution" is one in which the amino acid residue is replaced with an amino acid residue having a chemically different side chain (i.e., replacing an amino acid having a basic side chain with an amino acid having an aromatic side chain). The standard twenty amino acid "alphabet" is divided into chemical families based on chemical properties of their side chains. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), betabranched side chains (e.g., threonine, valine, isoleucine) and side chains having aromatic groups (e.g., tyrosine, phenylalanine, tryptophan, histidine).

As used herein, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, "treatment" or "treating" is an approach for obtaining beneficial or desired results including clinical results. For purposes of this invention, beneficial or desired clinical results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of individuals.

As used herein "sacral spinal nerve" refers to any of the mixed spinal nerves which carry motor, sensory, and autonomic signals between the spinal cord and the body originating near one of the five fused sacral bones of the vertebral column (such as any of S1, S2, S3, S4, or S5).

As used herein, the singular forms "a", "an", and "the" include plural references unless indicated otherwise.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Urinary Bladder Physiology

The lower urinary tract of healthy individuals has two discrete phases of activity: the storage phase, wherein urine is stored in the bladder; and the voiding phase, occurring when urine is released through the urethra. This reflex system is controlled by both a conscious signal from the brain and the firing rate of sensory fibers contained within the bladder and urethra (Yoshimura & Chancellor, 2003, *Rev. Urol.* 5 (Suppl 8): S3-S10). The bladder of an average person can hold 350 ml to 550 ml of urine. When the volume of fluid in the bladder is low, sensory receptor nerve firing is low, resulting in excitation and depolarization of the neural cells innervating the external urinary sphincter and relaxation of the detrusor muscle surrounding the urinary bladder (Blok & Holstege, *Neurosci. Lett.*, 1994, 166 (1): 93-6). When the bladder is almost full, stretch receptors lining the bladder wall trigger an increase in afferent firing, resulting in the conscious sensation of urinary urge. Generally, a person feels the need to urinate when there is approximately 200 ml of urine in the bladder. When the individual is ready to urinate, he or she consciously initiates voiding, resulting in bladder contraction and the relaxation of the external urinary sphincter. Voiding continues until the bladder empties completely, at which point the bladder relaxes and the external urinary sphincter contracts to re-initiate storage. The muscles controlling the micturition reflex are controlled by both the autonomic and somatic nervous systems. During the storage phase, the internal urethral sphincter remains tense and the detrusor muscle relaxed by sympathetic stimulation. During micturition, parasympathetic stimulation causes the detrusor muscle to contract and the internal urethral sphincter to relax. The external urinary sphincter (a.k.a. sphincter urethrae) is under somatic control and is consciously relaxed during micturition.

Neurogenic dysfunction of the urinary bladder is most often caused by diseases of or injuries to the cells of the central nervous system or the peripheral nerves involved in the control of urination. Detrusor hyperreflexia (DH) and detrusor-external sphincter dyssynergia (DSD) are two conditions that result from disruption of the central nervous system's regulation of the micturition reflex. The methods described herein may be used to alleviate the symptoms of bladder dysfunction in individuals.

Detrusor Hyperreflexia

The detrusor urinate muscle, (a.k.a. detrusor muscle, muscularis propria of the urinary bladder, and muscularis propria) surrounds the urinary bladder and contracts when urinating to squeeze out urine. Otherwise, it remains relaxed to allow the bladder to fill. Detrusor hyperreflexia refers to a neurogeneic condition whereby the detrusor muscle abnormally contracts which prevents the bladder from fully emptying. Symptoms of DH range from detrusor underactivity to overactivity, depending on the site and nature of neurologic insult. For example, "detrusor hyperreflexia with impaired contractility" (DHIC) refers to overactive bladder symptoms, but the detrusor muscle is unable to produce enough pressure to permit total emptying. Therefore, the detrusor is too weak to mount an adequate contraction for proper voiding to occur. The condition is similar to urinary retention, but irritating voiding symptoms are prevalent. Additionally, "detrusor areflexia" refers to the complete inability of the detrusor to empty due to a lower motor neuron lesion (e.g., to the sacral cord or peripheral nerves).

Causes of detrusor hyperreflexia are varied. Lesions to the brain in the region above the pons destroy the micturition master control center, resulting in a complete loss of voiding control. However, the primitive voiding reflexes of the lower urinary tract are still intact. Individuals sustaining such an injury exhibit urge incontinence (a.k.a. spastic bladder). In this case, the bladder empties quickly and often, with relatively low volumes of urine. Additionally, storage of urine in the bladder is difficult and individuals with this problem typically rush to the bathroom and even leak urine before reaching their destination. Often, the condition results in the disruption of sleep several times during the night, requiring the individual to make several trips to relieve the urge to void. Typical examples of brain lesions which can result in the symptoms of detrusor hyperreflexia, include, without limitation, stroke, brain tumor, Parkinson disease, Hydrocephalus, cerebral palsy, and traumatic brain injury.

Diseases or injuries of the spinal cord between the pons and the sacral spinal cord can also result in detrusor hyperreflexia. Individuals sustaining spinal injuries resulting in paraplegia or quadriplegia typically experience lower extremity spasticity. In the period initially following spinal cord trauma, the individual experiences a loss of sensation accompanied by motor paralysis with initial loss but gradual recovery of reflexes after about 6-12 weeks. This gradual recovery of the nervous system often leads to hyperstimulation of affected organs, including the detrusor muscle of the bladder. Similar to individuals with brain lesions, individuals suffering spinal cord trauma often experience urge incontinence. In addition to accidents associated with sports injuries or motor vehicles, multiple sclerosis (MS) can also cause of spinal cord disease. Additionally, children born with myelomeningocele can also exhibit neurogenic bladders leading to symptoms associated with detrusor hyperreflexia. In some aspects of the methods for treating detrusor hyperreflexia provided herein, an injury to the nervous system which causes detrusor hyperreflexia in an individual does not occur in nerve cells located inferior to the second, third, and/or fourth sacral spinal nerves (S2, S3, S4).

Diseases resulting in peripheral neuropathy can also cause symptoms associated with detrusor hyperreflexia. Diabetes mellitus and AIDS can damage or destroy the nerves which innervate the detrusor muscle of the bladder and can lead to silent and painless distention of the bladder. Patients with chronic diabetes can lose the sensation of bladder filling first, before the bladder decompensates. Affected individuals have difficulty urinating and may also experience DHIC. Other non-limiting examples of diseases of the peripheral nervous system that can cause detrusor hyperreflexia are poliomyelitis, Guillain-Barré syndrome, severe herpes in the genitoanal area, pernicious anemia, and neurosyphilis.

Detrusor hyperreflexia is diagnosed via cystometry, which is used to evaluate bladder function. Pressure-flow studies involve the measurement of detrusor pressures while the patient is voiding to distinguish DH from detrusor acontractility. Additional diagnostic information can be obtained from: a voiding diary, urinalysis and culture, plasma electrolyte and creatinine levels or a renal tract ultrasound which includes measurement of post-void residual (PVR) urine volume.

Detrusor-External Sphincter Dyssynergia (DSD)

This voiding disorder is similar to detrusor hyperreflexia except that the external urinary sphincter may have paradoxical contractions simultaneously with those of the detrusor muscle when attempting to void. Normally, the detrusor muscle and the external urinary sphincter operate in synergy, such that when one is contracting (e.g. the sphincter during storage phase or the detrusor during voiding phase) the other is relaxed (e.g. the sphincter during voiding phase or the detrusor during storage phase). If both the bladder and external sphincter contract at the same time, the affected individual will sense an intense desire to urinate but may only be able to actually void a small amount. The medical term for this is detrusor-external sphincter dyssynergia because the bladder and the external sphincter are not operating in synergy. Even though the bladder is trying to force out urine, the external sphincter is tightening to prevent urine from leaving.

Both the detrusor muscle and the external urinary sphincter are innervated via nerves that originate in the sacral spinal cord. The detrusor muscle is innervated by the parasympathetic detrusor innervations arising from the sacral spinal nerves. The external urinary sphincter, on the other hand, is innervated by the external urinary sphincter innervations of the pudendal nerve. The pudendal nerve originates in the sacral plexus and derives its fibers from the ventral branches of the second, third, and fourth sacral spinal nerves (S2, S3, S4). It passes between the piriformis and coccygeus muscles and leaves the pelvis through the lower part of the greater sciatic foramen. It then crosses the spine of the ischium, and reenters the pelvis through the lesser sciatic foramen. It accompanies the internal pudendal vessels upward and forward along the lateral wall of the ischiorectal fossa, and is contained in a sheath of the obturator fascia known as the pudendal canal. The pudendal nerve gives off the inferior rectal nerves and then divides into two terminal branches: the perineal nerve, and the dorsal nerve of the penis (males) or the dorsal nerve of the clitoris (in females). The inferior anal nerves branch off shortly after passing through the greater sciatic foramen. In some aspects of the methods for treating detrusor-external sphincter dyssynergia provided herein, an injury to the nervous system which causes detrusor-external sphincter dyssynergia in an individual does not occur in nerve cells located inferior to the second, third, and/or fourth sacral spinal nerves (S2, S3, S4).

DSD is diagnosed initially from an electromyography (EMG) trace of the urethral sphincter which measures the electrical potentials generated by depolarization of muscle cells. Videourodynamic studies are used to confirm DSD and identify other physiologic or anatomic irregularities.

Fecal Incontinence

Fecal incontinence (FI) is the loss of regular control of the bowels. Involuntary excretion and leaking are common occurrences for those affected. Fecal incontinence can be caused by damage to the nerves that control the anal sphincters or to the nerves that detect stool in the rectum. Damage to the nerves controlling the sphincter muscles may render the muscles unable to work effectively. If the sensory nerves are damaged, detection of stool in the rectum is disabled, and one will not feel the need to defecate until too late. Nerve damage can be caused by, without limitation, childbirth, long-term constipation, stroke, and diseases that cause nerve degeneration, such as diabetes and multiple sclerosis. Damage to the spinal cord may also result in fecal incontinence. Additionally, while the rectum normally stretches to hold stool until it is voluntarily released, rectal surgery, radiation treatment, and inflammatory bowel disease can cause scarring, which may result in the walls of the rectum becoming stiff and less elastic. The rectal walls are unable to stretch as much and are unable to accommodate as much stool leading to FI. Inflammatory bowel disease also can make rectal walls very irritated and thereby unable to contain stool.

The anal sphincters keep the anus closed as stool collects in the rectum. Eventually pressure on the rectal wall causes the internal anal sphincter to relax while conscious motor control over the external anal sphincter (EAS) allows stool to pass out of the body through the anus. The EAS is a flat plane of muscular fibers, elliptical in shape and intimately adherent to the integument surrounding the margin of the anus. The EAS is, like other muscles, always in a state of tonic contraction, and having no antagonistic muscle it keeps the anal canal and orifice closed. Additionally, it can be put into a condition of greater contraction under the influence of the will, so as more firmly to occlude the anal aperture. It is innervated by a branch from the fourth sacral spinal nerve (S4) and by the rectal (a.k.a inferior hemorrhoidal) branch of the pudendal nerve.

Sexual Dysfunction

Sexual dysfunction refers to a difficulty experienced by an individual or a couple during any stage of a normal sexual activity, including desire, arousal, or orgasm. There are many factors which may result in a person experiencing a sexual dysfunction which may result from emotional or physical causes. For example, sexual activity may be impacted by physical factors such as use of drugs, alcohol, nicotine, narcotics, stimulants, antihypertensives, antihistamines, and some psychotherapeutic drugs. Injuries to the back may also impact sexual activity, as would problems with an enlarged prostate gland, problems with blood supply, and nerve damage (as in spinal cord injuries). Disease, such as diabetic neuropathy, multiple sclerosis, tumors, and, rarely, tertiary syphilis, may also impact sexual activity, as would failure of various organ systems (such as the heart and lungs), endocrine disorders (for example, hypothalamus, thyroid, pituitary, or adrenal gland problems), hormonal deficiencies (for example, low testosterone, estrogen, or androgens), and some birth defects.

For males, the skin of the penis is innervated by the dorsal nerve of the penis which is the deepest division of the pudendal nerve; it accompanies the internal pudendal artery along the ramus of the ischium, running forward along the margin of the inferior ramus of the pubis, between the superior and inferior layers of the fascia of the urogenital diaphragm. In females, the clitoris is innervated by a similar branch of the pudendal nerve known as the dorsal nerve of the clitoris. Additionally, the pudendal nerve plays a role in the innervation of the bulbospongiosus and ischiocavernosus muscles and areas around the scrotum (in males), perineum, and anus. During sexual intercourse, at sexual climax, spasms in the bulbospongiosus and ischiocavernous result in ejaculation in the male and most of the external sensations associated with the experience of orgasm in both sexes.

Light-Responsive Opsin Proteins

Provided herein are optogenetic-based methods for selectively hyperpolarizing or depolarizing the neurons responsible for the innervation of the detrusor muscle and the external urinary sphincter with light-responsive opsin proteins to effectively restore detrusor-sphincter synergy in individuals afflicted with bladder dysfunction (such as DH and DSD). Also provided herein are optogenetic-based methods for selectively hyperpolarizing or depolarizing the neurons responsible for the innervation of the external anal sphincter to effectively restore bowel control in individuals afflicted with fecal incontinence. Additionally, provided herein are optogenetic-based methods for selectively depolarizing the neurons responsible for the innervation of the muscles and organs of the genitalia with light-responsive opsin proteins to effectively restore sexual function in individuals afflicted with sexual dysfunction. Optogenetics refers to the combination of genetic and optical methods used to control specific events in targeted cells of living tissue, even within freely moving mammals and other animals, with the temporal precision (millisecond-timescale) needed to keep pace with functioning intact biological systems. Optogenetics requires the introduction of fast light-responsive channel or pump proteins to the plasma membranes of target neuronal cells that allow temporally precise manipulation of neuronal membrane potential while maintaining cell-type resolution through the use of specific targeting mechanisms. Any microbial opsin that can be used to promote neural cell membrane hyperpolarization or depolarization in response to light may be used. For example, the Halorhodopsin family of light-responsive chloride pumps (e.g., NpHR, NpHR2.0, NpHR3.0, NpHR3.1) and the GtR3 proton pump can be used to promote neural cell membrane hyperpolarization in response to light. As another example, eARCH (a proton pump) can be used to promote neural cell membrane hyperpolarization in response to light. Additionally, members of the Channelrhodopsin family of light-responsive cation channel proteins (e.g., ChR2, SFOs, SSFOs, C1V1s) can be used to promote neural cell membrane depolarization or depolarization-induced synaptic depletion in response to a light stimulus.

Enhanced Intracellular Transport Amino Acid Motifs

The present disclosure provides for the modification of light-responsive opsin proteins expressed in a cell by the addition of one or more amino acid sequence motifs which enhance transport to the plasma membranes of mammalian cells. Light-responsive opsin proteins having components derived from evolutionarily simpler organisms may not be expressed or tolerated by mammalian cells or may exhibit impaired subcellular localization when expressed at high levels in mammalian cells. Consequently, in some embodiments, the light-responsive opsin proteins expressed in a cell can be fused to one or more amino acid sequence motifs selected from the group consisting of a signal peptide, an endoplasmic reticulum (ER) export signal, a membrane trafficking signal, and/or an N-terminal golgi export signal. The one or more amino acid sequence motifs which enhance light-responsive protein transport to the plasma membranes of mammalian cells can be fused to the N-terminus, the C-terminus, or to both the N- and C-terminal ends of the light-responsive protein. Optionally, the light-responsive protein and the one or more amino acid sequence motifs may be separated by a linker. In some embodiments, the light-responsive protein can be modified by the addition of a trafficking signal (ts) which enhances transport of the protein to the cell plasma membrane. In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:12).

Trafficking sequences that are suitable for use can comprise an amino acid sequence having 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:12)).

A trafficking sequence can have a length of from about 10 amino acids to about 50 amino acids, e.g., from about 10 amino acids to about 20 amino acids, from about 20 amino acids to about 30 amino acids, from about 30 amino acids to about 40 amino acids, or from about 40 amino acids to about 50 amino acids.

Signal sequences that are suitable for use can comprise an amino acid sequence having 90%, 91%, 92%, 93%, 94%, 95%, 96%, 97%, 98%, 99%, or 100%, amino acid sequence identity to an amino acid sequence such as one of the following:

1) the signal peptide of hChR2 (e.g., MDYGGALSAVGRELLFVTNPVVVNGS (SEQ ID NO:13))

2) the β2 subunit signal peptide of the neuronal nicotinic acetylcholine receptor (e.g., MAGHSNSMALFSFSLLWLCSGVLGTEF (SEQ ID NO:14));

3) a nicotinic acetylcholine receptor signal sequence (e.g., MGLRALMLWLLAAAGLVRESLQG (SEQ ID NO:15)); and 4) a nicotinic acetylcholine receptor signal sequence (e.g., MRGTPLLLVVSLFSLLQD (SEQ ID NO:16)).

A signal sequence can have a length of from about 10 amino acids to about 50 amino acids, e.g., from about 10 amino acids to about 20 amino acids, from about 20 amino acids to about 30 amino acids, from about 30 amino acids to about 40 amino acids, or from about 40 amino acids to about 50 amino acids.

Endoplasmic reticulum (ER) export sequences that are suitable for use in a modified opsin of the present disclosure include, e.g., VXXSL (where X is any amino acid) (e.g., VKESL (SEQ ID NO:17); VLGSL (SEQ ID NO:18); etc.); NANSFCYENEVALTSK (SEQ ID NO:19); FXYENE (SEQ ID NO:20) (where X is any amino acid), e.g., FCYENEV (SEQ ID NO:21); and the like. An ER export sequence can have a length of from about 5 amino acids to about 25 amino acids, e.g., from about 5 amino acids to about 10 amino acids, from about 10 amino acids to about 15 amino acids, from about 15 amino acids to about 20 amino acids, or from about 20 amino acids to about 25 amino acids.

Additional protein motifs which can enhance light-responsive protein transport to the plasma membrane of a cell are described in U.S. patent application Ser. No. 12/041,628, which is incorporated herein by reference in its entirety. In some embodiments, the signal peptide sequence in the protein can be deleted or substituted with a signal peptide sequence from a different protein.

Light-Responsive Chloride Pumps

In some aspects of the methods provided herein, one or more members of the Halorhodopsin family of light-responsive chloride pumps are expressed on the plasma membranes of the neural cells which comprise the innervations of the detrusor muscle and the external urinary sphincter. In some embodiments, said one or more light-responsive chloride pumps are expressed on the plasma membrane of the nerves comprising one or more sacral spinal nerves. In other embodiments, said one or more light-responsive chloride pumps are expressed on the plasma membrane of nerves comprising the detrusor innervations arising from the sacral spinal nerves. In another embodiment, said one or more light-responsive chloride pumps are expressed on the plasma membrane of the pudendal nerve. In other embodiments, said one or more light-responsive chloride pumps are expressed on the plasma membrane of nerves comprising the external urinary sphincter innervations of the pudendal nerve.

In some aspects, said one or more light-responsive chloride pump proteins expressed on the plasma membranes of the nerve cells described above can be derived from *Natronomonas pharaonis*. In some embodiments, the light-responsive chloride pump proteins can be responsive to amber light as well as red light and can mediate a hyperpolarizing current in the nerve cell when the light-responsive chloride pump proteins are illuminated with amber or red light. The wavelength of light which can activate the light-responsive chloride pumps can be between about 580 and 630 nm. In some embodiments, the light can be at a wavelength of about 589 nm or the light can have a wavelength greater than about 630 nm (e.g. less than about 740 nm). In another embodiment, the light has a wavelength of around 630 nm. In some embodiments, the light-responsive chloride pump protein can hyperpolarize a neural membrane for at least about 90 minutes when exposed to a continuous pulse of light. In some embodiments, the light-responsive chloride pump protein can comprise an amino acid sequence at least about 90%, 91%, 92%, 93%, 94%, 95%, 96%, 97%, 98%, 99%, or 100% identical to the sequence shown in SEQ ID NO: 1. Additionally, the light-responsive chloride pump protein can comprise substitutions, deletions, and/or insertions introduced into a native amino acid sequence to increase or decrease sensitivity to light, increase or decrease sensitivity to particular wavelengths of light, and/or increase or decrease the ability of the light-responsive protein to regulate the polarization state of the plasma membrane of the cell. In some embodiments, the light-responsive chloride pump protein contains one or more conservative amino acid substitutions. In some embodiments, the light-responsive protein contains one or more non-conservative amino acid substitutions. The light-responsive protein comprising substitutions, deletions, and/or insertions introduced into the native amino acid sequence suitably retains the ability to hyperpolarize the plasma membrane of a neuronal cell in response to light.

Additionally, in other aspects, the light-responsive chloride pump protein can comprise a core amino acid sequence at least about 90%, 91%, 92%, 93%, 94%, 95%, 96%, 97%, 98%, 99%, or 100% identical to the sequence shown in SEQ ID NO: 1 and an endoplasmic reticulum (ER) export signal. This ER export signal can be fused to the C-terminus of the core amino acid sequence or can be fused to the N-terminus of the core amino acid sequence. In some embodiments, the ER export signal is linked to the core amino acid sequence by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the ER export signal can comprise the amino acid sequence FXYENE (SEQ ID NO:20), where X can be any amino acid. In another embodiment, the ER export signal can comprise the amino acid sequence VXXSL, where X can be any amino acid. In some embodiments, the ER export signal can comprise the amino acid sequence FCYENEV (SEQ ID NO:21).

Endoplasmic reticulum (ER) export sequences that are suitable for use in a modified opsin of the present disclosure include, e.g., VXXSL (where X is any amino acid) (e.g., VKESL (SEQ ID NO:17); VLGSL (SEQ ID NO:18); etc.); NANSFCYENEVALTSK (SEQ ID NO:19); FXYENE (where X is any amino acid) (SEQ ID NO:20), e.g., FCYENEV (SEQ ID NO:21); and the like. An ER export sequence can have a length of from about 5 amino acids to about 25 amino acids, e.g., from about 5 amino acids to about 10 amino acids, from about 10 amino acids to about 15 amino acids, from about 15 amino acids to about 20 amino acids, or from about 20 amino acids to about 25 amino acids.

In other aspects, the light-responsive chloride pump proteins provided herein can comprise a light-responsive protein expressed on the cell membrane, wherein the protein comprises a core amino acid sequence at least about 90%, 91%, 92%, 93%, 94%, 95%, 96%, 97%, 98%, 99%, or 100% identical to the sequence shown in SEQ ID NO: 1 and a trafficking signal (e.g., which can enhance transport of the light-responsive chloride pump protein to the plasma membrane). The trafficking signal may be fused to the C-terminus of the core amino acid sequence or may be fused to the N-terminus of the core amino acid sequence. In some embodiments, the trafficking signal can be linked to the core amino acid sequence by a linker which can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:12).

In some aspects, the light-responsive chloride pump protein can comprise a core amino acid sequence at least about 90%, 91%, 92%, 93%, 94%, 95%, 96%, 97%, 98%, 99%, or 100% identical to the sequence shown in SEQ ID NO: 1 and at least one (such as one, two, three, or more) amino acid sequence motifs which enhance transport to the plasma membranes of mammalian cells selected from the group consisting of an ER export signal, a signal peptide, and a membrane trafficking signal. In some embodiments, the light-responsive chloride pump protein comprises an N-terminal signal peptide, a C-terminal ER Export signal, and a C-terminal trafficking signal. In some embodiments, the C-terminal ER Export signal and the C-terminal trafficking signal can be linked by a linker. The linker can comprise any of about 5, 10, 20, 30, 40, 50, 75, 100, 125, 150, 175, 200, 225, 250, 275, 300, 400, or 500 amino acids in length. The linker can also further comprise a fluorescent protein, for example, but not limited to, a yellow fluorescent protein, a red fluorescent protein, a green fluorescent protein, or a cyan fluorescent protein. In some embodiments the ER Export signal can be more C-terminally located than the trafficking signal. In other embodiments the trafficking signal is more C-terminally located than the ER Export signal. In some embodiments, the signal peptide comprises the amino acid sequence MTETLPPVTESAVALQAE (SEQ ID NO:22). In another embodiment, the light-responsive chloride pump protein comprises an amino acid sequence at least 95% identical to SEQ ID NO:2.

Moreover, in other aspects, the light-responsive chloride pump proteins can comprise a core amino acid sequence at least about 90%, 91%, 92%, 93%, 94%, 95%, 96%, 97%, 98%, 99%, or 100% identical to the sequence shown in SEQ ID NO: 1, wherein the N-terminal signal peptide of SEQ ID NO:1 is deleted or substituted. In some embodiments, other signal peptides (such as signal peptides from other opsins) can be used. The light-responsive protein can further comprise an ER transport signal and/or a membrane trafficking signal described herein. In some embodiments, the light-responsive chloride pump protein comprises an amino acid sequence at least 95% identical to SEQ ID NO:3.

In some embodiments, the light-responsive opsin protein is a NpHR opsin protein comprising an amino acid sequence at least 95%, at least 96%, at least 97%, at least 98%, at least 99% or 100% identical to the sequence shown in SEQ ID NO:1. In some embodiments, the NpHR opsin protein further comprises an endoplasmic reticulum (ER) export signal and/or a membrane trafficking signal. For example, the NpHR opsin protein comprises an amino acid sequence at least 95% identical to the sequence shown in SEQ ID NO:1 and an endoplasmic reticulum (ER) export signal. In some embodiments, the amino acid sequence at least 95% identical to the sequence shown in SEQ ID NO:1 is linked to the ER export signal through a linker. In some embodiments, the ER export signal comprises the amino acid sequence FXYENE (SEQ ID NO:20), where X can be any amino acid. In another embodiment, the ER export signal comprises the amino acid sequence VXXSL, where X can be any amino acid. In some embodiments, the ER export signal comprises the amino acid sequence FCYENEV (SEQ ID NO:21). In some embodiments, the NpHR opsin protein comprises an amino acid sequence at least 95% identical to the sequence shown in SEQ ID NO:1, an ER export signal, and a membrane trafficking signal. In other embodiments, the NpHR opsin protein comprises, from the N-terminus to the C-terminus, the amino acid sequence at least 95% identical to the sequence shown in SEQ ID NO:1, the ER export signal, and the membrane trafficking signal. In other embodiments, the NpHR opsin protein comprises, from the N-terminus to the C-terminus, the amino acid sequence at least 95% identical to the sequence shown in SEQ ID NO:1, the membrane trafficking signal, and the ER export signal. In some embodiments, the membrane trafficking signal is derived from the amino acid sequence of the human inward rectifier potassium channel Kir2.1. In some embodiments, the membrane trafficking signal comprises the amino acid sequence KSRITSEGEYIPLDQIDINV (SEQ ID NO:12). In some embodiments, the membrane trafficking signal is linked to the amino acid sequence at least 95% identical to the sequence shown in SEQ ID NO:1 by a linker. In some embodiments, the membrane trafficking signal is linked to the ER export signal through a linker. The linker may comprise any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the light-responsive opsin protein further comprises an N-terminal signal peptide. In some embodiments, the light-responsive opsin protein comprises the amino acid sequence of SEQ ID NO:2. In some embodiments, the light-responsive opsin protein comprises the amino acid sequence of SEQ ID NO:3.

Also provided herein are polynucleotides encoding any of the light-responsive chloride ion pump proteins described herein, such as a light-responsive protein comprising a core amino acid sequence at least about 90%, 91%, 92%, 93%, 94%, 95%, 96%, 97%, 98%, 99%, or 100% identical to the sequence shown in SEQ ID NO:1, an ER export signal, and a membrane trafficking signal. In another embodiment, the polynucleotides comprise a sequence which encodes an amino acid at least 95% identical to SEQ ID NO:2 and SEQ ID NO:3. The polynucleotides may be in an expression vector (such as, but not limited to, a viral vector described herein). The polynucleotides may be used for expression of the light-responsive chloride ion pump proteins.

Further disclosure related to light-responsive chloride pump proteins can be found in U.S. Patent Application Publication Nos: 2009/0093403 and 2010/0145418 as well as in International Patent Application No: PCT/US2011/028893, the disclosures of each of which are hereby incorporated by reference in their entireties.

Light-Responsive Proton Pumps

In some aspects of the methods provided herein, one or more light-responsive proton pumps are expressed on the plasma membranes of the neural cells which comprise the innervations of the detrusor muscle and the external urinary sphincter. In some embodiments, one or more light-responsive proton pumps are expressed on the plasma membrane of the nerves comprising one or more sacral spinal nerves. In other embodiments, the one or more light-responsive proton pumps are expressed on the plasma membrane of nerves comprising the detrusor innervations arising from the sacral spinal nerves. In another embodiment, one or more light-responsive proton pumps are expressed on the plasma membrane of the pudendal nerve. In other embodiments, the one or more light-responsive proton pumps are expressed on the plasma membrane of nerves comprising the external urinary sphincter innervations of the pudendal nerve.

In some embodiments, the light-responsive proton pump protein can be responsive to blue light and can be derived from *Guillardia theta*, wherein the proton pump protein can be capable of mediating a hyperpolarizing current in the cell when the cell is illuminated with blue light. The light can have a wavelength between about 450 and about 495 nm or can have a wavelength of about 490 nm. In another embodiment, the light-responsive proton pump protein can comprise an amino acid sequence at least about 90%, 91%, 92%, 93%, 94%, 95%, 96%, 97%, 98%, 99%, or 100% identical to the sequence shown in SEQ ID NO:4. The light-responsive proton pump protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive proton pump protein to regulate the polarization state of the plasma membrane of the cell. Additionally, the light-responsive proton pump protein can contain one or more conservative amino acid substitutions and/or one or more non-conservative amino acid substitutions. The light-responsive proton pump protein comprising substitutions, deletions, and/or insertions introduced into the native amino acid sequence suitably retains the ability to hyperpolarize the plasma membrane of a neuronal cell in response to light.

In other aspects of the methods disclosed herein, the light-responsive proton pump protein can comprise a core amino acid sequence at least about 90%, 91%, 92%, 93%, 94%, 95%, 96%, 97%, 98%, 99%, or 100% identical to the sequence shown in SEQ ID NO:4 and at least one (such as one, two, three, or more) amino acid sequence motifs which enhance transport to the plasma membranes of mammalian cells selected from the group consisting of a signal peptide, an ER export signal, and a membrane trafficking signal. In some embodiments, the light-responsive proton pump protein comprises an N-terminal signal peptide and a C-terminal ER export signal. In some embodiments, the light-responsive proton pump protein comprises an N-terminal signal peptide and a C-terminal trafficking signal. In some embodiments, the light-responsive proton pump protein comprises an N-terminal signal peptide, a C-terminal ER Export signal, and a C-terminal trafficking signal. In some embodiments, the light-responsive proton pump protein comprises a C-terminal ER Export signal and a C-terminal trafficking signal. In some embodiments, the C-terminal ER Export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

Also provided herein are isolated polynucleotides encoding any of the light-responsive proton pump proteins described herein, such as a light-responsive proton pump protein comprising a core amino acid sequence at least about 90%, 91%, 92%, 93%, 94%, 95%, 96%, 97%, 98%, 99%, or 100% identical to the sequence shown in SEQ ID NO:4. Also provided herein are expression vectors (such as a viral vector described herein) comprising a polynucleotide encoding the proteins described herein, such as a light-responsive proton pump protein comprising a core amino acid sequence at least about 90%, 91%, 92%, 93%, 94%, 95%, 96%, 97%, 98%, 99%, or 100% identical to the sequence shown in SEQ ID NO:4. The polynucleotides may be used for expression of the light-responsive protein in neural cells (e.g. the neural cells which comprise the detrusor innervations arising from the sacral spinal nerves and the external urinary sphincter innervations of the pudendal nerve).

Further disclosure related to light-responsive proton pump proteins can be found in International Patent Application No. PCT/US2011/028893, the disclosure of which is hereby incorporated by reference in its entirety.

In some embodiments, the light-responsive proton pump protein can be responsive to green or yellow light and can be derived from *Halorubrum sodomense*, wherein the proton pump protein can be capable of mediating a hyperpolarizing current in the cell when the cell is illuminated with green or yellow light. The light can have a wavelength between about 560 and about 570 nm or can have a wavelength of about 566 nm. In another embodiment, the light-responsive proton pump protein can comprise an amino acid sequence at least about 90%, 91%, 92%, 93%, 94%, 95%, 96%, 97%, 98%, 99%, or 100% identical to the sequence shown in SEQ ID NO:23. The light-responsive proton pump protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive proton pump protein to regulate the polarization state of the plasma membrane of the cell. Additionally, the light-responsive proton pump protein can contain one or more conservative amino acid substitutions and/or one or more non-conservative amino acid substitutions. The light-responsive proton pump protein comprising substitutions, deletions, and/or insertions introduced into the native amino acid sequence suitably retains the ability to hyperpolarize the plasma membrane of a neuronal cell in response to light.

In other aspects of the methods disclosed herein, the light-responsive proton pump protein can comprise a core amino acid sequence at least about 90%, 91%, 92%, 93%, 94%, 95%, 96%, 97%, 98%, 99%, or 100% identical to the sequence shown in SEQ ID NO:23 and at least one (such as one, two, three, or more) amino acid sequence motifs which enhance transport to the plasma membranes of mammalian cells selected from the group consisting of a signal peptide, an ER export signal, and a membrane trafficking signal. In some embodiments, the light-responsive proton pump protein comprises an N-terminal signal peptide and a C-terminal ER export signal. In some embodiments, the light-responsive proton pump protein comprises an N-terminal signal peptide and a C-terminal trafficking signal. In some embodiments, the light-responsive proton pump protein comprises an N-terminal signal peptide, a C-terminal ER Export signal, and a C-terminal trafficking signal. In some embodiments, the light-responsive proton pump protein comprises a C-terminal ER Export signal and a C-terminal trafficking signal. In some embodiments, the C-terminal ER Export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

Also provided herein are isolated polynucleotides encoding any of the light-responsive proton pump proteins described herein, such as a light-responsive proton pump protein comprising a core amino acid sequence at least about 90%, 91%, 92%, 93%, 94%, 95%, 96%, 97%, 98%, 99%, or 100% identical to the sequence shown in SEQ ID NO:23. Also provided herein are expression vectors (such as a viral vector described herein) comprising a polynucleotide encoding the proteins described herein, such as a light-responsive proton pump protein comprising a core amino acid sequence at least about 90%, 91%, 92%, 93%, 94%, 95%, 96%, 97%, 98%, 99%, or 100% identical to the sequence shown in SEQ ID NO:23. The polynucleotides may be used for expression of the light-responsive protein in neural cells (e.g. the neural cells which comprise the detrusor innervations arising from the sacral spinal nerves and the external urinary sphincter innervations of the pudendal nerve).

Light-Responsive Cation Channel Proteins

In some aspects of the methods provided herein, one or more light-responsive cation channels can be expressed on the plasma membranes of the neural cells which comprise the innervations of the detrusor muscle and the external urinary sphincter. In some embodiments, one or more light-responsive cation channels can be expressed on the plasma membrane of one or more sacral spinal nerves (such as any of S1, S2, S3, S4, and/or S5). In other embodiments, the one or more light-responsive cation channels can be expressed on the plasma membrane of nerves comprising the detrusor innervations arising from the sacral spinal nerves. In another embodiment, one or more light-responsive cation channels can be expressed on the plasma membrane of the pudendal nerve. In other embodiments, the one or more light-responsive cation channels can be expressed on the plasma membrane of nerves comprising the external urinary sphincter innervations of the pudendal nerve.

In some aspects, the light-responsive cation channel protein can be derived from *Chlamydomonas reinhardtii*, wherein the cation channel protein can be capable of mediating a depolarizing current in the cell when the cell is illuminated with light. In another embodiment, the light-responsive cation channel protein can comprise an amino acid sequence at least about 90%, 91%, 92%, 93%, 94%, 95%, 96%, 97%, 98%, 99%, or 100% identical to the sequence shown in SEQ ID NO:5. The light used to activate the light-responsive cation channel protein derived from *Chlamydomonas reinhardtii* can have a wavelength between about 460 and about 495 nm or can have a wavelength of about 480 nm. Additionally, the light can have an intensity of at least about 100 Hz. In some embodiments, activation of the light-responsive cation channel derived from *Chlamydomonas reinhardtii* with light having an intensity of 100 Hz can cause depolarization-induced synaptic depletion of the neurons expressing the light-responsive cation channel. The light-responsive cation channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive cation channel protein to regulate the polarization state of the plasma membrane of the cell. Additionally, the light-responsive cation channel protein can contain one or more conservative amino acid substitutions and/or one or more non-conservative amino acid substitutions. The light-responsive proton pump protein comprising substitutions, deletions, and/or insertions introduced into the native amino acid sequence suitably retains the ability to depolarize the plasma membrane of a neuronal cell in response to light.

In some embodiments, the light-responsive cation channel comprises a T159C substitution of the amino acid sequence set forth in SEQ ID NO:5. In some embodiments, the light-responsive cation channel comprises a L132C substitution of the amino acid sequence set forth in SEQ ID NO:5. In some embodiments, the light-responsive cation channel comprises an E123T substitution of the amino acid sequence set forth in SEQ ID NO:5. In some embodiments, the light-responsive cation channel comprises an E123A substitution of the amino acid sequence set forth in SEQ ID NO:5. In some embodiments, the light-responsive cation channel comprises a T159C substitution and an E123T substitution of the amino acid sequence set forth in SEQ ID NO:5. In some embodiments, the light-responsive cation channel comprises a T159C substitution and an E123A substitution of the amino acid sequence set forth in SEQ ID NO:5. In some embodiments, the light-responsive cation channel comprises a T159C substitution, an L132C substitution, and an E123T substitution of the amino acid sequence set forth in SEQ ID NO:5. In some embodiments, the light-responsive cation channel comprises a T159C substitution, an L132C substitution, and an E123A substitution of the amino acid sequence set forth in SEQ ID NO:5. In some embodiments, the light-responsive cation channel comprises an L132C substitution and an E123T substitution of the amino acid sequence set forth in SEQ ID NO:5. In some embodiments, the light-responsive cation channel comprises an L132C substitution and an E123A substitution of the amino acid sequence set forth in SEQ ID NO:5.

Further disclosure related to light-responsive cation channel proteins can be found in U.S. Patent Application Publication No. 2007/0054319 and International Patent Application Publication Nos. WO 2009/131837 and WO 2007/024391, the disclosures of each of which are hereby incorporated by reference in their entireties.

Step Function Opsins and Stabilized Step Function Opsins

In other embodiments, the light-responsive cation channel protein can be a step function opsin (SFO) protein or a stabilized step function opsin (SSFO) protein that can have specific amino acid substitutions at key positions throughout the retinal binding pocket of the protein. In some embodiments, the SFO protein can have a mutation at amino acid residue C128 of SEQ ID NO:5. In other embodiments, the SFO protein has a C128A mutation in SEQ ID NO:5. In other embodiments, the SFO protein has a C128S mutation in SEQ ID NO:5. In another embodiment, the SFO protein has a C128T mutation in SEQ ID NO:5. In some embodiments, the SFO protein can comprise an amino acid sequence at least about 90%, 91%, 92%, 93%, 94%, 95%, 96%, 97%, 98%, 99%, or 100% identical to the sequence shown in SEQ ID NO:6.

In some embodiments, the SSFO protein can have a mutation at amino acid residue D156 of SEQ ID NO:5. In other embodiments, the SSFO protein can have a mutation at both amino acid residues C128 and D156 of SEQ ID NO:5. In one embodiment, the SSFO protein has an C128S and a D156A mutation in SEQ ID NO:5. In another embodiment, the SSFO protein can comprise an amino acid sequence at least about 90%, 91%, 92%, 93%, 94%, 95%, 96%, 97%, 98%, 99%, or 100% identical to the sequence shown in SEQ ID NO:7. In another embodiment, the SSFO protein can comprise a C128T mutation in SEQ ID NO:5. In some embodiments, the SSFO protein comprises C128T and D156A mutations in SEQ ID NO:5.

In some embodiments the SFO or SSFO proteins provided herein can be capable of mediating a depolarizing current in the cell when the cell is illuminated with blue light. In other embodiments, the light can have a wavelength of about 445 nm. Additionally, the light can have an intensity of about 100 Hz. In some embodiments, activation of the SFO or SSFO protein with light having an intensity of 100 Hz can cause depolarization-induced synaptic depletion of the neurons expressing the SFO or SSFO protein. In some embodiments, each of the disclosed step function opsin and stabilized step function opsin proteins can have specific properties and characteristics for use in depolarizing the membrane of a neuronal cell in response to light.

Further disclosure related to SFO or SSFO proteins can be found in International Patent Application Publication No. WO 2010/056970 and U.S. Provisional Patent Application Nos. 61/410,704 and 61/511,905, the disclosures of each of which are hereby incorporated by reference in their entireties.

C1V1 Chimeric Cation Channels

In other embodiments, the light-responsive cation channel protein can be a C1V1 chimeric protein derived from the VChR1 protein of *Volvox carteri* and the ChR1 protein from *Chlamydomonas reinhardti*, wherein the protein comprises the amino acid sequence of VChR1 having at least the first and second transmembrane helices replaced by the first and second transmembrane helices of ChR1; is responsive to light; and is capable of mediating a depolarizing current in the cell when the cell is illuminated with light. In some embodiments, the C1V1 protein can further comprise a replacement within the intracellular loop domain located between the second and third transmembrane helices of the chimeric light responsive protein, wherein at least a portion of the intracellular loop domain is replaced by the corresponding portion from ChR1. In another embodiment, the portion of the intracellular loop domain of the C1V1 chimeric protein can be replaced with the corresponding portion from ChR1 extending to amino acid residue A145 of the ChR1. In other embodiments, the C1V1 chimeric protein can further comprise a replacement within the third transmembrane helix of the chimeric light responsive protein, wherein at least a portion of the third transmembrane helix is replaced by the corresponding sequence of ChR1. In yet another embodiment, the portion of the intracellular loop domain of the C1V1 chimeric protein can be replaced with the corresponding portion from ChR1 extending to amino acid residue W163 of the ChR1. In other embodiments, the C1V1 chimeric protein can comprise an amino acid sequence at least about 90%, 91%, 92%, 93%, 94%, 95%, 96%, 97%, 98%, 99%, or 100% identical to the sequence shown in SEQ ID NO:8.

In some embodiments, the C1V1 protein can mediate a depolarizing current in the cell when the cell is illuminated with green light. In other embodiments, the light can have a wavelength of between about 540 nm to about 560 nm. In some embodiments, the light can have a wavelength of about 542 nm. In some embodiments, the C1V1 chimeric protein is not capable of mediating a depolarizing current in the cell when the cell is illuminated with violet light. In some embodiments, the chimeric protein is not capable of mediating a depolarizing current in the cell when the cell is illuminated with light having a wavelength of about 405 nm. Additionally, the light can have an intensity of about 100 Hz. In some embodiments, activation of the C1V1 chimeric protein with light having an intensity of 100 Hz can cause depolarization-induced synaptic depletion of the neurons expressing the C1V1 chimeric protein. In some embodiments, the disclosed C1V1 chimeric protein can have specific properties and characteristics for use in depolarizing the membrane of a neuronal cell in response to light.

C1V1 Chimeric Mutant Variants

In some aspects, the present disclosure provides polypeptides comprising substituted or mutated amino acid sequences, wherein the mutant polypeptide retains the characteristic light-activatable nature of the precursor C1V1 chimeric polypeptide but may also possess altered properties in some specific aspects. For example, the mutant light-responsive C1V1 chimeric proteins described herein can exhibit an increased level of expression both within an animal cell or on the animal cell plasma membrane; an altered responsiveness when exposed to different wavelengths of light, particularly red light; and/or a combination of traits whereby the chimeric C1V1 polypeptide possess the properties of low desensitization, fast deactivation, low violet-light activation for minimal cross-activation with other light-responsive cation channels, and/or strong expression in animal cells.

Accordingly, provided herein are C1V1 chimeric light-responsive opsin proteins that can have specific amino acid substitutions at key positions throughout the retinal binding pocket of the VChR1 portion of the chimeric polypeptide. In some embodiments, the C1V1 protein can have a mutation at amino acid residue E122 of SEQ ID NO:7. In some embodiments, the C1V1 protein can have a mutation at amino acid residue E162 of SEQ ID NO:7. In other embodiments, the C1V1 protein can have a mutation at both amino acid residues E162 and E122 of SEQ ID NO:7. In other embodiments, the C1V1 protein can comprise an amino acid sequence at least about 90%, 91%, 92%, 93%, 94%, 95%, 96%, 97%, 98%, 99%, or 100% identical to the sequence shown in SEQ ID NO:9, SEQ ID NO:10, or SEQ ID NO:11. In some embodiments, each of the disclosed mutant C1V1 chimeric proteins can have specific properties and characteristics for use in depolarizing the membrane of an animal cell in response to light.

In some aspects, the C1V1-E122 mutant chimeric protein is capable of mediating a depolarizing current in the cell when the cell is illuminated with light. In some embodiments the light can be green light. In other embodiments, the light can have a wavelength of between about 540 nm to about 560 nm. In some embodiments, the light can have a wavelength of about 546 nm. In other embodiments, the C1V1-E122 mutant chimeric protein can mediate a depolarizing current in the cell when the cell is illuminated with red light. In some embodiments, the red light can have a wavelength of about 630 nm. In some embodiments, the C1V1-E122 mutant chimeric protein does not mediate a depolarizing current in the cell when the cell is illuminated with violet light. In some embodiments, the chimeric protein does not mediate a depolarizing current in the cell when the cell is illuminated with light having a wavelength of about 405 nm. Additionally, the light can have an intensity of about 100 Hz. In some embodiments, activation of the C1V1-E122 mutant chimeric protein with light having an intensity of 100 Hz can cause depolarization-induced synaptic depletion of the neurons expressing the C1V1-E122 mutant chimeric protein. In some embodiments, the disclosed C1V1-E122 mutant chimeric protein can have specific properties and characteristics for use in depolarizing the membrane of a neuronal cell in response to light.

In other aspects, the C1V1-E162 mutant chimeric protein is capable of mediating a depolarizing current in the cell when the cell is illuminated with light. In some embodiments the light can be green light. In other embodiments, the light can have a wavelength of between about 535 nm to about 540 nm. In some embodiments, the light can have a wavelength of about 542 nm. In other embodiments, the light can have a wavelength of about 530 nm. In some embodiments, the C1V1-E162 mutant chimeric protein does not mediate a depolarizing current in the cell when the cell is illuminated with violet light. In some embodiments, the chimeric protein does not mediate a depolarizing current in the cell when the cell is illuminated with light having a wavelength of about 405 nm. Additionally, the light can have an intensity of about 100 Hz. In some embodiments, activation of the C1V1-E162 mutant chimeric protein with light having an intensity of 100 Hz can cause depolarization-induced synaptic depletion of the neurons expressing the C1V1-E162 mutant chimeric protein. In some embodiments, the disclosed C1V1-E162 mutant chimeric protein can have specific properties and characteristics for use in depolarizing the membrane of a neuronal cell in response to light.

In yet other aspects, the C1V1-E122/E162 mutant chimeric protein is capable of mediating a depolarizing current in the cell when the cell is illuminated with light. In some embodiments the light can be green light. In other embodiments, the light can have a wavelength of between about 540 nm to about 560 nm. In some embodiments, the light can have a wavelength of about 546 nm. In some embodiments, the C1V1-E122/E162 mutant chimeric protein does not mediate a depolarizing current in the cell when the cell is illuminated with violet light. In some embodiments, the chimeric protein does not mediate a depolarizing current in the cell when the cell is illuminated with light having a wavelength of about 405 nm. In some embodiments, the C1V1-E122/E162 mutant chimeric protein can exhibit less activation when exposed to violet light relative to C1V1 chimeric proteins lacking mutations at E122/E162 or relative to other light-responsive cation channel proteins. Additionally, the light can have an intensity of about 100 Hz. In some embodiments, activation of the C1V1-E122/E162 mutant chimeric protein with light having an intensity of 100 Hz can cause depolarization-induced synaptic depletion of the neurons expressing the C1V1-E122/E162 mutant chimeric protein. In some embodiments, the disclosed C1V1-E122/E162 mutant chimeric protein can have specific properties and characteristics for use in depolarizing the membrane of a neuronal cell in response to light.

Further disclosure related to C1V1 chimeric cation channels as well as mutant variants of the same can be found in U.S. Provisional Patent Application Nos. 61/410,736, 61/410,744, and 61/511,912, the disclosures of each of which are hereby incorporated by reference in their entireties.

Polynucleotides

The disclosure also provides polynucleotides comprising a nucleotide sequence encoding a light-responsive protein described herein. In some embodiments, the polynucleotide comprises an expression cassette. In some embodiments, the polynucleotide is a vector comprising the above-described nucleic acid. In some embodiments, the nucleic acid encoding a light-responsive protein of the disclosure is operably linked to a promoter. Promoters are well known in the art. Any promoter that functions in the host cell can be used for expression of the light-responsive opsin proteins and/or any variant thereof of the present disclosure. In one embodiment, the promoter used to drive expression of the light-responsive opsin proteins can be a promoter that is specific to motor neurons. In other embodiments, the promoter is capable of driving expression of the light-responsive opsin proteins in neurons of both the sympathetic and/or the parasympathetic nervous systems. Initiation control regions or promoters, which are useful to drive expression of the light-responsive opsin proteins or variant thereof in a specific animal cell are numerous and familiar to those skilled in the art. Virtually any promoter capable of driving these nucleic acids can be used. Examples of motor neuron-specific genes can be found, for example, in Kudo, et al., *Human Mol. Genetics*, 2010, 19(16): 3233-3253, the contents of which are hereby incorporated by reference in their entirety. In some embodiments, the promoter used to drive expression of the light-responsive protein can be the Thy1 promoter, which is capable of driving robust expression of transgenes in neurons of both the central and peripheral nervous systems (See, e.g., Llewellyn, et al., 2010, *Nat. Med.*, 16(10):1161-1166). In other embodiments, the promoter used to drive expression of the light-responsive protein can be the EF1α promoter, a cytomegalovirus (CMV) promoter, the CAG promoter, a synapsin-I promoter (e.g., a human synapsin-I promoter), a human synuclein 1 promoter, a human Thy1 promoter, a calcium/calmodulin-dependent kinase II alpha (CAMKIIα) promoter, or any other promoter capable of driving expression of the light-responsive opsin proteins in the peripheral neurons of mammals.

Also provided herein are vectors comprising a nucleotide sequence encoding a light-responsive protein or any variant thereof described herein. The vectors that can be administered according to the present invention also include vectors comprising a nucleotide sequence which encodes an RNA (e.g., an mRNA) that when transcribed from the polynucleotides of the vector will result in the accumulation of light-responsive opsin proteins on the plasma membranes of target animal cells. Vectors which may be used, include, without limitation, lentiviral, HSV, adenoviral, and adeno-associated viral (AAV) vectors. Lentiviruses include, but are not limited to HIV-1, HIV-2, SIV, FIV and EIAV. Lentiviruses may be pseudotyped with the envelope proteins of other viruses, including, but not limited to VSV, rabies, Mo-MLV, baculovirus and Ebola. Such vectors may be prepared using standard methods in the art.

In some embodiments, the vector is a recombinant AAV vector. AAV vectors are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

AAV vectors may be prepared using standard methods in the art. Adeno-associated viruses of any serotype are suitable (see, e.g., Blacklow, pp. 165-174 of "*Parvoviruses and Human Disease*" J. R. Pattison, ed. (1988); Rose, *Comprehensive Virology* 3:1, 1974; P. Tattersall "The Evolution of Parvovirus Taxonomy" In *Parvoviruses* (J R Kerr, S F Cotmore. M E Bloom, R M Linden, C R Parrish, Eds.) p5-14, Hudder Arnold, London, UK (2006); and D E Bowles, J E Rabinowitz, R J Samulski "*The Genus Dependovirus*" (J R Kerr, S F Cotmore. M E Bloom, R M Linden, C R Parrish, Eds.) p15-23, Hudder Arnold, London, UK (2006), the disclosures of each of which are hereby incorporated by reference herein in their entireties). Methods for purifying for vectors may be found in, for example, U.S. Pat. Nos. 6,566,118, 6,989,264, and 6,995,006 and WO/1999/011764 titled "Methods for Generating High Titer Helper-free Preparation of Recombinant AAV Vectors", the disclosures of which are herein incorporated by reference in their entirety. Methods of preparing AAV vectors in a baculovirus system are described in, e.g., WO 2008/024998. AAV vectors can be self-complementary or single-stranded. Preparation of hybrid vectors is described in, for example, PCT Application No. PCT/US2005/027091, the disclosure of which is herein incorporated by reference in its entirety. The use of vectors derived from the AAVs for transferring genes in vitro and in vivo has been described (See e.g., International Patent Application Publication Nos.: 91/18088 and WO 93/09239; U.S. Pat. Nos. 4,797,368, 6,596,535, and 5,139,941; and European Patent No.: 0488528, all of which are hereby incorporated by reference herein in their entireties). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the present disclosure can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In some embodiments, the vector(s) for use in the methods of the present disclosure are encapsidated into a virus particle (e.g. AAV virus particle including, but not limited to, AAV1, AAV2, AAV3, AAV4, AAV5, AAV6, AAV7, AAV8, AAV9, AAV10, AAV11, AAV12, AAV13, AAV14, AAV15, and AAV16). Accordingly, the present disclosure includes a recombinant virus particle (recombinant because it contains a recombinant polynucleotide) comprising any of the vectors described herein. Methods of producing such particles are known in the art and are described in U.S. Pat. No. 6,596,535, the disclosure of which is hereby incorporated by reference in its entirety.

Delivery of Light-Responsive Opsin Proteins

In some aspects, polynucleotides encoding the light-responsive opsin proteins disclosed herein (for example, an AAV vector) can be delivered directly to the neurons responsible for the innervation of the detrusor muscle and/or the neurons responsible for the innervation of the external urinary sphincter with a needle, catheter, or related device, using neurosurgical techniques known in the art, such as by stereotactic injection (See, e.g., Stein et al., *J. Virol*, 73:34243429, 1999; Davidson et al., *PNAS*, 97:3428-3432, 2000; Davidson et al., *Nat. Genet.* 3:219-223, 1993; and Alisky & Davidson, *Hum. Gene Ther.* 11:2315-2329, 2000, the contents of each of which are hereby incorporated by reference herein in their entireties) or fluoroscopy. In some embodiments, the polynucleotide encoding the light-responsive opsin proteins disclosed herein (for example, an AAV1 vector) can be delivered to the neurons responsible for the innervation of the detrusor muscle by injection of the polynucleotide into the somatic motor neuron cell body of one or more sacral spinal nerves (such as any of S1, S2, S3, S4, and/or S5). In other embodiments, the polynucleotide encoding the light-responsive opsin proteins disclosed herein (for example, an AAV vector) can be delivered to the neurons responsible for the innervation of the external urinary sphincter by injection of the polynucleotide into the pudendal nerve. In another embodiment, the polynucleotide encoding the light-responsive opsin proteins disclosed herein (for example, an AAV vector) can be delivered to the neurons responsible for the innervation of the external urinary sphincter by injection of the polynucleotide into Onuf's nucleus.

In some aspects, polynucleotides encoding the light-responsive opsin proteins disclosed herein (for example, an AAV vector) can be delivered directly to the neurons responsible for the innervation of the external anal sphincter with a needle, catheter, or related device, using neurosurgical techniques known in the art, such as by stereotactic injection or fluoroscopy. In some embodiments, the polynucleotide encoding the light-responsive opsin proteins disclosed herein (for example, an AAV vector) can be delivered to the neurons responsible for the innervation of the external anal sphincter by injection of the polynucleotide into a somatic motor neuron cell body of a sacral spinal nerve (for example, any of S1, S2, S3, S4, and/or S5). In other embodiments, the polynucleotide encoding the light-responsive opsin proteins disclosed herein (for example, an AAV vector) can be delivered to the neurons responsible for the innervation of the external anal sphincter by injection of the polynucleotide into the pudendal nerve or by injection of the polynucleotide into Onuf's nucleus. In other embodiments, the polynucleotide encoding the light-responsive opsin proteins disclosed herein (for example, an AAV vector) can be delivered to the neurons responsible for the innervation of the rectum by injection of the polynucleotide in a somatic motor neuron cell body of a sacral spinal nerve (for example, any of S1, S2, S3, S4, and/or S5) or by injection into the inferior hypogastric plexis.

In some aspects, polynucleotides encoding the light-responsive opsin proteins disclosed herein (for example, an AAV vector) can be delivered directly to the neurons responsible for the innervation of the muscles and organs of the male and female genitalia with a needle, catheter, or related device, using neurosurgical techniques known in the art, such as by stereotactic injection or fluoroscopy. In some embodiments, the polynucleotide encoding the light-responsive opsin proteins disclosed herein (for example, an AAV vector) can be delivered to the neurons responsible for the innervation of the muscles and organs of the male and female genitalia by injection of the polynucleotide into a somatic motor neuron cell body of a sacral spinal nerve (for example, any of S1, S2, S3, S4, and/or S5). In other embodiments, the polynucleotide encoding the light-responsive opsin proteins disclosed herein (for example, an AAV vector) can be delivered to the neurons responsible for the innervation of the muscles and organs of the male and female genitalia by injection of the polynucleotide into the pudendal nerve or by injection of the polynucleotide into Onuf's nucleus.

Other methods to deliver the light-responsive opsin proteins to the nerves of interest can also be used, such as, but not limited to, transfection with ionic lipids or polymers, electroporation, optical transfection, impalefection, or via gene gun.

In another aspect, the polynucleotide encoding the light-responsive opsin proteins disclosed herein (for example, an AAV vector) can be delivered directly to the detrusor muscle of the bladder and/or the muscles responsible for the contraction of the external urinary sphincter. Because of the limitations inherent in injecting viral vectors directly into the specific cell bodies which innervate particular muscles, researchers have attempted to deliver transgenes to peripheral neurons by injecting viral vectors directly into muscle. These experiments have shown that some viral serotypes such as adenovirus, AAV2, and Rabies glycoprotein-pseudotyped lentivirus can be taken up by muscle cells and retrogradely transported to motor neurons across the neuromuscular synapse (See, e.g., Azzouz et al., 2009, *Antioxid Redox Signal.*, 11(7):1523-34; Kaspar et al., 2003, *Science*, 301 (5634):839-842; Manabe et al., 2002. *Apoptosis*, 7(4):329-334, the disclosures of each of which are herein incorporated by reference in their entireties).

Accordingly, in some embodiments, the polynucleotides encoding the light-responsive opsin proteins disclosed herein (for example, an AAV vector) can be delivered to the neurons responsible for the innervation of the external urinary sphincter by injection of the polynucleotide expression vector directly into the muscles responsible for contraction of the external urinary sphincter. In another embodiment, the polynucleotides encoding the light-responsive opsin proteins disclosed herein (for example, an AAV vector) can be delivered to the neurons responsible for the innervation of the detrusor muscle by injection of the polynucleotide expression vector directly into the detrusor muscle. In other embodiments, the polynucleotides encoding the light-responsive opsin proteins disclosed herein (for example, an AAV vector) can be delivered to the neurons responsible for the innervation of the external anal sphincter by injection of the polynucleotide expression vector directly into the muscles responsible for contraction of the external anal sphincter. In other embodiments, the polynucleotides encoding the light-responsive opsin proteins disclosed herein (for example, an AAV vector) can be delivered to the neurons responsible for the innervation of the rectum by injection of the polynucleotide expression vector directly into the muscles responsible for contraction of the rectum. In yet another embodiment, the polynucleotides encoding the light-responsive opsin proteins disclosed herein (for example, an AAV vector) can be delivered to the neurons responsible for the innervation of the male and female genitalia by injection of the polynucleotide expression vector directly into the muscles and organs responsible for normal sexual function including, but not limited to, the bulbospongiosus and ischiocavernosus muscles of the penis, the skin of the penis, the perennial muscles, or the clitoris.

Light and Electrical Sources

In some aspects of the present disclosure, the light-responsive opsin proteins disclosed herein can be activated by an implantable light source (such as a light cuff) or an implantable electrode placed around or near nerve fibers expressing the light-responsive opsin proteins or nerves controlling the muscles of the bladder, external urinary sphincter, external anal sphincter, rectum, and/or the male or female genitalia. Electrode cuffs and electrodes surgically placed around or near nerves for use in electrical stimulation of those nerves are well known in the art (See, for example, U.S. Pat. Nos. 4,602,624, 7,142,925 and 6,600,956 as well as U.S. Patent Publication Nos. 2008/0172116 and 2010/0094372, the disclosures of each of which are hereby incorporated by reference in their entireties). The light sources (such as a light cuff) or electrodes of the present invention can be comprised of any useful composition or mixture of compositions, such as platinum or stainless steel, as are known in the art, and may be of any useful configuration for stimulating the light-responsive opsin proteins disclosed herein or nerves controlling the muscles and organs of the bladder, external urinary sphincter external anal sphincter, and/or male or female genitalia.

The electrodes or implantable light source (such as a light cuff) may be placed around or near a nerve, such as, but not limited to, the detrusor innervations arising from the sacral spinal nerves, the external urinary sphincter innervations of the pudendal nerve, the external anal sphincter innervations arising from the sacral spinal nerves and/or the inferior rectal nerve (a.k.a inferior hemorrhoidal nerve) arising from the pudendal nerve, the innervations of the rectum arising from the sacral spinal nerves and/or the inferior hypogastric plexus, the dorsal nerve of the penis arising from the pudendal nerve, and/or the dorsal nerve of the clitoris arising from the pudendal nerve. The nerve fibers responsible for the innervation of the aforementioned muscles and/or organs can be identified by clinicians prior to placing the electrode or implantable light source around or near the nerve fibers using known techniques in the art. For example, nerve fibers may be stimulated with brief pulses of electricity and the location of the muscular contractions caused by said electrical stimulation observed to ensure correct placement of the electrode or implantable light source. The electrodes or implantable light source are well suited to be used in conjunction with the pudendal nerve in particular, either on the pudendal nerve trunk or its afferent or efferent branches away from the sacral root (from whence the pudendal nerve originates), that innervate the muscles and organs of the lower urinary tract, the bowel, the perenium and the genitals. The pudendal nerve trunk and its branches are spaced away from the sacral root and spinal column. Consequently, they are surgically accessible from the front of the body and do not require complex surgical procedures on, in, or near the spinal column or entailing dorsal rhizotomy. In another embodiment, a light source may be placed near the ventral roots of the desired nerve targets. In another embodiment, a light source comprises a fiber optic cable placed near a desired nerve target that is surgically exposed.

In some embodiments, the implantable light source (such as a light cuff) does not completely surround the nerve, but, rather, can have a U-shape. In another embodiment, the implantable light source can have an attachment arm that can be used to guide the implantable light source (such as a light cuff) to the nerve fibers (e.g., the detrusor innervations arising from the sacral spinal nerves and/or the external urinary sphincter innervations of the pudendal nerve). The attachment arm can be removed following implantation of the light source or can be left in place to fix the position of the light source in proximity to the nerve fibers of interest.

The implantable light source (such as a light cuff) can comprise an inner body, the inner body having at least one means for generating light which is configured to a power source. In some embodiments, the power source can be an internal battery for powering the light-generating means. In another embodiment, the implantable light source can comprise an external antenna for receiving wirelessly transmitted electromagnetic energy from an external source for powering the light-generating means. The wirelessly transmitted electromagnetic energy can be a radio wave, a microwave, or any other electromagnetic energy source that can be transmitted from an external source to power the light-generating means of the implantable light source (such as a light cuff). In one embodiment, the light-generating means is controlled by an integrated circuit produced using semiconductor or other processes known in the art.

In some aspects, the light means can be a light emitting diode (LED). In some embodiments, the LED can generate blue and/or green light. In other embodiments, the LED can generate amber and/or yellow light. In some embodiments, several micro LEDs are embedded into the inner body of the implantable light source (such as a light cuff). In other embodiments, the light-generating means is a solid state laser diode or any other means capable of generating light. The light generating means can generate light having an intensity sufficient to activate the light-responsive opsin proteins expressed on the plasma membrane of the nerves in proximity to the light source (such as a light cuff). In some embodiments, the light-generating means produces light having an intensity of any of about 0.05 mW/mm$^2$, 0.1 mW/mm$^2$, 0.2 mW/mm$^2$, 0.3 mW/mm$^2$, 0.4 mW/mm$^2$, 0.5 mW/mm$^2$, about 0.6 mW/mm$^2$, about 0.7 mW/mm$^2$, about 0.8 mW/mm$^2$, about 0.9 mW/mm$^2$, about 1.0 mW/mm$^2$, about 1.1 mW/mm$^2$, about 1.2 mW/mm$^2$, about 1.3 mW/mm$^2$, about 1.4 mW/mm$^2$, about 1.5 mW/mm$^2$, about 1.6 mW/mm$^2$, about 1.7 mW/mm$^2$, about 1.8 mW/mm$^2$, about 1.9 mW/mm$^2$, about 2.0 mW/mm$^2$, about 2.1 mW/mm$^2$, about 2.2 mW/mm$^2$, about 2.3 mW/mm$^2$, about 2.4 mW/mm$^2$, about 2.5 mW/mm$^2$, about 3 mW/mm$^2$, about 3.5 mW/mm$^2$, about 4 mW/mm$^2$, about 4.5 mW/mm$^2$, about 5 mW/mm$^2$, about 5.5 mW/mm$^2$, about 6 mW/mm$^2$, about 7 mW/mm$^2$, about 8 mW/mm$^2$, about 9 mW/mm$^2$, or about 10 mW/mm$^2$, inclusive, including values in between these numbers. In other embodiments, the light-generating means produces light having an intensity of at least about 100 Hz.

In some aspects, the light-generating means can be externally activated by an external controller. The external controller can comprise a power generator which can be mounted to a transmitting coil. In some embodiments of the external controller, a battery can be connected to the power generator, for providing power thereto. A switch can be connected to the power generator, allowing an individual to manually activate or deactivate the power generator. In some embodiments, upon activation of the switch, the power generator can provide power to the light-generating means on the light source through electromagnetic coupling between the transmitting coil on the external controller and the external antenna of the implantable light source (such as a light cuff). The transmitting coil can establish an electromagnetic coupling with the external antenna of the implantable light source when in proximity thereof, for supplying power to the light-generating means and for transmitting one or more control signals to the implantable light source. In some embodiments, the electromagnetic coupling between the transmitting coil of the external controller and the external antenna of the implantable light source (such as a light cuff) can be radio-frequency magnetic inductance coupling. When radio-frequency magnetic inductance coupling is used, the operational frequency of the radio wave can be between about 1 and 20 MHz, inclusive, including any values in between these numbers (for example, about 1 MHz, about 2 MHz, about 3 MHz, about 4 MHz, about 5 MHz, about 6 MHz, about 7 MHz, about 8 MHz, about 9 MHz, about 10 MHz, about 11 MHz, about 12 MHz, about 13 MHz, about 14 MHz, about 15 MHz, about 16 MHz, about 17 MHz, about 18 MHz, about 19 MHz, or about 20 MHz). However, other coupling techniques may be used, such as an optical receiver, infrared, or a biomedical telemetry system (See, e.g., Kiourti, "Biomedical Telemetry: Communication between Implanted Devices and the External World, *Opticon*1826, (8): Spring, 2010).

In some aspects of the present disclosure, more than one of the detrusor innervations arising from the sacral spinal nerves, the external urinary sphincter innervations of the pudendal nerve, the external anal sphincter innervations of the pudendal or sacral spinal nerves can express light-responsive pumps that promote nerve hyperpolarization when activated with light. In some embodiments, the light-generating means of the implantable light source placed around or near the detrusor innervations arising from the sacral spinal nerves generates light continuously when the bladder is storing urine while, at the same time, the implantable light source (such as a light cuff) placed around or near the external urinary sphincter innervations of the pudendal nerve does not generate light. In another aspect, the light-generating means of the implantable light source (such as a light cuff) placed around or near the detrusor innervations arising from the sacral spinal nerves does not generate light when the bladder is voiding while, at the same time, the implantable light source (such as a light cuff) placed around or near the external urinary sphincter innervations of the pudendal nerve can generate light continuously. In some embodiments, a first control signal generated by the external controller can activate the light generating means of the implantable light source (such as a light cuff) placed around or near the detrusor innervations arising from the sacral spinal nerves while simultaneously deactivating the implantable light source (such as a light cuff) placed around or near the external urinary sphincter innervations of the pudendal nerve. In another embodiment, a second control signal generated by the external controller can deactivate the light generating means of the implantable the light source (such as a light cuff) placed around or near the detrusor innervations arising from the sacral spinal nerves while simultaneously activating the implantable light source (such as a light cuff) placed around or near the external urinary sphincter innervations of the pudendal nerve. In another embodiment, a control signal generated by the external controller can activate the light generating means of the implantable the light source (such as a light cuff) placed around or near the external anal sphincter innervations arising from the pudendal or sacral spinal nerves.

In some aspects of the present disclosure, the detrusor innervations arising from the sacral spinal nerves, the external urinary sphincter innervations of the pudendal nerve, and/or the external anal sphincter innervations of the pudendal or sacral spinal nerves can express light-responsive cation channels that promote nerve depolarization-induced synaptic depletion when activated with light. In some embodiments, the light-generating means of the implantable light source placed around or near the detrusor innervations arising from the sacral spinal nerves does not generate light when the bladder is storing urine while, at the same time, the implantable light source (such as a light cuff) placed around or near the external urinary sphincter innervations of the pudendal nerve can generate light having an intensity of at least 100 Hz continuously. In another aspect, the light-generating means of the implantable light source (such as a light cuff) placed around or near the detrusor innervations arising from the sacral spinal nerves generates light having an intensity of at least 100 Hz when the bladder is voiding while, at the same time, the implantable light source (such as a light cuff) placed around or near the external urinary sphincter innervations of the pudendal nerve does not generate light. In another aspect, the light-generating means of the implantable light source (such as a light cuff) placed around or near the external anal sphincter innervations arising from the pudendal or sacral spinal nerves generates light having an intensity of at least 100 Hz when the external anal sphincter is relaxing. In some embodiments, a first control signal generated by the external controller can activate the light generating means of the implantable light source (such as a light cuff) placed around or near the detrusor innervations arising from the sacral spinal nerves while simultaneously deactivating the implantable light source (such as a light cuff) placed around or near the external urinary sphincter innervations of the pudendal nerve. In another embodiment, a second control signal generated by the external controller can deactivate the light generating means of implantable the light source (such as a light cuff) placed around or near the detrusor innervations arising from the sacral spinal nerves while simultaneously activating the implantable light source (such as a light cuff) placed around or near the external urinary sphincter innervations of the pudendal nerve. In another embodiment, a control signal generated by the external controller can deactivate the light generating means of implantable the light source (such as a light cuff) placed around or near the external anal sphincter innervations arising from the pudendal or sacral spinal nerves.

In some aspects of the present disclosure, the innervations of the muscles or organs of the male or female genitalia arising from the pudendal nerve or one or more sacral spinal nerves can express light-responsive cation channel proteins that promote nerve depolarization when activated with light. In some embodiments, the light-generating means of the implantable light source placed around or near the innervations of the male or female genitalia arising from the pudendal or sacral spinal nerves generates light continuously when the individual wishes to engage in sexual activity such as, but not limited to, erection, orgasm, ejaculation, and/or vaginal lubrication. In some embodiments, the light-generating means of the implantable light source placed around or near the innervations of the male or female genitalia arising from the pudendal or sacral spinal nerves generates light continuously when the individual wishes to restore tactile sensations in the genital area required to maintain sexual arousal. In some embodiments, a first control signal generated by the external controller can activate the light generating means of the implantable light source (such as a light cuff) placed around or near the innervations of the muscles or organs of the male or female genitalia arising from the pudendal or sacral spinal nerves In another embodiment, a second control signal generated by the external controller can deactivate the light generating means of implantable the light source (such as a light cuff) placed around or near the innervations of the muscles or organs of the male or female genitalia arising from the pudendal or sacral spinal nerves.

In other aspects of the present disclosure, a combination of nerve stimulation with light-responsive opsin proteins and electricity can be used to restore urinary and/or fecal continence. In some embodiments, the detrusor innervations arising from the sacral spinal nerves can express any of the light-responsive opsin proteins described herein and an electrode can be placed around or near the external urinary sphincter innervations of the pudendal nerve. In some embodiments, the external anal sphincter innervations arising from the sacral spinal nerves and/or the pudendal nerves can have an electrode placed around or near the external anal sphincter innervations arising from the pudendal nerve and/or the sacral spinal nerves. In other embodiments, an electrode can be placed around or near the detrusor innervations arising from the sacral spinal nerves while the external urinary sphincter innervations of the pudendal nerve can express any of the light-responsive opsin proteins described herein. In some embodiments, a first control signal generated by the external controller can activate the light generating means of the implantable light source (such as a light cuff) placed around or near the detrusor innervations arising from the sacral spinal nerves while simultaneously activating an electrode placed around or near the external urinary sphincter innervations of the pudendal nerve. In another embodiment, a second control signal generated by the external controller can deactivate the light generating means of the implantable light source (such as a light cuff) placed around or near the detrusor innervations arising from the sacral spinal nerves while simultaneously deactivating an electrode placed around or near the external urinary sphincter innervations of the pudendal nerve. In another embodiment, a first control signal generated by the external controller can deactivate an electrode placed around or near the detrusor innervations arising from the sacral spinal nerves while simultaneously activating a light generating means of the implantable light source (such as a light cuff) placed around or near the external urinary sphincter innervations of the pudendal nerve. In yet another embodiment, a second control signal generated by the external controller can activate an electrode placed around or near the detrusor innervations arising from the sacral spinal nerves while simultaneously deactivating a light generating means of the implantable light source (such as a light cuff) placed around or near the external urinary sphincter innervations of the pudendal nerve.

Examples of light stimulation devices, including light source (such as a light cuff), can be found in International Patent Application Nos: PCT/US08/50628 and PCT/US09/49936 and in Llewellyn et al., 2010, *Nat. Med.*, 16(10):161-165, the disclosures of each of which are hereby incorporated herein in their entireties.

Methods

The present invention is directed to methods for inhibiting the symptoms (disabilities, impairments) associated with bladder dysfunction, fecal incontinence (FI), and/or sexual dysfunction. Particularly, the methods provided herein are directed towards treating and/or alleviating the symptoms associated with detrusor hyperreflexia (DH) and/or detrusor external sphincter dyssynergia (DSD). As such, it is not required that physiological damage or all effects of the condition be entirely reversed, although the effects of the presently disclosed methods likely extend to a significant therapeutic benefit for the patient. As such, a therapeutic benefit is not necessarily a complete cure for DH, DSD, FI, and/or sexual dysfunction, but rather, can encompass a result which includes reducing or preventing the symptoms or physiological damage resulting from these conditions, reducing or preventing the occurrence of such symptoms or damage (either quantitatively or qualitatively), reducing the severity of such symptoms or physiological effects, and/or enhancing the recovery of the patient after experiencing a cause of DH, DSD, FI, and/or sexual dysfunction (for example, but not limited to, spinal cord injury and multiple sclerosis).

Specifically, the methods of the present invention may prevent damage associated with prolonged DH, DSD, FI, and/or sexual dysfunction, and/or reduce or alleviate symptoms of or conditions associated with (resulting from) these conditions. As such, protecting an individual from the physiological effects or symptoms resulting from DH, DSD, FI, and/or sexual dysfunction includes both preventing or reducing the occurrence and/or severity of the effects of the symptoms and treating a patient in which the symptoms are already occurring or beginning to occur. A beneficial effect can easily be assessed by one of ordinary skill in the art and/or by a trained clinician who is treating the patient. For example, many of the methods described above for the diagnosis of DH and/or DSD can be used to evaluate the patient before and after treatment using a method of the present invention to assess the success of the treatment. In some embodiments, there is a positive or beneficial difference in the severity or occurrence of at least one clinical or biological score, value, or measure used to evaluate such patients in those who have been treated with the methods of the present invention as compared to those that have not.

Figure 4:
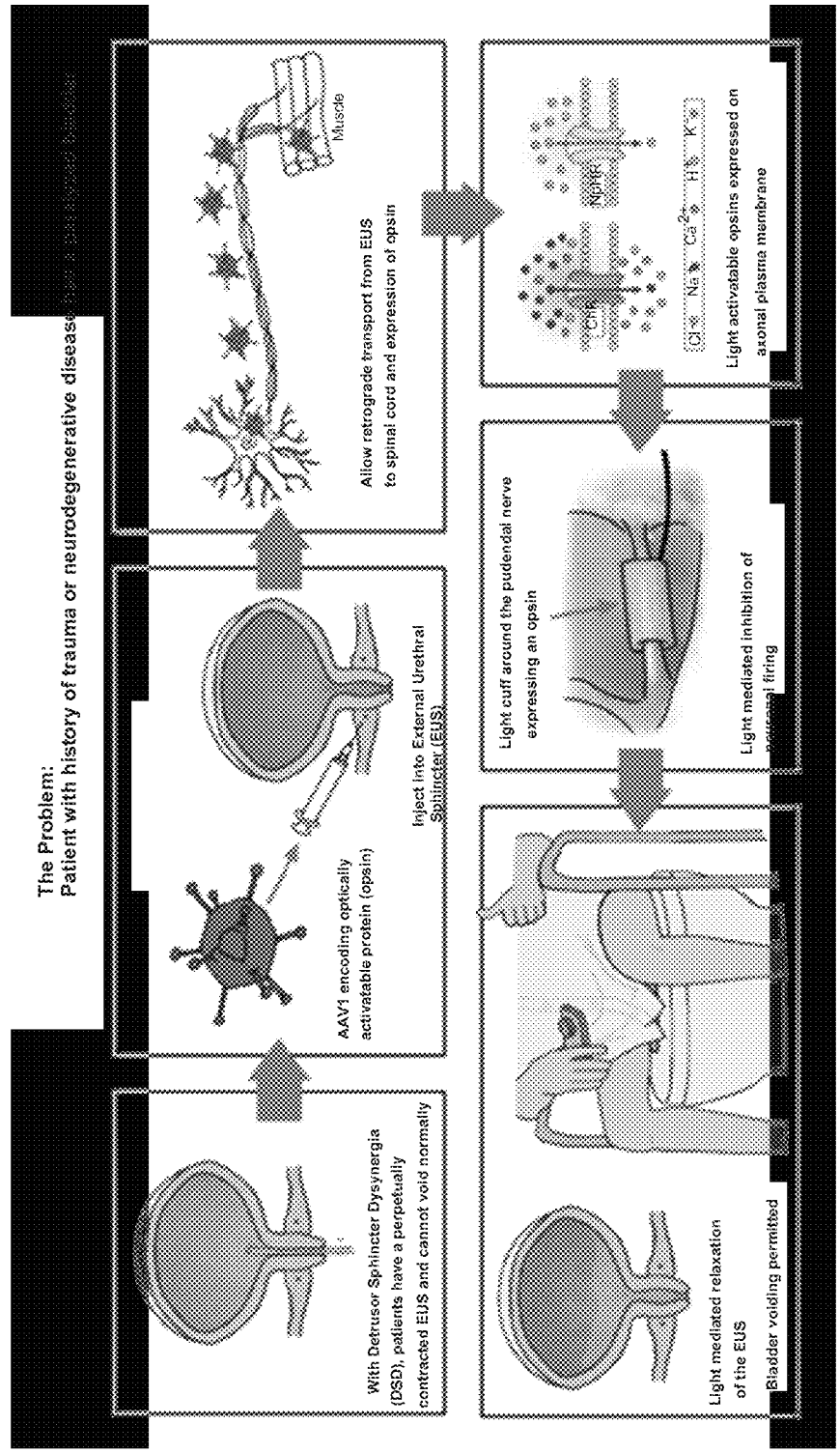
FIG. 4 depicts an exemplary embodiment of optogenetic control of the EUS.

Hyperpolarization or Depolarization-Induced Synaptic Depletion with Light-Responsive Opsin Proteins for Treating Bladder Dysfunction and/or Fecal Incontinence Bladder Dysfunction Accordingly, provided herein is a method for treating a bladder dysfunction in an individual in need thereof, the method comprising administering an effective amount of a polynucleotide comprising a nucleotide sequence encoding a light-responsive opsin protein to the individual, wherein the light-responsive opsin protein is expressed on the plasma membrane of a population of neurons responsible for the innervation of the detrusor muscle and/or a population of neurons responsible for the innervation of the external urinary sphincter muscle in the individual, wherein the light-responsive opsin protein is capable of inducing hyperpolarization of the neurons expressing the light-responsive opsin protein in response to light, whereby the hyperpolarization of the neurons responsible for the innervation of the detrusor muscle permits storage of urine in the bladder and the hyperpolarization of the neurons responsible for the innervation of the external urinary sphincter muscle permits voiding urine from the bladder. Any polynucleotides described herein that encode a light-responsive opsin protein capable of inducing hyperpolarization may be administered. In some embodiments, the bladder dysfunction is DH and/or DSD. In other embodiments, the population of neurons responsible for the innervation of the detrusor muscle and/or a population of neurons responsible for the innervation of the external urinary sphincter muscle are hyperpolarized by exposure to amber light. An exemplary embodiment of a subject method is depicted schematically in FIG. 4.

When illuminated by an implantable light source (such as a light cuff) placed around or near the detrusor innervations arising from the sacral spinal nerves, the light-responsive opsin proteins expressed on the plasma membranes of the detrusor innervations maintain a hyperpolarized neural membrane potential preventing contraction of the detrusor muscle and permitting the bladder to fill. When the light-responsive opsin proteins expressed on the detrusor innervations arising from the sacral spinal nerves are not illuminated by the implantable light source, the detrusor muscle is able to contract due to the recovery of normal neural membrane potential and the pressure generated facilitates voiding. Similarly, when illuminated by an implantable light source placed around or near the external urinary sphincter innervations of the pudendal nerve, the light-responsive opsin proteins expressed on the plasma membranes of the external urinary sphincter innervations maintain a hyperpolarized neural membrane potential, preventing contraction of the external urinary sphincter and permitting the individual to void. When the light-responsive opsin proteins expressed on the external urinary sphincter innervations of the pudendal nerve are not illuminated by the implantable light source, the external urinary sphincter contracts and permits the bladder to fill.

Also provided herein is a method for treating a bladder dysfunction in an individual in need thereof, the method comprising administering an effective amount of a polynucleotide comprising a nucleotide sequence encoding a light-responsive opsin protein to the individual, wherein the light-responsive opsin protein is expressed on the plasma membrane of a population of neurons responsible for the innervation of the detrusor muscle and/or a population of neurons responsible for the innervation of the external urinary sphincter muscle in the individual, wherein the light-responsive opsin protein is capable of causing depolarization-induced synaptic depletion of the neurons expressing the light-responsive protein in response to light, whereby the depolarization-induced synaptic depletion of the neurons responsible for the innervation of the detrusor muscle permits storage of urine in the bladder and the depolarization-induced synaptic depletion of the neurons responsible for the innervation of the external urinary sphincter muscle permits voiding urine from the bladder. Any polynucleotides described herein that encode a light-responsive option protein capable of causing depolarization-induced synaptic depletion may be administered. In some embodiments, the bladder dysfunction is DH and/or DSD. In other embodiments, the population of neurons responsible for the innervation of the detrusor muscle and/or a population of neurons responsible for the innervation of the external urinary sphincter muscle can be depolarized to the point of synaptic depletion by exposure to blue, green, yellow, orange, or red light. In some embodiments, the light has an intensity of at least about 100 Hz.

When illuminated by an implantable light source (such as a light cuff) placed around or near the detrusor innervations arising from the sacral spinal nerves, the light-responsive opsin proteins expressed on the plasma membranes of the detrusor innervations provoke depolarization-induced synaptic depletion of the neural cells, thereby preventing contraction of the detrusor muscle and permitting the bladder to fill. When the light-responsive opsin proteins expressed on the detrusor innervations arising from the sacral spinal nerves are not illuminated by the implantable light source, the detrusor muscle is able to contract due to the recovery of transynaptic vesicles and the pressure generated facilitates voiding. Similarly, when illuminated by an implantable light source placed around or near the external urinary sphincter innervations of the pudendal nerve, the light-responsive opsin proteins expressed on the plasma membranes of the external urinary sphincter innervations cause depolarization-induced synaptic depletion of those neurons, preventing contraction of the external urinary sphincter and permitting the individual to void. When the light-responsive opsin proteins expressed on the external urinary sphincter innervations of the pudendal nerve are not illuminated by the implantable light source, the external urinary sphincter contracts and permits the bladder to fill.

In some aspects, the individual externally controls the polarization state of the neurons responsible for the innervation of the detrusor muscle and/or neurons responsible for the innervation of the external urinary sphincter by activating the light means from one or more light sources (such as a light cuff) that surrounds or is located near one of the sacral spinal nerves (such as any of S1, S2, S3, S4, or S5) and/or the pudendal nerve. In another embodiment, the individual selectively changes the membrane polarization state of the neurons responsible for the innervation of the detrusor muscle and/or neurons responsible for the innervation of the external urinary sphincter by activating the light source surrounding or located near the pudendal nerve while simultaneously deactivating the light source surrounding or located near the sacral spinal nerves when the individual experiences the need and/or urge to void or wishes to void according to a predetermined schedule. In another embodiment, the individual is a human.

In some aspects, both the population of neurons responsible for the innervation of the detrusor muscle and the population of neurons responsible for the innervation of the external urinary sphincter muscle in the individual can be transfected with an expression vector comprising any of the polynucleotides described above. In some embodiments, the expression vector can be a viral vector such as any of the viral expression vectors described above. In some aspects, the population of neurons responsible for the innervation of the detrusor muscle can be transfected by injection of the expression vector into the somatic motor neuron cell body of a sacral spinal nerve (such as any of S1, S2, S3, S4, and/or S5). In other aspects, the population of neurons responsible for the innervation of the external urinary sphincter muscle is transfected by injection of the expression vector into Onuf's nucleus. In some aspects, one or more light sources (such as a light cuff) capable of generating light in response to an external signal, such as those described above, are surgically placed around or near the detrusor innervations arising from the sacral spinal nerves and around the external urinary sphincter innervations of the pudendal nerve.

Fecal Incontinence

Also, provided herein is a method for treating a fecal incontinence in an individual in need thereof, the method comprising administering an effective amount of a polynucleotide comprising a nucleotide sequence encoding a light-responsive opsin protein to the individual, wherein the light-responsive opsin protein is expressed on the plasma membrane of a population of neurons responsible for the innervation of the external anal sphincter muscle in the individual, wherein the light-responsive opsin protein is capable of inducing hyperpolarization of the neurons expressing the light-responsive protein in response to light, whereby the hyperpolarization of the neurons responsible for the innervation of the external anal sphincter muscle permits relaxation of the sphincter. Any polynucleotides described herein that encode a light-responsive opsin protein capable of inducing hyperpolarization may be administered. In other embodiments, the population of neurons responsible for the innervation of the external anal sphincter muscle are hyperpolarized by exposure to amber light.

When illuminated by an implantable light source (such as a light cuff) placed around or near the external anal sphincter innervations of the pudendal nerve and/or one or more sacral spinal nerves (such as any of S1, S2, S3, S4, and/or S5), the light-responsive opsin proteins expressed on the plasma membranes of the external anal sphincter innervations maintain a hyperpolarized neural membrane potential, preventing contraction of the external anal sphincter and permitting the individual to defecate. When the light-responsive opsin proteins expressed on the external anal sphincter innervations of the pudendal nerve and/or the sacral spinal nerves are not illuminated by the implantable light source, the external anal sphincter naturally contracts and permits the storage of stool in the bowel.

Also provided herein is a method for treating fecal incontinence in an individual in need thereof, the method comprising administering an effective amount of a polynucleotide comprising a nucleotide sequence encoding a light-responsive opsin protein to the individual, wherein the light-responsive opsin protein is expressed on the plasma membrane of a population of neurons responsible for the innervation of the of the external anal sphincter muscle in the individual, wherein the light-responsive opsin protein is capable of causing depolarization-induced synaptic depletion of the neurons expressing the light-responsive protein in response to light, whereby the depolarization-induced synaptic depletion of the neurons responsible for the innervation of the external anal sphincter muscle permits relaxation of the sphincter. Any polynucleotides described herein that encode a light-responsive opsin protein capable of inducing depolarization-induced synaptic depletion of the neurons may be administered. In other embodiments, the population of neurons responsible for the innervation of the external anal sphincter muscle can be depolarized to the point of synaptic depletion by exposure to blue, green, yellow, orange, or red light. In some embodiments, the light can have an intensity of at least about 100 Hz.

When illuminated by an implantable light source placed around or near the external anal sphincter innervations arising from the pudendal and/or sacral spinal nerves, the light-responsive opsin proteins expressed on the plasma membranes of the external anal sphincter innervations cause depolarization-induced synaptic depletion of those neurons, preventing contraction of the external anal sphincter and permitting the individual to defecate. When the light-responsive opsin proteins expressed on the external anal sphincter innervations of the pudendal nerve and/or the sacral spinal nerves are not illuminated by the implantable light source, the external anal sphincter naturally contracts and permits the rectum to store stool.

In some aspects, the individual externally controls the hyperpolarization state of the neurons responsible for the innervation of the external anal sphincter by activating the light means from one or more light sources (such as a light cuff) that surrounds or is located near the sacral spinal nerves and/or the pudendal nerve. In another embodiment, the individual selectively changes the membrane polarization state of the neurons responsible for the innervation of the external anal sphincter by activating the light source surrounding or located near the pudendal nerve and/or the sacral spinal nerves when the individual experiences the need and/or urge to defecate or wishes to defecate according to a predetermined schedule. In another embodiment, the individual is a human.

In some aspects, the population of neurons responsible for the innervation of the external anal sphincter muscle in the individual can be transfected with an expression vector comprising any of the polynucleotides described above. In some embodiments, the expression vector can be a viral vector such as any of the viral expression vectors described above. In some aspects, the population of neurons responsible for the innervation of the external anal sphincter muscle is transfected by injection of the expression vector into a sacral spinal nerve (such as any of S1, S2, S3, S4, and/or S5). In other aspects, the population of neurons responsible for the innervation of the external anal sphincter muscle is transfected by injection of the expression vector into the pudendal nerve or by injection of the expression vector into Onuf's nucleus. In some aspects, one or more light sources (such as a light cuff) capable of generating light in response to an external signal, such as those described above, are surgically placed around or near the external anal sphincter innervations arising from the pudendal nerve and/or the sacral spinal nerves.

Depolarization with Light-Responsive Opsin Proteins or Electrostimulation to Drive Muscular Contraction Bladder Dysfunction Sphincter muscles exist in a naturally contracted (tonic) state due to the fact that, unlike most skeletal muscles, there is no other muscle to oppose sphincter contraction (e.g., the biceps muscle is in opposition to the triceps muscle). However, in some situations, the cells or neurons located upstream of sites of sphincter muscle innervation may be damaged, nonfunctional, or unable to generate a muscle contraction strong enough to expel urine from the bladder, to close the external urinary sphincter, or to close the external anal sphincter. Under these circumstances, depolarization of these peripheral nerves via the use of light-responsive opsin proteins or traditional electrostimulation can be used to restore urinary function and/or fecal continence and achieve "on/off" control of the detrusor muscle, urinary sphincter, and/or anal sphincter, respectively.

Accordingly, provided herein is a method for treating a bladder dysfunction in an individual in need thereof, the method comprising administering effective amounts of polynucleotide sequences (such as any of the polynucleotide sequences disclosed above) encoding a first light-responsive opsin protein and a second light-responsive opsin protein to the individual, wherein the first light-responsive opsin protein and the second light-responsive opsin protein are expressed on the plasma membrane of a population of neurons responsible for the innervation of the detrusor muscle and/or a population of neurons responsible for the innervation of the external urinary sphincter muscle in the individual, wherein the first light-responsive opsin protein is capable of inducing hyperpolarization of the neurons expressing the first light-responsive protein in response to a first wavelength of light, whereby the hyperpolarization of the neurons responsible for the innervation of the detrusor muscle permits storage of urine in the bladder and the hyperpolarization of the neurons responsible for the innervation of the external urinary sphincter muscle permits voiding urine from the bladder, wherein the second light-responsive opsin protein is capable of inducing depolarization of the neurons expressing the second light-responsive protein in response to a second wavelength of light, whereby the depolarization of the neurons responsible for the innervation of the detrusor muscle permits voiding of urine from the bladder and the depolarization of the neurons responsible for the innervation of the external urinary sphincter muscle permits the closing of the sphincter permitting the storage of urine. In some embodiments, the bladder dysfunction is DH and/or DSD.

When illuminated by light having a first wavelength provided by an implantable light source (such as a light cuff) placed around or near the detrusor innervations arising from the sacral spinal nerves, the first light-responsive opsin proteins expressed on the plasma membranes of the detrusor innervations hyperpolarize the innervations, thereby preventing contraction of the detrusor muscle and permitting the bladder to fill. When the second light-responsive opsin proteins expressed on the detrusor innervations arising from the sacral spinal nerves are illuminated by light having a second wavelength provided by the implantable light source, the detrusor muscle is able to contract due to the depolarization of the detrusor innervations. Similarly, when illuminated by light having a first wavelength provided by an implantable light source (such as a light cuff) placed around or near the external urinary sphincter innervations of the pudendal nerve, the first light-responsive opsin proteins expressed on the plasma membranes of the external urinary sphincter innervations hyperpolarize those neurons, preventing contraction of the external urinary sphincter and permitting the individual to void. When the second light-responsive opsin proteins expressed on the external urinary sphincter innervations of the pudendal nerve are illuminated by light having a second wavelength provided by the implantable light source, the external urinary sphincter contracts due to depolarization of the innervations, permitting the storage of urine in the bladder.

Fecal Incontinence

Additionally, provided herein is a method for treating fecal incontinence in an individual in need thereof, the method comprising administering effective amounts of polynucleotide sequences (such as any of the polynucleotide sequences disclosed above) encoding a first light-responsive opsin protein and a second light-responsive opsin protein to the individual, wherein the first light-responsive opsin protein and the second light-responsive opsin protein are expressed on the plasma membrane of a population of neurons responsible for the innervation of the external anal sphincter muscle in the individual, wherein the first light-responsive opsin protein is capable of inducing hyperpolarization of the neurons expressing the first light-responsive protein in response to a first wavelength of light, whereby the hyperpolarization of the neurons responsible for the innervation of the external anal sphincter muscle permits relaxation of the sphincter permitting defecation, wherein the second light-responsive opsin is capable of inducing depolarization of the neurons expressing the second light-responsive protein in response to a second wavelength of light, whereby the depolarization of the neurons responsible for the innervation of the external anal sphincter muscle permits the closing of the sphincter permitting the storage of stool in the bowel.

When illuminated by light having a first wavelength provided by an implantable light source (such as a light cuff) placed around or near the innervations of the external anal sphincter arising from the pudendal nerve and/or the sacral spinal nerves, the first light-responsive opsin proteins expressed on the plasma membranes of the external anal sphincter innervations hyperpolarize the innervations, thereby preventing contraction of the sphincter muscle and permitting the sphincter to relax. When the second light-responsive opsin proteins expressed on the plasma membranes of the external anal sphincter innervations arising from the sacral spinal nerves and/or the pudendal nerve are illuminated by light having a second wavelength provided by the implantable light source, the sphincter muscle is able to contract due to the depolarization of the sphincter innervations, thereby permitting the storage of stool in the rectum.

In another aspect, the method for treating fecal incontinence further comprises administering an effective amount of a polynucleotide (such as any of the polynucleotide sequences disclosed above) comprising a nucleotide sequence encoding a light-responsive opsin protein to the individual, wherein the light-responsive opsin protein is expressed on the plasma membrane of a population of neurons responsible for the innervation of the muscles responsible for the contraction of the rectum in the individual, wherein the light-responsive opsin protein is capable of inducing depolarization of the neurons expressing the light-responsive protein in response to light, whereby the depolarization of the neurons responsible for the innervation of the muscles responsible for the contraction of the rectum facilitates defecation. In some aspects, the individual externally controls the depolarization state of the neurons responsible for the innervation of the muscles responsible for the contraction of the rectum by activating the light means from one or more light sources (such as a light cuff or any of the light sources described herein) that surrounds or is located near the sacral spinal nerves and/or nerve fibers arising from the inferior hypogastric plexus. In another embodiment, the individual selectively changes the membrane polarization state of the neurons responsible for the innervation of the muscles responsible for the contraction of the rectum by activating the light source surrounding or located near the sacral spinal nerves and/or nerve fibers arising from the inferior hypogastric plexus when the individual experiences the need and/or urge to defecate or wishes to defecate according to a predetermined schedule.

In other aspects, the method can also comprise electrical stimulation which can be used to depolarize the innervations of the detrusor muscle and/or the pudendal innervations of the external urinary sphincter as well as the innervations of the external anal sphincter. In some embodiments, an externally-controllable electrode is placed around or near the neurons responsible for the innervation of the detrusor muscle, the neurons responsible for the innervation of the external urinary sphincter, and/or the neurons responsible for the innervation of the external anal sphincter. In other embodiments, electrical stimulation can be used to depolarize the detrusor innervations arising from the sacral spinal nerves, resulting in the contraction of the detrusor muscle and the voiding of the urinary bladder while light-responsive opsin proteins can be used to hyperpolarize or cause depolarization-induced synaptic depletion of the detrusor innervations arising from the sacral spinal nerves, resulting in the relaxation of the detrusor muscle, thereby permitting the urinary bladder to fill. In another embodiment, electrical stimulation can be used to depolarize the external urinary sphincter innervations of the pudendal nerve, thereby closing the external urinary sphincter and permitting the bladder to fill while light-responsive opsin proteins can be used to hyperpolarize or cause depolarization-induced synaptic depletion of the external urinary sphincter innervations of the pudendal nerve, resulting in the relaxation of the external urinary sphincter, thereby permitting the urinary bladder to void.

Depolarization with Light-Responsive Opsin Proteins for Treating Sexual Dysfunction Also provided herein is a method for treating sexual dysfunction in an individual in need thereof, the method comprising administering an effective amount of a polynucleotide comprising a nucleotide sequence encoding a light-responsive opsin protein to the individual, wherein the light-responsive opsin protein is expressed on the plasma membrane of a population of neurons responsible for the innervation of the muscles and organs of the genitalia responsible for sexual function in the individual, wherein the light-responsive opsin protein is capable of causing depolarization of the neurons expressing the light-responsive protein in response to light, whereby the depolarization of the neurons responsible for the innervation of the genitalia permits sexual intercourse and/or sexual functionality in the individual. In some embodiments, sexual functionality is one or more functions selected from the group consisting of erection, orgasm, ejaculation, and vaginal lubrication. In other embodiments, sexual functionality is restoration of tactile sensations to the genitals needed to maintain sexual arousal. Any of the polynucleotides described herein that encode a light-responsive opsin protein capable of inducing depolarization of neurons may be administered. In other embodiments, the population of neurons can be depolarized to the point of synaptic depletion by exposure to blue, green, yellow, orange, or red light.

When illuminated by an implantable light source placed around or near the dorsal nerve of the penis/clitoris (a branch of the pudendal nerve) or the sacral spinal nerves, the light-responsive opsin proteins expressed on the plasma membranes of the dorsal nerve of the penis/clitoris cause depolarization of those neurons, leading to the contraction of those muscles and sensations and/or functions associated with normal sexual intercourse. These include, but are not limited to, erection, orgasm, ejaculation, and vaginal lubrication. Additionally, when illuminated by an implantable light source placed around or near the dorsal nerve of the penis/clitoris (a branch of the pudendal nerve) or the sacral spinal nerves, the light-responsive opsin proteins expressed on the plasma membranes of the dorsal nerve of the penis/clitoris cause depolarization of those neurons, leading to the restoration of tactile sensations to the genitals required to maintain sexual arousal.

In some aspects, the individual externally controls the depolarization of the neurons responsible for the innervation of the genitalia by activating the light means from one or more light sources that surrounds or is located near the pudendal nerve (such as the dorsal nerve of the penis/clitoris branch of the pudendal nerve) or the sacral spinal nerves. In another embodiment, the individual externally changes the polarization state of the neurons responsible for the innervation of the muscles of the genitalia by activating the light means from one or more light sources (such as a light cuff) that surrounds or is located near the pudendal nerve and/or the sacral spinal nerves when the individual experiences the desire to have sexual intercourse or when the individual chooses to have sexual intercourse according to a predetermined schedule. In another embodiment, the individual can be a human.

In some aspects, the population of neurons responsible for the innervation of the muscles and organs of the genitalia can be transfected by injection of a polynucleotide expression vector (such as any of the polynucleotide expression vector described above) into the somatic motor neuron cell body of a sacral spinal nerve (such as any of S1, S2, S3, S4, and/or S5). In other aspects, population of neurons responsible for the innervation of the muscles of the genitalia can be transfected by injection of the expression vector into the pudendal nerve. In some aspects, one or more light sources (such as a light cuff) capable of generating light in response to an external signal, such as those described above, can be surgically placed around or near the pudendal nerve (such as the dorsal nerve of the penis/clitoris branch of the pudendal nerve) or the sacral spinal nerves.

Kits

In some aspects, the present invention provides kits for treating a bladder dysfunction, fecal incontinence, and/or sexual dysfunction in an individual in need thereof. In some embodiments, the kit comprises a polynucleotide comprising a nucleotide sequence encoding a light-responsive ion pump protein, wherein the polynucleotide comprises a nucleotide sequence encoding an amino acid sequence comprising a sequence at least 95% identical to the sequence shown in SEQ ID NO:1, an ER export signal, and a membrane trafficking signal; and a cuff capable of generating light in response to an external signal, wherein the light is capable of activating the light-responsive ion pump protein.

In some aspects, the present invention provides kits for treating a bladder dysfunction, fecal incontinence, and/or sexual dysfunction in an individual in need thereof. In some embodiments, the kit comprises a polynucleotide comprising a nucleotide sequence encoding a light-responsive ion pump protein, wherein the polynucleotide comprises a nucleotide sequence encoding an amino acid sequence comprising a sequence at least 95% identical to the sequence shown in SEQ ID NO:4, an ER export signal, and a membrane trafficking signal; and a cuff capable of generating light in response to an external signal, wherein the light is capable of activating the light-responsive ion pump protein.

In some aspects, the present invention provides kits for treating a bladder dysfunction, fecal incontinence, and/or sexual dysfunction in an individual in need thereof. In some embodiments, the kit comprises a polynucleotide comprising a nucleotide sequence encoding a light-responsive ion pump protein, wherein the polynucleotide comprises a nucleotide sequence encoding an amino acid sequence comprising a sequence at least 95% identical to the sequence shown in SEQ ID NO:23, an ER export signal, and a membrane trafficking signal; and a cuff capable of generating light in response to an external signal, wherein the light is capable of activating the light-responsive ion pump protein.

In other aspects, the kit can further provide a set of instructions for administering an effective amount of the polynucleotide to the individual, wherein the light-responsive ion pump protein is expressed on the plasma membrane of a population of neurons responsible for the innervation of the detrusor muscle, a population of neurons responsible for the innervation of the external urinary sphincter muscle in the individual, and/or a population of neurons responsible for the innervation of the external anal sphincter muscle in the individual; and/or instructions for placing the cuff around the detrusor innervation of the sacral spinal nerves and/or around the external urinary sphincter innervation of the pudendal nerve, and/or around the external anal sphincter innervations of the pudendal nerve or the sacral spinal nerves. The kit can also provide instructions for using any of the light-responsive ion pump proteins described above according to any of the methods described above. Similarly, the light cuffs provided in the kit can be any of the light cuffs described above.

In some aspects, the present invention provides a kit for treating a bladder dysfunction in an individual in need thereof, where the kit comprises: a) a polynucleotide encoding a light-responsive opsin protein, wherein the polynucleotide comprises a nucleotide sequence encoding an amino acid sequence comprising a sequence at least 95% identical to one or more sequences selected from the group consisting of SEQ ID NO:4, SEQ ID NO:5, SEQ ID NO:6, SEQ ID NO:7, SEQ ID NO:8, SEQ ID NO:9, SEQ ID NO:10, and SEQ ID NO:11; and b) a light source capable of generating light in response to an external signal, wherein the light is capable of activating the opsin protein.

A subject kit can further include instructions for administering an effective amount of the polynucleotide to the individual, where the light-responsive opsin protein encoded by the polynucleotide is expressed on the plasma membrane of a population of neurons responsible for the innervation of the detrusor muscle and/or a population of neurons responsible for the innervation of the external urinary sphincter muscle in the individual; and instructions for placing the light source around the detrusor innervation of the sacral spinal nerve and/or around the external urinary sphincter innervation of the pudendal nerve. In some cases, the bladder dysfunction is detrusor hyperreflexia and/or detrusor-external sphincter dyssynergia.

In some aspects, the present invention provides a kit for treating fecal incontinence in an individual in need thereof, where the kit comprises: a) a polynucleotide encoding a light-responsive opsin protein, wherein the polynucleotide comprises a nucleotide sequence encoding the opsin protein comprising: i) a sequence at least 95% identical to the sequence shown in SEQ ID NO:1, SEQ ID NO:4, or SEQ ID NO:23; ii) an ER export signal; iii) and a membrane trafficking signal; and b) a light source capable of generating light in response to an external signal, wherein the light is capable of activating the opsin protein.

A subject kit can further include instructions for administering an effective amount of the polynucleotide to the individual, where the light-responsive opsin protein encoded by the polynucleotide is expressed on the plasma membrane of a population of neurons responsible for the innervation of the external anal sphincter muscle in the individual; and instructions for placing the light source around the external anal sphincter innervations of a sacral spinal nerve and/or the inferior hemorrhoidal branch of the pudendal nerve.

In some aspects, the present invention provides a kit for treating fecal incontinence in an individual in need thereof, where the kit comprises: a) a polynucleotide encoding a light-responsive opsin protein, where the polynucleotide comprises a nucleotide sequence encoding an amino acid sequence comprising a sequence at least 95% identical to one or more sequences selected from the group consisting of SEQ ID NO:4, SEQ ID NO:5, SEQ ID NO:6, SEQ ID NO:7, SEQ ID NO:8, SEQ ID NO:9, SEQ ID NO:10, and SEQ ID NO:11; and b) a light source capable of generating light in response to an external signal, wherein the light is capable of activating the opsin protein.

The kit can further include instructions for administering an effective amount of the polynucleotide to the individual, wherein the light-responsive opsin protein encoded by the polynucleotide is expressed on the plasma membrane of a population of neurons responsible for the innervation of the external anal sphincter muscle in the individual; and instructions for placing the light source around the external anal sphincter innervations of a sacral spinal nerve and/or the inferior hemorrhoidal branch of the pudendal nerve.

In some aspects, the present invention provides a kit for treating sexual dysfunction in an individual in need thereof, where the kit comprises: a) a polynucleotide encoding a light-responsive opsin protein, wherein the polynucleotide comprises a nucleotide sequence encoding an amino acid sequence comprising a sequence at least 95% identical to one or more sequences selected from the group consisting of SEQ ID NO:5, SEQ ID NO:6, SEQ ID NO:7, SEQ ID NO:8, SEQ ID NO:9, SEQ ID NO:10, and SEQ ID NO:11; and b) a light source capable of generating light in response to an external signal, where the light is capable of activating the opsin protein.

The kit can further include instructions for administering an effective amount of the polynucleotide to the individual, where the light-responsive opsin protein encoded by the polynucleotide is expressed on the plasma membrane of a population of neurons responsible for the innervation of the genitalia in the individual; and instructions for placing the light source around the genital innervations arising from one or more sacral spinal nerves, the dorsal nerve of the penis branch of the pudendal nerve, and/or the dorsal nerve of the clitoris branch of the pudendal nerve.

EXAMPLES

Example 1

Use of Optogenetic-Based Nerve Stimulation in an Animal Model of Detrusor External Sphincter Dysnergia (DSD) and Detrusor Hyperreflexia (DH)

This Example validates an animal model of DSD and DH for treatment with the optogenetic methods described herein. Cat models with spinal cord injuries have been used to recreate the human conditions of DSD and DH, having been validated using PET (Tai et al., 2004, *Experimental Neurol.*, 190:171). There are also animal models of hyperreflexia in spinal cord injured (SCI) rats (Shaker et al., 2003, *Neurourol Urodyn.*, 22(7):693-8) as well as in the EAE mouse, which is also a model for multiple sclerosis (Vignes et al., 2007, *J. Physio.* 578(Pt 2):439-50). In this Example, the membrane-targeted photoactivateable anion pump halorhodopsin from *Natronomonas pharaonis* (NpHR) is used to hyperpolarize the nerves responsible for the innervation of the detrusor muscle of the bladder and the external urinary sphincter.

Materials and Methods

Cats with experimentally induced spinal cord injuries to replicate symptoms of human DSD and DH are produced according to known methods (Tai et al., 2004, *Experimental Neurol.* 190:171). Yellow fluorescent protein (YFP)-labeled Halorhodopsin (YFP-NpHr3.0, and/or YFP-NpHR3.1; see www(dot)optogenetics(dot)org) in an AAV1 viral vector and under control of the feline Thy1 promoter is injected directly into the somatic motor neuron cell body of the sacral spinal nerves responsible for detrusor innervations. Additionally, YFP-halorhodopsin in an AAV1 viral vector under control of the feline Thy1 promoter is injected into Onuf's nucleus, the origin of the pudendal nerve.

Light Cuff Construction and Surgical Implantation

Light cuff construction uses a 0.5 mm interior diameter borosilicate glass pipette. The glass pipettes is carefully ground to 4 mm and an approximately 0.5 mm wide channel is ground longitudinally along the length of the cuff using a dental drill with an abrasive tip. Ultraviolet-curing epoxy (Norland Products, Cranbury, N.J., NOA 81) is applied to the outside of the cuff and cured with a UV curing lamp. Sixteen small (1.0×0.6×0.2 mm) amber LEDs (Rohm, Kyoto, Japan, SMLP12BC7T, 589 nm) are applied to the exterior of the glass cuff and secured in place with the UV-cured optical epoxy. LEDs are arranged in a concentric perimeter facing the peripheral nerve in the center and micro-soldered by hand using 40 gauge copper magnet wire. Intensity and on/off times of single LEDs are measured with a digital optical power meter and a high-speed photo-detector (ThorLabs, Newton, N.J., S130A and DET10A). Intensity measurements are used as inputs for a light propagation model, described below, and serve to construct an electrical input current vs. light intensity plot for estimation of experimental light.

The externally-activatable light cuff with light emitting diode (LED) is surgically placed so as to encircle each nerve (one or more sacral spinal nerve and/or the pudendal nerve; see, e.g., Llewellyn et al., 2010, *Nat. Med.*, 16(10):161-165).

Light Propagation Model

A light propagation model is used to verify that all regions of the detrusor innervations arising from the sacral spinal nerves as well as the external urinary sphincter innervations of the pudendal nerve (or the pudendal nerve itself) are exposed to light intensities that exceeded that minimum light intensity required to activate NpHr3.0, and/or NpHR3.1 chloride pumps (3.5 mW/mm$^{-2}$; Gradinaru et al., 2010, *Cell*, 141:1-12). Light propagation is modeled using the Kubelka-Munk model as outlined in Aravanis et al. for diffuse scattering tissue (2007, *J Neural Eng* 4, S143-56). Briefly, the light intensity varies with distance by the equation $$\frac{I_{(z)}}{I_{(z=0)}} = \frac{\rho^2}{(Sz+1)(z+\rho)}$$

where $$\rho = r\sqrt{\left(\frac{n}{NA}\right)^2 - 1}$$

and S was the scattering length of the tissue, z was the distance from the light source, r was the diameter of the LED chip, n was the refractive index of the material the light was traversing, NA was the numerical aperture of the LED from $$NA = n \sin \theta_{\frac{1}{2}}$$

and ½ was the half angle of divergence from the LED. This model takes into account the effect on light intensity due to scattering and geometrical losses. The value used for scattering length is empirically determined from mouse brain slices for wavelengths between 400 and 900 nm, and assumed to be similar in peripheral tissue. This model also assumes no losses in light intensity due to absorption, nor does it take into account multiply scattering photons. Values for ½ and r are taken from the LED manufacturer's product sheet, while I(z=0) was measured with a power meter (ThorLabs, Newton, N.J., S130A) for a single LED.

Using a pudendal nerve diameter as a reference in this model, relative optical intensity variation can be determined on the nerve periphery and at the nerve center. Any drop in intensity across the nerve can therefore be determined as well as the minimum surface of the nerve required to exceed the minimal intensity for light activation of NpHr3.0, and/or NpHR3.1 chloride pumps (3.5 mW/mm$^{-2}$). The light cuff is capable of exceeding 25 mW mm$^{-2}$ at the surface of the nerve.

Motor Axon Imaging of the Pudendal Nerve and Sacral Spinal Nerves

Adult spinal cord-injured cats, prepared as described above, are anesthetized by injection of ketamine and xylazine. The detrusor muscle and/or external urinary sphincter muscles are exposed by incision in the skin followed by intramuscular injection of 4 µl of 5% retrograde labeling dye (Fast Blue, Polysciences, Warrington, Pa.). The skin incision is closed by a tissue adhesive (VetBond, 3M, St. Paul, Minn.), and cats are allowed to recover. After one week, animals are anesthetized and sacrificed. Pudendal and sacral spinal nerve sections are dissected and fixed in 4% paraformaldehyde for 30 min at 25° C. Samples are then washed twice in 1X phosphate-buffered saline (in mM, 2.7 KCl, 1.76 KH2PO4, 137 NaCl, 10 NaHPO4, pH 7.4) for 5 min each at 25° C., embedded in 50° C. lowmelting point agarose, and vibratome sliced into 50 µm sections.

Following a 30 min permeabilization in 0.1% Triton X-100 (octylphenolpoly(ethyleneglycolether)x) and 3% normal donkey serum, sections are incubated overnight with mouse monoclonal anti-lamin 1:500 (Abcam, Cambridge, Mass.) and rabbit polyclonal anti-tau 1:1000 (DAKO, Cambridgeshire, UK). Sections are then washed and incubated for 3 hrs at 25° C. with fluorescent Cy3- or Cy5-conjugated secondary antibodies 1:1000 (Jackson Laboratories, West Grove, Pa.). Confocal fluorescence images are acquired using a Leica TCS SP5 scanning laser microscope (Leica Microsystems GmbH, Wetzlar, Germany) with a 20X/0.70NA or 40X /1.25NA oil immersion objective. Multiple serial stack images across several subjects are acquired using equivalent settings.

Image Analysis

The number, size, and fluorescence intensity of motor axons (3 μm and G-ratio 0.5) are determined by manual analysis using ImageJ software (NIH, Bethesda, Md.). The perimeter of lamin-labeled myelin sheath and tau-labeled axolemma are outlined by hand to form a region of interest. The Feret's diameter and average pixel intensity was then automatically determined in ImageJ for the region of interest. The axon depth within the pudendal and sacral spinal nerves are determined by finding the shortest distance between the center of each axon and the exterior of the nerve. Motor axon diameter vs. pixel intensity of yellow fluorescent protein are tested for statistically significant correlation using a paired two-tailed Student's t-test ($\alpha=0.05$) after first testing for normality using Lilliefors test ($\alpha=0.05$) in Matlab (Mathworks, Natick, Mass.).

The distribution of the YFP-tagged light-responsive chloride pumps within motor axons of a Thy1::NpHR cat are quantified by examining cross-sections of the pudendal and sacral spinal nerves both parallel and perpendicular to the long axis of the axons.

Stimuli provided via the light cuffs evoke electrical and contractile responses of the detrusor muscle and the external urinary sphincter.

An external signal is used to activate the LEDs. The activation of the sacral spinal LEDs and the pudental LEDs are such that when one is on, the other is off. When the sacral spinal LEDs are on, the bladder is relaxed and the external urinary sphincter is active, allowing for the storage of urine. When the sacral spinal LEDs are off, the external urinary sphincter is on allowing the external urinary sphincter to relax and allow the urine to pass from the contracting bladder. When voiding is complete, the sacral spinal LEDs are turned back on with external urinary sphincter LEDs being turned off.

Example 2

Use of Light-Responsive Cation Channels to Provoke Depolarization-Induced Synaptic Depletion in an Animal Model of Detrusor External Sphincter Dysnergia (DSD) and Detrusor Hyperreflexia (DH)

This Example validates an animal model of DSD and DH for treatment with the optogenetic methods described above whereby urinary function is restored via selective depolarization-induced synaptic depletion of the detrusor innervations arising from the sacral spinal nerves and the external urinary sphincter innervations of the pudendal nerve. The feline or rodent animal models are identical to those used in Example 1.

Yellow fluorescent protein (YFP)-labeled SSFO (pAAV-Thy1-hChR2 (E123T/T159C)-EYFP; see www(dot)optogenetics(dot)org) in an AAV1 viral vector and under control of the feline Thy1 promoter is injected directly into the somatic motor neuron cell body of the sacral spinal nerves (responsible for detrusor innervations) and into Onuf's nucleus (responsible for external urinary sphincter innervations).

Light cuffs are manufactured as in Example 1. The externally-activatable light cuffs with light emitting diode (LED) are surgically placed so as to encircle the detrusor innervations arising from the sacral spinal nerves and the external urinary sphincter innervations of the pudendal nerve. The depolarization-induced synaptic depletion caused by activation of the light-responsive cation channel proteins with light having an intensity of at least 100 Hz evokes the relaxation of the detrusor muscle, thereby permitting the bladder to fill. Additionally, the depolarization-induced synaptic depletion caused by activation of the light-responsive cation channel proteins with light having an intensity of at least 100 Hz causes the relaxation of the external urinary sphincter, thereby permitting voiding of urine.

An external signal is used to activate the LEDs. The activation of the sacral spinal LEDs and the pudental LEDs are such that when one is on, the other is off. When the sacral spinal LEDs are on, the bladder is relaxed and the external urinary sphincter is active, allowing for the storage of urine. When the sacral spinal LEDs are off, the external urinary sphincter is on allowing the external urinary sphincter to relax and allow the urine to pass from the contracting bladder. When voiding is complete, the sacral spinal LEDs are turned back on with external urinary sphincter LEDs being turned off.

Example 3

AAV Vector Constructs

The following Adenoassociated virus (AAV) constructs were generated: 1) AAV1:hsyn-ChR2-EYFP (AAV1 comprising a nucleotide sequence encoding a ChR2-eYFP fusion protein operably linked to a human synapsin 1 promoter); 2) AAV6-hsyn-ChR2-EYFP (AAV6 comprising a nucleotide sequence encoding a ChR2-eYFP fusion protein operably linked to a human synapsin 1 promoter); 3) AAV1-hsyn-NpHR-EYFP (AAV1 comprising a nucleotide sequence encoding an NpHR 3.0-EYFP fusion protein, operably linked to a human synapsin 1 promoter); 4) AAV6-hsyn-NpHR-EYFP (AAV6 comprising a nucleotide sequence encoding an NpHR 3.0-EYFP fusion protein, operably linked to a human synapsin 1 promoter); 5) AAV1-hsyn-eARCH-EYFP (AAV1 comprising a nucleotide sequence encoding an eARCH 3.0-EYFP fusion protein, operably linked to a human synapsin 1 promoter).

Single-stranded DNA AAV viruses were produced in a baculovirus system (Virovek, Hayward, Calif.; as described in WO 2008/024998

Example 4

Intramuscular Injections of AAV Encoding Opsins in Rat

A total dose of about $1\times10^{12}$ viral genomes (vg) in about 12 μL of constructs described in Example 3 was injected into the EUS muscle of female F344/Sprague Dawley rats, 130-170 g each. At various numbers of days after injection, animals were sacrificed, and expression of the opsins encoded by the constructs in the dorsolateral nucleus (DLN), and other regions of the spinal cord, was assessed. FIG. 1 depicts schematically the various sections of the spinal cord, including the DLN. All constructs encoded opsin-EYFP fusion proteins (e.g., ChR2-EYFP; NpHR-EYFP; eARCH-EYFP).

40 nm sections of the rat spinal cord were prepared. Sections were stained with DAPI and examined with a fluorescence microscope. Confocal microscopy was used to count DLN motor neurons on all sections by visualizing YFP labeling. Motor neurons were visualized using a 40× objective, and photomicrographs for sections were taken by merging images from DAPI (depicting the nucleus) and YFP (indicating regions of the cell body) channels. Sections with a visible nucleus surrounded by YFP within the DLN were counted over serial sections to determine total motor neuron counts for each animal. In each section, cells were counted as positive if they showed both YFP expression and DAPI for nuclear staining. The data are depicted in FIG. 2.

Figure 2:
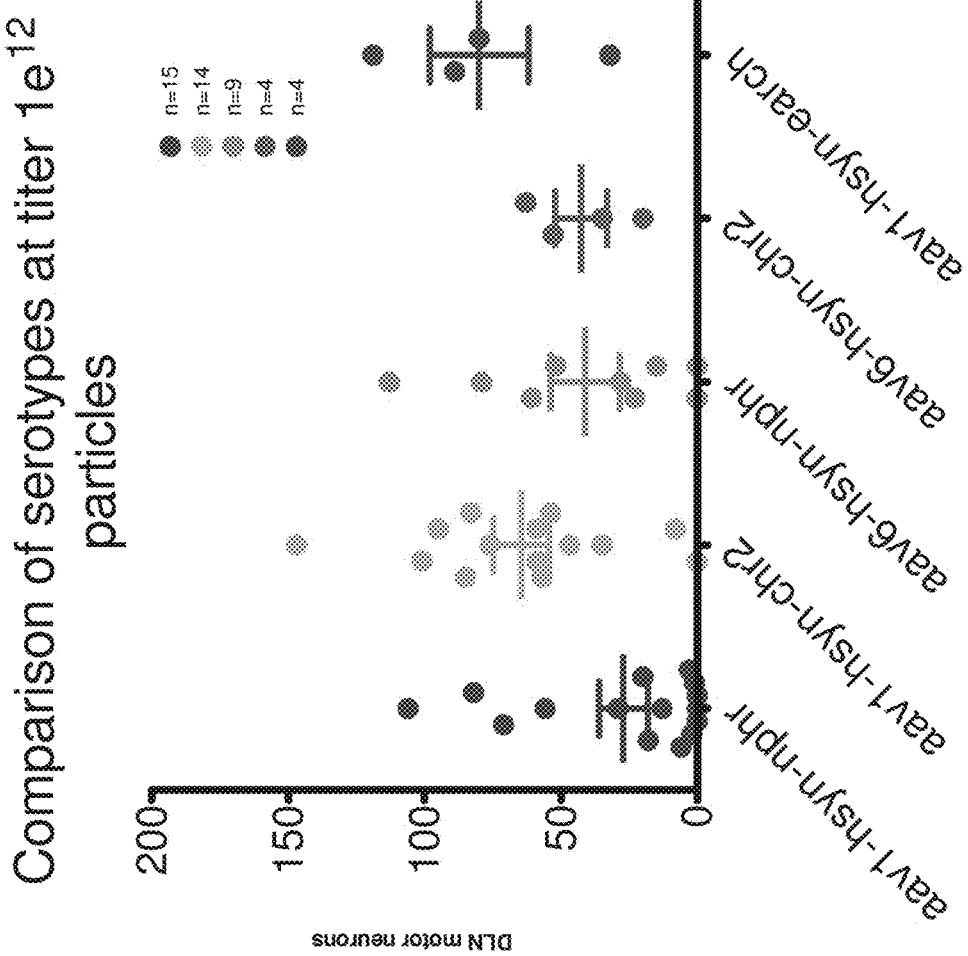
FIG. 2 depicts numbers of external urinary sphincter (EUS) pudendal motor neurons expressing AAV construct-encoded opsins.

As shown in FIG. 2, left panel, approximately half of all the pudendal motor neurons expressed protein encoded by the various injected AAV constructs. Literature values for total number of pudendal motor neurons as measured by retrograde labeling is approximately 60 for DL right and DL left, and 120 total. (Kane et al. (2002) *Anat. Rec.* 266:21-29).

Example 5

Measuring Contraction of EUS Muscle and Bladder Pressure in Rat 90 days after AAV1-hsyn-ChR2-EYFP intramuscular injection into the EUS, cystometry and sphincter-EMG recordings of the bladder and external urinary sphincter were performed. Cystometry involved placing a catheter in the rodent bladder that is hooked to a pressure sensor. Electrodes were placed in the EUS and hooked up to a recording amplifier to measure sphincter muscle contraction (EMG) activity. The data are presented in FIG. 3.

Figure 3:
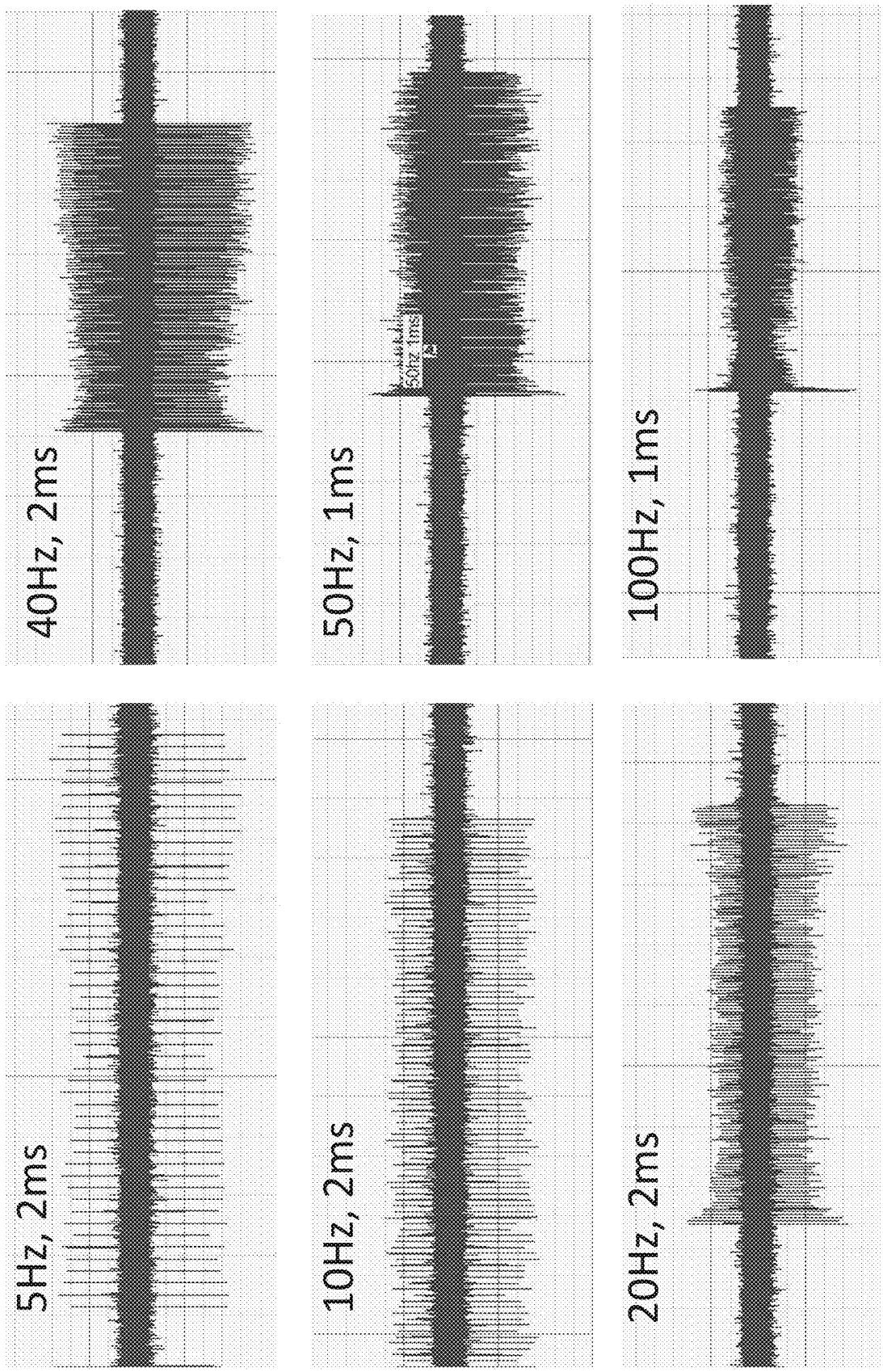
FIG. 3 depicts optical stimulation of pudendal nerve expressing ChR2.

FIG. 3 shows EUS muscle contractions at different frequencies/time durations after blue light optical stimulation at the pudendal nerve of rats intramuscularly (into the EUS) injected with AAV1-hsyn-ChR2-EYFP. Observed optically-induced contractions follow the frequency of light pulses from 5-50 Hz for the pudendal nerve.

The examples, which are intended to be purely exemplary of the invention and should therefore not be considered to limit the invention in any way, also describe and detail aspects and embodiments of the invention discussed above. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

SEQUENCES

The amino acid sequence of NpHR without the signal peptide:

(SEQ ID NO: 1)
VTQRELFEFVLNDPLLASSLYINIALAGLSILLFVFMTRGLDDPRAKLI

AVSTILVPVVSIASYTGLASGLTISVLEMPAGHFAEGSSVMLGGEEVDG

VVTMWGRYLTWALSTPMILLALGLLAGSNATKLFTAITFDIAMCVTGLA

AALTTSSHLMRWFWYAISCACFLVVLYILLVEWAQDAKAAGTADMFNTL

KLLTVVMWLGYPIVWALGVEGIAVLPVGVTSWGYSFLDIVAKYIFAFLL

LNYLTSNESVVSGSILDVPSASGTPADD.

The amino acid sequence of eYFP-NpHR3.0:

(SEQ ID NO: 2)
MTETLPPVTESAVALQAEVTQRELFEFVLNDPLLASSLYINIALAGLSI

LLFVFMTRGLDDPRAKLIAVSTILVPVVSIASYTGLASGLTISVLEMPA

GHFAEGSSVMLGGEEVDGVVTMWGRYLTWALSTPMILLALGLLAGSNAT

KLFTAITFDIAMCVTGLAAALTTSSHLMRWFWYAISCACFLVVLYILLV

EWAQDAKAAGTADMFNTLKLLTVVMWLGYPIVWALGVEGIAVLPVGVTS

WGYSFLDIVAKYIFAFLLLNYLTSNESVVSGSILDVPSASGTPADDAAA

KSRITSEGEYIPLDQIDINVVSKGEELFTGVVPILVELDGDVNGHKFSV

SGEGEGDATYGKLTLKFICTTGKLPVPWPTLVTTFGYGLQCFARYPDHM

KQHDFFKSAMPEGYVQERTIFFKDDGNYKTRAEVKFEGDTLVNRIELKG

IDFKEDGNILGHKLEYNYNSHNVYIMADKQKNGIKVNFKIRHNIEDGSV

QLADHYQQNTPIGDGPVLLPDNHYLSYQSALSKDPNEKRDHMVLLEFVT

AAGITLGMDELYKFCYENEV.

The amino acid sequence of eYFP-NpHR3.1:

(SEQ ID NO: 3)
MVTQRELFEFVLNDPLLASSLYINIALAGLSILLFVFMTRGLDDPRAKL

IAVSTILVPVVSIASYTGLASGLTISVLEMPAGHFAEGSSVMLGGEEVD

GVVTMWGRYLTWALSTPMILLALGLLAGSNATKLFTAITFDIAMCVTGL

AAALTTSSHLMRWFWYAISCACFLVVLYILLVEWAQDAKAAGTADMFNT

LKLLTVVMWLGYPIVWALGVEGIAVLPVGVTSWGYSFLDIVAKYIFAFL

LLNYLTSNESVVSGSILDVPSASGTPADDAAAKSRITSEGEYIPLDQID

INVVSKGEELFTGVVPILVELDGDVNGHKFSVSGEGEGDATYGKLTLKF

ICTTGKLPVPWPTLVTTFGYGLQCFARYPDHMKQHDFFKSAMPEGYVQE

RTIFFKDDGNYKTRAEVKFEGDTLVNRIELKGIDFKEDGNILGHKLEYN

YNSHNVYIMADKQKNGIKVNFKIRHNIEDGSVQLADHYQQNTPIGDGPV

LLPDNHYLSYQSALSKDPNEKRDHMVLLEFVTAAGITLGMDELYKFCYE

NEV.

The amino acid sequence of GtR3:

(SEQ ID NO: 4)
ASSFGKALLEFVFIVFACITLLLGINAAKSKAASRVLFPATFVTGIAS

AYFSMASGGGWVIAPDCRQLFVARYLDWLITTPLLLIDLGLVAGVSRW

DIMALCLSDVLMIATGAFGSLTVGNVKWVWWFFGMCWFLHIIFALGKS

WAEAAKAKGGDSASVYSKIAGITVITWFCYPVVWVFAEGFGNFSVTFE

VLIYGVLDVISKAVFGLILMSGAATGYESI.

The amino acid sequence of ChR2:

(SEQ ID NO: 5)
MDYGGALSAVGRELLFVTNPVVVNGSVLVPEDQCYCAGWIESRGTNGA
QTASNVLQWLAAGFSILLLMFYAYQTWKSTCGWEEIYVCAIEMVKVIL
EFFFEFKNPSMLYLATGHRVQWLRYAEWLLTCPVILIHLSNLTGLSND
YSRRTMGLLVSDIGTIVWGATSAMATGYVKVIFFCLGLCYGANTFFHA
AKAYIEGYHTVPKGRCRQVVTGMAWLFFVSWGMFPILFILGPEGFGVL
SVYGSTVGHTIIDLMSKNCWGLLGHYLRVLIHEHILIHGDIRKTTKLN
IGGTEIEVETLVEDEAEAGAVP.

The amino acid sequence of SFO:

(SEQ ID NO: 6)
MDYGGALSAVGRELLFVTNPVVVNGSVLVPEDQCYCAGWIESRGTNG
AQTASNVLQWLAAGFSILLLMFYAYQTWKSTCGWEEIYVCAIEMVKV
ILEFFFEFKNPSMLYLATGHRVQWLRYAEWLLTSPVILIHLSNLTGL
SNDYSRRTMGLLVSDIGTIVWGATSAMATGYVKVIFFCLGLCYGANT
FFHAAKAYIEGYHTVPKGRCRQVVTGMAWLFFVSWGMFPILFILGPE
GFGVLSVYGSTVGHTIIDLMSKNCWGLLGHYLRVLIHEHILIHGDIR
KTTKLNIGGTEIEVETLVEDEAEAGAVP.

The amino acid sequence of SSFO:

(SEQ ID NO: 7)
MDYGGALSAVGRELLFVTNPVVVNGSVLVPEDQCYCAGWIESRGTN
GAQTASNVLQWLAAGFSILLLMFYAYQTWKSTCGWEEIYVCAIEMV
KVILEFFFEFKNPSMLYLATGHRVQWLRYAEWLLTSPVILIHLSNL
TGLSNDYSRRTMGLLVSAIGTIVWGATSAMATGYVKVIFFCLGLCY
GANTFFHAAKAYIEGYHTVPKGRCRQVVTGMAWLFFVSWGMFPILF
ILGPEGFGVLSVYGSTVGHTIIDLMSKNCWGLLGHYLRVLIHEHIL
IHGDIRKTTKLNIGGTEIEVETLVEDEAEAGAVP.

The amino acid sequence of C1V1:

(SEQ ID NO: 8)
MSRRPWLLALALAVALAAGSAGASTGSDATVPVATQDGPDYVFHRA
HERMLFQTSYTLENNGSVICIPNNGQCFCLAWLKSNGTNAEKLAAN
ILQWITFALSALCLMFYGYQTWKSTCGWEEIYVATIEMIKFIIEYF
HEFDEPAVIYSSNGNKTVWLRYAEWLLTCPVLLIHLSNLTGLKDDY
SKRTMGLLVSDVGCIVWGATSAMCTGWTKILFFLISLSYGMYTYFH
AAKVYIEAFHTVPKGICRELVRVMAWTFFVAWGMFPVLFLLGTEGF
GHISPYGSAIGHSILDLIAKNMWGVLGNYLRVKIHEHILLYGDIRK
KQKITIAGQEMEVETLVAEEED.

The amino acid sequence of C1V1 (E122T):

(SEQ ID NO: 9)
MSRRPWLLALALAVALAAGSAGASTGSDATVPVATQDGPDYVFHR
AHERMLFQTSYTLENNGSVICIPNNGQCFCLAWLKSNGTNAEKLA
ANILQWITFALSALCLMFYGYQTWKSTCGWETIYVATIEMIKFII
EYFHEFDEPAVIYSSNGNKTVWLRYAEWLLTCPVLLIHLSNLTGL
KDDYSKRTMGLLVSDVGCIVWGATSAMCTGWTKILFFLISLSYGM
YTYFHAAKVYIEAFHTVPKGICRELVRVMAWTFFVAWGMFPVLFL
LGTEGFGHISPYGSAIGHSILDLIAKNMWGVLGNYLRVKIHEHIL
LYGDIRKKQKITIAGQEMEVETLVAEEED.

The amino acid sequence of C1V1 (E162T):

(SEQ ID NO: 10)
MSRRPWLLALALAVALAAGSAGASTGSDATVPVATQDGPDYVFHRAHER
MLFQTSYTLENNGSVICIPNNGQCFCLAWLKSNGTNAEKLAANILQWIT
FALSALCLMFYGYQTWKSTCGWEEIYVATIEMIKFIIEYFHEFDEPAVI
YSSNGNKTVWLRYATWLLTCPVLLIHLSNLTGLKDDYSKRTMGLLVSDV
GCIVWGATSAMCTGWTKILFFLISLSYGMYTYFHAAKVYIEAFHTVPKG
ICRELVRVMAWTFFVAWGMFPVLFLLGTEGFGHISPYGSAIGHSILDLI
AKNMWGVLGNYLRVKIHEHILLYGDIRKKQKITIAGQEMEVETLVAEEE
D.

The amino acid sequence of C1V1 (E122T/E162T):

(SEQ ID NO: 11)
MSRRPWLLALALAVALAAGSAGASTGSDATVPVATQDGPDYVFHRAHER
MLFQTSYTLENNGSVICIPNNGQCFCLAWLKSNGTNAEKLAANILQWIT
FALSALCLMFYGYQTWKSTCGWETIYVATIEMIKFIIEYFHEFDEPAVI
YSSNGNKTVWLRYATWLLTCPVLLIHLSNLTGLKDDYSKRTMGLLVSDV
GCIVWGATSAMCTGWTKILFFLISLSYGMYTYFHAAKVYIEAFHTVPKG
ICRELVRVMAWTFFVAWGMFPVLFLLGTEGFGHISPYGSAIGHSILDLI
AKNMWGVLGNYLRVKIHEHILLYGDIRKKQKITIAGQEMEVETLVAEEE
D.

The amino acid sequence of eArch:

(SEQ ID NO: 23)
MDPIALQAGYDLLGDGRPETLWLGIGTLLMLIGTFYFLVRGWGVTDKD
AREYYAVTILVPGIASAAYLSMFFGIGLTEVTVGGEMLDIYYARYADW
LFTTPLLLLDLALLAKVDRVTIGTLVGVDALMIVTGLIGALSHTAIAR
YSWWLFSTICMIVVLYFLATSLRSAAKERGPEVASTFNTLTALVLVLW
TAYPILWIIGTEGAGVVGLGIETLLFMVLDVTAKVGFGFILLRSRAIL
GDTEAPEPSAGADVSAAD.

The amino acid sequence of eArch3.0-EYFP:

(SEQ ID NO: 24)
MDPIALQAGYDLLGDGRPETLWLGIGTLLMLIGTFYFLVRGWGVTDKD
AREYYAVTILVPGIASAAYLSMFFGIGLTEVTVGGEMLDIYYARYADW
LFTTPLLLLDLALLAKVDRVTIGTLVGVDALMIVTGLIGALSHTAIAR
YSWWLFSTICMIVVLYFLATSLRSAAKERGPEVASTFNTLTALVLVLW
TAYPILWIIGTEGAGVVGLGIETLLFMVLDVTAKVGFGFILLRSRAIL
GDTEAPEPSAGADVSAADRPVVAVSKAAAKSRITSEGEYIPLDQIDIN
VVSKGEELFTGVVPILVELDGDVNGHKFSVSGEGEGDATYGKLTLKFI
CTTGKLPVPWPTLVTTFGYGLQCFARYPDHMKQHDFFKSAMPEGYVQE
RTIFFKDDGNYKTRAEVKFEGDTLVNRIELKGIDFKEDGNILGHKLEY
NYNSHNVYIMADKQKNGIKVNFKIRHNIEDGSVQLADHYQQNTPIGDG
PVLLPDNHYLSYQSALSKDPNEKRDHMVLLEFVTAAGITLGMDELYKF
CYENEV.

---

We claim:

1. A method for expressing a first light-responsive opsin protein and a second light-responsive opsin protein in a population of motor neurons responsible for innervation of the detrusor muscle or a population of motor neurons responsible for the innervation of the external urinary sphincter muscle in an individual in need thereof, the method comprising:
   i) directly injecting into a somatic motor neuron cell body of a sacral spinal nerve, a pudendal nerve, or into Onuf's nucleus of the individual:
   an effective amount of a first recombinant viral vector comprising a nucleotide sequence encoding the first light-responsive opsin protein, wherein the nucleotide sequence is operably linked to a neuron-specific promoter, and wherein the nucleotide sequence encoding the first light-responsive opsin protein comprises:
      (a) the amino acid sequence as set forth in SEQ ID NO: 1;
      (b) an ER export signal; and
      (c) a membrane trafficking signal, and
   an effective amount of a second recombinant viral vector comprising a nucleotide sequence encoding a second light-responsive opsin protein, wherein the nucleotide sequence is operably linked to a neuron-specific promoter, and wherein the nucleotide sequence encoding the second light-responsive opsin protein comprises:
      (a) the amino acid sequence as set forth in SEQ ID NO:5;
      (b) an ER export signal; and
      (c) a membrane trafficking signal,
   wherein said injecting provides for expression of the first light-responsive opsin protein and the second light-responsive opsin protein in the population of motor neurons responsible for innervation of the detrusor muscle or the population of motor neurons responsible for the innervation of the external urinary sphincter muscle;
   ii) implanting a light emitting device near the population of motor neurons responsible for the innervation of the detrusor muscle or the population of motor neurons responsible for the innervation of the external urinary sphincter muscle; and
   iii) activating the light emitting device to emit a first wavelength of light to activate the first light-responsive opsin protein expressed in the population of motor neurons responsible for innervation of the detrusor muscle or for the innervation of the external urinary sphincter muscle in an individual or a second wavelength of light to activate the second light-responsive opsin protein expressed in the population of motor neurons responsible for innervation of the detrusor muscle or for the innervation of the external urinary sphincter muscle in an individual,
   wherein said activation of the first light-responsive opsin protein expressed in the population of motor neurons responsible for innervation of the detrusor muscle induces hyperpolarization of the population of motor neurons responsible for the innervation of the detrusor muscle to permit storage of urine in the bladder or,
   wherein said activation of the first light-responsive opsin protein expressed in the population of motor neurons responsible for the innervation of the external urinary sphincter muscle induces hyperpolarization of the population of motor neurons responsible for the innervation of the external urinary sphincter muscle to permit voiding urine from the bladder or,
   wherein said activation of the second light-responsive opsin protein expressed in the population of motor neurons responsible for innervation of the detrusor muscle induces depolarization of the population of motor neurons responsible for the innervation of the detrusor muscle to permit voiding urine from the bladder, or
   wherein said activation of the second light-responsive opsin protein expressed in the population of motor neurons responsible for the innervation of the external urinary sphincter muscle induces depolarization of the population of motor neurons responsible for the innervation of the external urinary sphincter muscle to permit storage of urine in the bladder.

2. The method of claim 1, wherein the population of motor neurons responsible for the innervation of the detrusor muscle are neurons arising from one or more sacral spinal nerves in the individual.

3. The method of claim 1, wherein the population of motor neurons responsible for the innervation of the external urinary sphincter muscle comprises neurons of the pudendal nerve in the individual.

4. The method of claim 1, wherein the light-emitting device is around the detrusor innervations arising from the sacral spinal nerves and/or around the external urinary sphincter innervations of the pudendal nerve.

5. The method of claim 4, wherein the individual externally controls the polarization state of the neurons responsible for the innervation of the detrusor muscle and/or neurons responsible for the innervation of the external urinary sphincter by activating the light-emitting device.

6. The method of claim 1, wherein the first and second recombinant viral vectors are directly injected into the somatic motor neuron cell body of the sacral spinal nerve.

7. The method of claim 1, wherein the first and second recombinant viral vectors are directly injected into the pudendal nerve, or into Onuf's nucleus.

8. The method according to claim 1, wherein the first or second light-responsive opsin protein comprises a signal peptide.

9. The method according to claim 1, wherein the ER export signal comprises the amino acid sequence as set forth in SEQ ID NO:21.

10. The method according to claim 1, wherein the membrane trafficking signal comprises the amino acid sequence as set forth in SEQ ID NO:12.

11. The method according to claim 1, wherein the neuron-specific promoter is selected from the group consisting of a synapsin promoter, a Thy1 promoter, and a CAMKII promoter.

12. The method of claim 1, wherein the recombinant viral vector is selected from the group consisting of an adenoassociated virus vector, a retroviral vector, an adenoviral vector, a herpes simplex virus vector, and a lentiviral vector.

13. The method of claim 1, wherein the first and second light-responsive opsin proteins are expressed in the population of motor neurons responsible for the innervation of the detrusor muscle.

14. The method of claim 1, wherein the first and second light-responsive opsin proteins are expressed in the population of motor neurons responsible for innervation of the urinary sphincter muscle.

* * * * *